(12) United States Patent
Jacoby et al.

(10) Patent No.: US 8,470,607 B2
(45) Date of Patent: Jun. 25, 2013

(54) INHIBITION OF ANGIOGENESIS

(75) Inventors: Douglas B. Jacoby, Wellesley, MA (US); Abdellah Sentissi, Dover, MA (US); E. Michael Egan, Brookline, MA (US); Kamala Kesavan, West Roxbury, MA (US)

(73) Assignee: Morphotek, Inc., Exton, PA (US)

( * ) Notice: Subject to any disclaimer, the term of this patent is extended or adjusted under 35 U.S.C. 154(b) by 200 days.

(21) Appl. No.: 12/933,638

(22) PCT Filed: Sep. 17, 2008

(86) PCT No.: PCT/US2008/076740
§ 371 (c)(1),
(2), (4) Date: Sep. 20, 2010

(87) PCT Pub. No.: WO2009/117018
PCT Pub. Date: Sep. 24, 2009

(65) Prior Publication Data
US 2011/0027177 A1   Feb. 3, 2011

Related U.S. Application Data

(60) Provisional application No. 61/038,383, filed on Mar. 20, 2008, provisional application No. 61/053,651, filed on May 15, 2008.

(51) Int. Cl.
*G01N 33/566* (2006.01)
*G01N 33/53* (2006.01)
*C12N 5/00* (2006.01)
*C07K 14/00* (2006.01)

(52) U.S. Cl.
USPC ........... 436/501; 530/300; 530/324; 530/350; 435/7.1; 435/325

(58) Field of Classification Search
USPC ..... 514/13.3; 435/7.1, 325; 436/501; 530/35, 530/300, 324
See application file for complete search history.

(56) References Cited

FOREIGN PATENT DOCUMENTS
WO   WO 2005/053611   *   6/2005

OTHER PUBLICATIONS

Burgess et al. (J. Cell Biol. 111:2129-2138, 1990).*
Lazar et al. (Mol. Cell Biol. 8:1247-1252, 1998).*
Wen et al. (Proc. Natl. Acad. Sci. U.S.A. 98: 4622-4627, 2001).*
Sharma et al. (Current Pharmaceutical Design, 2007, 13, 3568-3575).*
Lyons et al. (GLIA 39:162-173, 2002).*
Chuthapisith et al., (2009), "Annexins in human breast cancer: possible predictors of pathological response to neoadjuvant chemotherapy," *European J of Cancer*, 45:1274-81.
Kesavan et al., (2010), "Annexin A2 is a molecular target for TM601, a peptide with tumor-targeting and anti-angiogenic effects," *J of Biological Chemistry*, 285(7):4366.
Lokman et al., (2011), "The role of annexin A2 in tumorigenesis and cancer progression," *Cancer Microenvironment*, published online Mar. 5, 2001, DOI 10.1007/s12307-011-0064-9.
Silva et al., (2010), "Agents that bind annexin A2 suppress ocular neovascularization," *J Cell. Physiol.*, 225:855.
Yasuda et al., (2010), "Annexin A2 autoantibodies detected in serum of cancer patients," *Anticancer Res.*, 30(7):2631-9.
Amersham Biosciences Publication, *Leadseeker* L8: 1-4, 2001, "Labelling of Proteins with CyDye N-hydroxysuccinimide Esters for Fluorescent Applications on the LEADSeeker Homogeneous Imaging System".
Akcan et al., "Chemical Re-engineering of Chlorotoxin Improves Bioconjugation Properties for Tumor Imaging and Targeted Therapy," *J. of Medicinal Chem.* 2011 (54) 782-787, 2010.
Debin et al., "Purification and Characterization of Chlorotoxin, a Chloride Channel Ligand from the Venom of the Scorpion," *Am. Physiol. Soc.* C361-C369, 1993.
Hockaday et al., "Imaging Glioma Extent with $^{131}$I-TM-601," *J. Nucl. Med.* 46(4): 580-586, 2005.
Holmes et al., "Protein Labeling with Fluorescent Probes," *Methods in Cell Biology* 63: 185-204, 2001.
Jacoby et al., "Potent Pleiotropic Anti-Angiogenic Effects of TM601, a Synthetic Chlorotoxin Peptide," *Anticancer Res.* 30: 39-46, 2010.
Kimura et al., "A Dual-Labeled Knottin Peptide for PET and Near-Infrared Fluorescence Imaging of Integrin Expression in Living Subjects," *Bioconjugage Chem.* 21 (3): 436-444, 2010.
Lyons et al., "Chlorotoxin, a Scorpion-Derived Peptide, Specifically Binds to Gliomas and Tumors of Neuroectodermal Origin," *GLIA* 39: 162-173, 2002.
Mamelak et al., "Phase I Single-Dose Study of Intracavitary-Administered Iodine-131—TM-601 in Adults With Recurrent High-Grade Glioma," *J. Clinic. Oncology* 24 (22) 3644-3650, 2006.
Mamelak et al., "Targeted Delivery of Antitumoral Therapy to Glioma and Other Malignancies with Synthetic Chlorotoxin (TM-601)," *Expert Opin. Drug Delivery* 4(2): 175-186, 2007.
Tan et al., "Deduction of Functional Peptide Motifs in Scorpion Toxins," *J. Peptide Science* 12: 420-427, 2006.
TMI 601 and TM801 Sequences (1 page)UniProtKB/Swiss-Prot: P45639.1, Apr. 18, 2012.
Veiseh et al., "Tumor Paint: A Chlorotoxin: Cy5.5 Bioconjugate for Intraoperative Visualization of Cancer Foci," *Caner Res.* 67: 6882-6888, 2007.
Ye et al., "Integrin Targeting for Tumor Optical Imaging," *Theranostics* 1: 102-126, 2011.

* cited by examiner

*Primary Examiner* — Stephen Rawlings
*Assistant Examiner* — Yan Xiao
(74) *Attorney, Agent, or Firm* — Choate Hall & Stewart LLP; Brenda Herschbach Jarrell; Atsuko N. Polzin

(57) ABSTRACT

The present invention is directed to novel methods of inhibiting angiogenesis using chlorotoxin agents. In some embodiments, the inventive methods include intravenous, intraocular, intravitreal, subjunctival injection, and/or topical administration of a chlorotoxin agent that may or may not be labeled. In some embodiments, the inventive methods allow treatment and/or amelioration of ocular diseases characterized by neovascularization, such as wet macular degeneration. In some embodiments, neovascularization is inhibited and/or newly formed vessels are caused to regress.

2 Claims, 24 Drawing Sheets

A

B

C

Inhibition of Choroidal Neovascularization

Regression of Pre-Existing New Vessels

INHIBITION OF ANGIOGENESIS

RELATED APPLICATION INFORMATION

This application is a national phase entry of international application serial number PCT/US2008/076740, filed Sep. 17, 2008, which claims priority to and benefit of U.S. provisional application Ser. Nos. 61/038,383 filed Mar. 20, 2008, and Ser. No. 61/053,651 filed May 15, 2008, the entire contents of each of which are hereby incorporated by reference in their entirety.

SEQUENCE LISTING

The present specification makes reference to a Sequence Listing (submitted electronically as a .txt file named "Seq_Listing.txt" on Sep. 20, 2010). The .txt file was generated on Sep. 20, 2010 and is 39 kb in size. The entire contents of the Sequence Listing are herein incorporated by reference.

BACKGROUND

Angiogenesis, the process by which new blood vessels are formed, occurs during normal development, reproduction, and wound repair. Aberrant angiogenesis contributes to a variety of pathological conditions including tumor growth, ocular neovascularization, and arthritis.

Chlorotoxin is a peptide found in venom from the Giant Yellow Israeli scorpion *Leiurus Quinqestriatus* that has been explored pre-clinically as a candidate for targeting gliomas. Compositions and methods (see U.S. Pat. Nos. 5,905,027; 6,028,174; 6,319,891; and 6,429,187, the contents of each of which are hereby incorporated by reference in their entirety) for diagnosing and treating tumors have been developed based on the ability of chlorotoxin to bind to tumor cells.

SUMMARY

Because of its role in pathologic conditions such as cancer, angiogenesis is an attractive target for potential therapeutics. Nevertheless, inhibition of angiogenesis is complicated by the multiple pathways that regulate angiogenesis. Vascular endothelial growth factor (VEGF) is induced by hypoxia-inducible factor (HIF) and is a prominent pro-angiogenic factor. Several anti-angiogenic therapeutics target VEGF specifically.

Tumor cells are capable of switching of signaling pathways, which may allow them to become resistant to certain angiogenesis inhibitors. For example, treatment of cells with HIF pathway inhibitors (such as VEGF inhibitors) may lead to selection of tumors that can use HIF-independent pathways to stimulate angiogenesis and continue to grow and/or metastasize. Among other things, the present invention encompasses the recognition that broad-spectrum inhibition of angiogenesis (that is, across multiple signaling pathways), which is not observed in any of the FDA approved angiogenesis inhibitors, would be advantageous.

Disclosed herein are novel strategies for inhibiting angiogenesis. The present invention encompasses the finding that chlorotoxin agents can inhibit neovascularization and/or cause regression of existing newly formed blood vessels. The inventors have discovered that chlorotoxin agents can inhibit neovascularization stimulated by a broad spectrum of pro-angiogenic factors, which has so far not been reported for currently marketed angiogenesis inhibitors. Furthermore, chlorotoxin agents can exert anti-angiogenic effects when delivered via various routes of administration, including intravenous, intraocular, and topical. Several exemplified routes of administration result in delivery of chlorotoxin agents to the eye.

In some aspects, the invention provides methods comprising a step of administering an amount of chlorotoxin agent to a subject, wherein the amount of chlorotoxin is effective such that extent of angiogenesis is reduced as compared with that observed or expected for a control subject to whom chlorotoxin agent is not administered. In some embodiments, the chlorotoxin agent selectively targets cancer cells over normal cells. The subject may have a tumor, such as, for example, a metastatic tumor. The subject may have, for example, at least one metastasis. In some embodiments, the size of the tumor and/or metastasis is reduced.

In certain embodiments, the subject is suffering from or susceptible to a condition or disease characterized by aberrant angiogenesis. For example, the condition or disease may be characterized by choroidal neovascularization. Examples of such conditions or diseases include, but are not limited to, macular degeneration (including wet macular degeneration, age-related macular degeneration, etc.), myopia, ocular trauma, pseudoxanthoma elasticum, and combinations thereof.

In some embodiments, angiogenesis is stimulated by a factor selected from the group consisting of vascular endothelial growth factor (VEGF), basic fibroblast growth factor (bFGF), lipopolysaccharide (LPS), epidermal growth factor (EGF), interleukin-6 (IL-6), platelet-derived growth factor (PDGF), tumor necrosis factor (TNFα), hepatocyte growth factor (HGF), and combinations thereof.

In some embodiments, the chlorotoxin agent is administered by a route of administration selected from the group consisting of intravenous, intracranial, intramuscular, intratumoral, subcutaneous, intraocular, periocular topical application, and combinations thereof. In some embodiments, the cholorotoxin agent is administered intravitreally, by subconjunctival injection, etc.

In certain embodiments, the chlorotoxin agent is delivered to the eye. Administration may, for example, use intraocular and/or periocular routes as mentioned herein. Alternatively or additionally, eye drops may be used to deliver chlorotoxin agents to the eye.

In certain embodiments, the chlorotoxin agent is associated with a cytotoxic moiety. In some embodiments, chlorotoxin agent is fused with the cytotoxic moiety to form a fusion protein. The cytotoxic moiety may be, for example, selected from the group consisting of toxins, bioactive proteins, chemotherapeutic antibiotics, nucleolytic enzymes, radioisotopes, and combinations thereof. Examples of toxins include, but are not limited to, gelonin, ricin, saponin, *Pseudomonas* exotoxin, pokeweed antiviral protein, diphtheria toxin, complement proteins, and combinations thereof. In some embodiments, the cytotoxic moiety comprises a radioisotope. For example, the radioisotope may comprise iodine-131 ($^{131}$I).

In certain embodiments, the chlorotoxin agent is associated with a labeling moiety. The labeling moiety may, for example, comprise a moiety selected from the group consisting of fluorophores, radioisotopes, paramagnetic metal ions, and combinations thereof. In some embodiments, the labeling moiety comprises a radioisotope such as, for example, iodine-131 ($^{131}$I), iodine-125 ($^{125}$I), a combination thereof, etc. In some embodiments, the radioisotope comprises $^{99m}$Tc.

In certain embodiments, the chlorotoxin agent is covalently attached to a polymer. The polymer may be, for example, polyethylene glycol (PEG).

In certain embodiments, the half-life of the chlorotoxin agent in the subject is at least approximately 10 hours. In some embodiments, the half-life is at least approximately 16 hours.

In certain embodiments, the chlorotoxin agent is administered fewer than five times a week. In some embodiments, the chlorotoxin agent is administered fewer than two times a week In some embodiments, the extent of angiogenesis is reduced by at least 50% as compared to the control subject.

In some embodiments, the chlorotoxin agent causes regression of existing neovasculature. In some embodiments, the chlorotoxin agent prevents sprouting of new vessels.

The present invention further encompasses the recognition that Annexin A2 is a desirable target for drug development. In some embodiments, a chlorotoxin agent administered as described herein binds to Annexin A2. Binding between such a chlorotoxin agent and annexin A2 may be direct or indirect.

In some aspects, the invention provides methods of identifying agents that bind to Annexin A2, comprising providing a sample comprising cells that express Annexin A2; contacting a sample with a test agent; determining whether the test agent binds to Annexin A2; and identifying, based on the determination, the test agent as an agent that binds to Annexin A2. In some embodiments, such methods further comprise determining whether the agent modulates Annexin A2 function.

In some aspects, the invention provides methods of modulating Annexin A2 activity of a cell that expresses Annexin A2 comprising contacting the cell with an agent that modulates Annexin A2 such that Annexin A2 activity is altered.

In certain embodiments, the present invention provides therapeutic strategies that comprise administering a chlorotoxin agent to a subject and that further comprise administering a second therapeutic agent. The second therapeutic agent may be, for example, an anti-cancer agent, an angiogenesis inhibitor, etc. In some embodiments, the angiogenesis inhibitor is selected from the group consisting of bevacizumab, ranibizumab, and combinations thereof. The chlorotoxin agent and the second therapeutic agent may be administered at the same time. In some embodiments, the chlorotoxin agent is administered before the second therapeutic agent is administered. In some embodiments, the chlorotoxin agent is administered after the second therapeutic agent is administered. The chlorotoxin agent may be associated with the second therapeutic agent. In certain embodiments, the chlorotoxin agent is administered in combination with at least one other agent that binds to and/or modulates Annexin A2. In certain embodiments, the chlorotoxin agent is administered in combination with at least one other therapeutic agent or is administered in conjuction with at least one other therapy for ocular neovascularization disorders such as macular degeneration. Such therapeutic agents may include angiogenesis inhibitors such as Luctentis™ and Macugen™; such therapies may include photocoagulation, e.g., treatment with a laser.

DEFINITIONS

Figure 1:
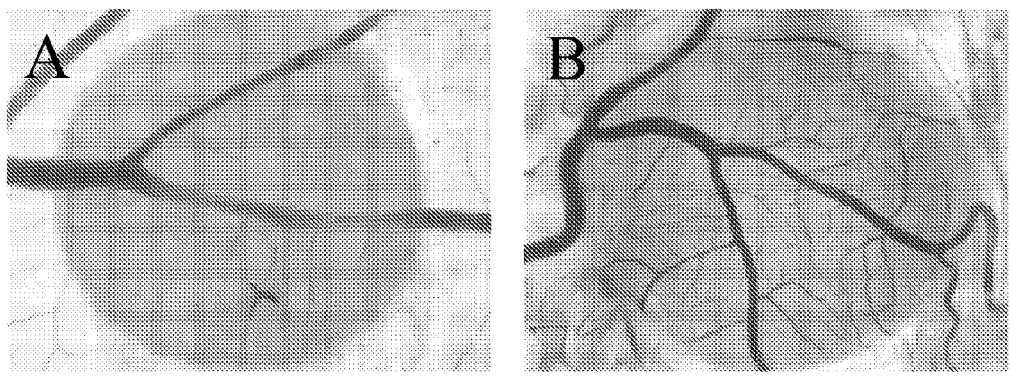
FIG. 1 depicts photographs showing stimulation of angiogenesis by VEGF in the chick chorioallantoic (CAM) assay. Untreated (A) and VEGF treated (B) CAMs were photographed to show the increase in vascular branch points in response to topical application of VEGF to the CAM.

Throughout the specification, several terms are employed that are defined in the following paragraphs.

As used herein, the terms "about" and "approximately," in reference to a number, is used herein to include numbers that fall within a range of 20%, 10%, 5%, or 1% in either direction (greater than or less than) the number unless otherwise stated or otherwise evident from the context (except where such number would exceed 100% of a possible value).

As used herein, the term "Annexin A2" refers to a protein product of the gene whose official symbol is ANXA2 (in *Homo sapiens*) and whose official full name is "annexin A2" in the Entrez Gene listing at http://www.ncbi.nlm.nih.gov, (A variety of sequences for ANXA2 transcripts can be found, for example, under GenBank accession nos. M62899, NM_001002857, NM_001002858, NM_004039.) Annexin A2 is also known, among other things as "annexin II," and lipocortin 2.

The term "biologically active", when used herein to characterize a polypeptide, refers to a molecule that shares sufficient amino acid sequence homology with a parent polypeptide to exhibit similar or identical properties than the polypeptide (e.g., ability to specifically bind to cancer cells and/or to be internalized into cancer cells and/or to kill cancer cells).

As used herein, the term "cancer" refers to or describes the physiological condition in mammals that is typically characterized by unregulated cell growth. Examples of cancers include, but are not limited to carcinoma, lymphoma, blastoma, sarcoma, and leukemia. More particularly, examples of such cancers include lung cancer, bone cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma.

As used herein, the term "cancer cell" refers to a cell in a mammal (e.g., a human being) in vivo which undergoes undesired and unregulated cell growth or abnormal persistence or abnormal invasion of tissues. In vitro, this term also refers to a cell line that is a permanently immortalized established cell culture that will proliferate indefinitely and in an unregulated manner given appropriate fresh medium and space.

As used herein, the term "cancer patient" can refer to an individual suffering from or susceptible to cancer. A cancer patient may or may not have been diagnosed with cancer. The term also includes individuals that have previously undergone therapy for cancer.

The terms "chemotherapeutics" and "anti-cancer agents or drugs" are used herein interchangeably. They refer to those medications that are used to treat cancer or cancerous conditions. Anti-cancer drugs are conventionally classified in one of the following group: alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones and anti-androgens. Examples of such anti-cancer agents include, but are not limited to, BCNU, cisplatin, gemcitabine, hydroxyurea, paclitaxel, temozolomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomycin, tamoxifen, flutamide, leuprolide, goserelin, aminogluthimide, anastrozole, amsacrine, asparaginase, mitoxantrone, mitotane and amifostine.

The term "combination therapy", as used herein, refers to those situations in which two or more different pharmaceutical agents are administered in overlapping regimens so that the subject is simultaneously exposed to both agents.

The term "cytotoxic", when used herein to characterize a moiety, compound, drug or agent refers to a moiety, compound, drug or agent that inhibits or prevents the function of cells and/or causes destruction of cells.

A "dosing regimen", as that term is used herein, refers to a set of unit doses (typically more than one) that are administered individually separated by periods of time. The recommended set of doses (i.e., amounts, timing, route of administration, etc.) for a particular pharmaceutical agent constitutes its dosing regimen.

As used herein, the terms "effective amount" and "effective dose" refer to any amount or dose of a compound or composition that is sufficient to fulfill its intended purpose(s), i.e., a desired biological or medicinal response in a tissue or subject at an acceptable benefit/risk ratio. For example, in certain embodiments of the present invention, the purpose(s) may be: to inhibit angiogenesis, cause regression of neovasculature, interfere with activity of another bioactive molecule such as Annexin A2, etc. The relevant intended purpose may be objective (i.e., measurable by some test or marker) or subjective (i.e., subject gives an indication of or feels an effect). A therapeutically effective amount is commonly administered in a dosing regimen that may comprise multiple unit doses. For any particular pharmaceutical agent, a therapeutically effective amount (and/or an appropriate unit dose within an effective dosing regimen) may vary, for example, depending on route of administration, on combination with other pharmaceutical agents. In some embodiments, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific pharmaceutical agent employed; the duration of the treatment; and like factors as is well known in the medical arts.

As used herein, terms "fluorophore", "fluorescent moiety", "fluorescent label", "fluorescent dye" and "fluorescent labeling moiety" are used herein interchangeably. They refer to a molecule that, in solution and upon excitation with light of appropriate wavelength, emits light back. Numerous fluorescent dyes of a wide variety of structures and characteristics are suitable for use in the practice of this invention. Similarly, methods and materials are known for fluorescently labeling nucleic acids (see, for example, R. P. Haugland, "*Molecular Probes: Handbook of Fluorescent Probes and Research Chemicals* 1992-1994", 5$^{th}$ Ed., 1994, Molecular Probes, Inc.). In choosing a fluorophore, it is often desirable that the fluorescent molecule absorbs light and emits fluorescence with high efficiency (i.e., high molar absorption coefficient and fluorescence quantum yield, respectively) and is photostable (i.e., it does not undergo significant degradation upon light excitation within the time necessary to perform the analysis).

As used herein, the term "fusion protein" refers to a molecule comprising two or more proteins or fragments thereof linked by a covalent bond via their individual peptide backbones, often generated through genetic expression of a polynucleotide molecule encoding those proteins.

As used herein, the term "homologous" (or "homology") refers to a degree of identity between two polypeptide molecules or between two nucleic acid molecules. When a position in both compared sequences is occupied by the same base or amino acid monomer subunit, then the respective molecules are homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid residues. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g., that have a similar size, shape, electric charge, chemical properties, including the ability to form covalent or hydrogen bonds, or the like. In some embodiments, conservative substitutions utilized in accordance with the present invention are those fulfilling the criteria defined for an "accepted point mutation" by Dayhoff et al. ("Atlas of Protein Sequence and Structure", 1978, Nat. Biomed. Res. Foundation, Washington, D.C., Suppl. 3, 22: 354-352).

As used herein, the term "homologue" refers to a polypeptide or gene that shows a designated degree of sequence identity (and/or similarity) with another polypeptide or gene. For example, any polypeptide that shows at least about 30-40% overall sequence identity with another polypeptide, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide is a homolog of that polypeptide. In many embodiments, a homolog of a polypeptide further shares sequence similarity with and/or at least one functional attribute or activity of the polypeptide. With regard to genes or nucleotide sequences, any gene or nucleotide sequence that (i) shows at least about 60% overall sequence identity with another gene or nucleotide sequence; and or (ii) encodes a homolog of a polypeptide encoded by the other gene or nucleotide sequence is a homolog of that gene or nucleotide sequence. As is known by those of ordinary skill in the art, a variety of strategies are known, and tools are available, for performing comparisons of amino acid or nucleotide sequences in order to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTAL-W etc. When utilizing BLAST and Gapped BLAST programs, default parameters of the respective programs may be used. Alternatively, the practitioner may use non-default parameters depending on his or her experimental and/or other requirements (see for example, the Web site having URL www.ncbi.nlm.nih.gov).

The terms "individual" and "subject" are used herein interchangeably. They refer to a human or another mammal (e.g., mouse, rat, rabbit, dog, cat, cattle, swine, sheep, horse or primate) that can be afflicted with or is susceptible to a disease or disorder (e.g., cancer, macular degeneration, etc.) but may or may not have the disease or disorder. In many embodiments, the subject is a human being. In many embodiments, the subject is a patient. Unless otherwise stated, the terms "individual" and "subject" do not denote a particular age, and thus encompass adults, children, and newborns.

As used herein, the term "inhibit" means to prevent something from happening, to delay occurrence of something happening, and/or to reduce the extent or likelihood of something happening. Thus, "inhibiting angiogenesis" and "inhibiting the formation of neovasculature" is intended to encompass preventing, delaying, and/or reducing the likelihood of angiogenesis occurring as well as reducing the number, growth rate, size, etc., of neovessels.

The terms "labeled" and "labeled with a detectable agent or moiety" are used herein interchangeably to specify that an entity (e.g., a chlorotoxin or chlorotoxin conjugate) can be visualized, for example following binding to another entity (e.g., a neoplastic tumor tissue). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionuclides, fluorophores, chemiluminescent agents, microparticles, enzymes, colorimetric labels, magnetic labels, haptens, Molecular Beacons, aptamer beacons, and the like.

As used herein, the term "macular degeneration" refers to a medical condition that results in loss of vision in the center of the visual field (the macula) because of damage to the retina. Several forms of macular degeneration are known to exist, and unless specified, the term "macular degeneration" includes all forms. "Wet macular degeneration" (also known as the neovascular or exudative form) refers to macular degeneration that involves the growth of blood vessels from the choroid behind the retina. In wet macular degeneration, the retina may sometimes become detached. In "dry macular degeneration" (also known as the non-exudative form), cellular debris called drusen accumulate between the retina and the choroid, but no blood vessel formation occurs. "Age-related macular degeneration" (ARMD) refers to the most common form of macular degeneration, which typically begins later in life with characteristic yellow deposits in the macula. ARMD may occur in either the wet or dry forms of macular degeneration.

As used herein, the term "metastasis" (sometimes abbreviated as "mets;" plural "metastases") refers to the spread of tumor cells from one organ or tissue to another location. The term also refers to tumor tissue that forms in a new location as a result of metastasis. A "metastatic cancer" is a cancer that spreads from its original, or primary, location, and may also be referred to as a "secondary cancer" or "secondary tumor." Generally, metastatic tumors are named for the tissue of the primary tumor from which they originate. Thus, a breast cancer that has metastasized to the lung may be referred to as "metastatic breast cancer" even though some cancer cells are located in the lung.

As used herein, the term "neovasculature" refers to newly formed blood vessels that have not yet fully matured, i.e., do not have a fully formed endothelial lining with tight cellular junctions or a complete layer of surrounding smooth muscle cells. As used herein, the term "neovessel" is used to refer to a blood vessel in neovasculature.

The terms "normal" and "healthy" are used herein interchangeably. They refer to an individual or group of individuals who do not have a tumor. The term "normal" is also used herein to qualify a tissue sample isolated from a healthy individual.

The terms "pharmaceutical agent", "therapeutic agent" and "drug" are used herein interchangeably. They refer to a substance, molecule, compound, agent, factor or composition effective in the treatment, inhibition, and/or detection of a disease, disorder, or clinical condition.

A "pharmaceutical composition" is herein defined as a composition that comprises an effective amount of at least one active ingredient (e.g., a chlorotoxin or chlorotoxin conjugate that may or may not be labeled), and at least one pharmaceutically acceptable carrier.

As used herein, the term "pharmaceutically acceptable carrier" refers to a carrier medium which does not interfere with the effectiveness of the biological activity of the active ingredient(s) and which is not excessively toxic to the host at the concentration at which it is administered. The term includes solvents, dispersion media, coatings, antibacterial and antifungal agents, isotonic agents, absorption delaying agents, and the like. The use of such media and agents for pharmaceutically active substances is well known in the art (see for example, "*Remington's Pharmaceutical Sciences*", E. W. Martin, 18th Ed., 1990, Mack Publishing Co.: Easton, Pa., which is incorporated herein by reference in its entirety).

As used herein, the term "preventing" when used to refer to the action of an agent to a process (e.g., angiogenesis) means reducing extent of and/or delaying onset of such a process when the agent (e.g., a therapeutic agent) is administered prior to development of one or more symptoms or attributes associated with the process.

As used herein, the term "primary tumor" refers to a tumor that is at the original site where the tumor first arose, i.e., as opposed to having spread there.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is the full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains, such as oxidation of sulfhydryl groups. Thus, the term "protein" (or its equivalent terms) is intended to include the amino acid sequence of the full-length native protein, subject to those modifications that do not change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative slicing or limited proteolysis), or in the alternative, may arise from differential post-translational modification (e.g., glycosylation, acylation or phosphorylation).

The term "protein analog", as used herein, refers to a polypeptide that possesses a similar or identical function as a parent polypeptide but need not necessarily comprise an amino acid sequence that is similar or identical to the amino acid sequence of the parent polypeptide, or possess a structure that is similar or identical to that of the parent polypeptide. In the context of the present invention, a protein analog may have an amino acid sequence that is at least 30% (in some embodiments, at least 35%, at least 40%, at least 45%, at least 50%, at least 55%, at least 60%, at least 65%, at least 70%, at least 75%, at least 80%, at least 85%, at least 90%, at least 95% or at least 99%) identical to the amino acid sequence of the parent polypeptide. Moreover, those of ordinary skill in the art will understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90%, 96%, 97%, 98% or 99% in one or more highly conserved regions usually encompassing at least 3-4 and often up to 20 or more amino acids, with the parent polypeptide, is encompassed in the term "protein analog).

As used herein, the term "protein fragment" refers to a polypeptide comprising an amino acid sequence of at least 5 amino acid residues of the amino acid sequence of a second polypeptide. A fragment of a protein may or may not possess a functional activity of the parent polypeptide.

The term "regress," when used to refer to blood vessels and/or vasculature (including neovasculature and/or neovessels), is used herein to mean to retract, shrink, etc.

As used herein, the term "small molecule" includes any chemical or other moiety that can act to affect biological processes. Small molecules can include any number of therapeutic agents presently known and used, or can be small molecules synthesized in a library of such molecules for the purpose of screening for biological function(s). Small molecules are distinguished from macromolecules by size. Small molecules suitable for use in the present invention usually have molecular weight less than about 5,000 daltons (Da), less than about 2,500 Da, less than 1,000 Da, or less than about 500 Da.

As used herein, the term "susceptible" means having an increased risk for and/or a propensity for (typically based on genetic predisposition, environmental factors, personal history, or combinations thereof) something, i.e., a disease, disorder, or condition such as metastatic cancer, than is observed in the general population. The term takes into account that an individual "susceptible" for a condition may never be diagnosed with the condition.

As used herein, the term "systemic administration" refers to administration of an agent such that the agent becomes widely distributed in the body in significant amounts and has a biological effect, e.g., its desired effect, in the blood and/or reaches its desired site of action via the vascular system. Typical systemic routes of administration include administration by (1) introducing the agent directly into the vascular system or (2) oral, pulmonary, or intramuscular administration wherein the agent is adsorbed, enters the vascular system, and is carried to one or more desired site(s) of action via the blood.

The term "tissue" is used herein in its broadest sense. A tissue may be any biological entity that can (but does not necessarily) comprise a tumor cell. In the context of the present invention, in vitro, in vivo and ex vivo tissues are considered. Thus, a tissue may be part of an individual or may be obtained from an individual (e.g., by biopsy). Tissues may also include sections of tissue such as frozen sections taken for histological purposes or archival samples with known diagnosis, treatment and/or outcome history. The term tissue also encompasses any material derived by processing the tissue sample. Derived materials include, but are not limited to, cells (or their progeny) isolated from the tissue. Processing of the tissue sample may involve one or more of: filtration, distillation, extraction, concentration, inactivation of interfering components, addition of reagents, and the like.

The term "treatment" is used herein to characterize a method or process that is aimed at (1) delaying or preventing the onset of a disease, disorder, or condition; (2) slowing down or stopping the progression, aggravation, or deterioration of one or more symptoms of the disease, disorder, or condition; (3) bringing about ameliorations of the symptoms of the disease, disorder, or condition; (4) reducing the severity or incidence of the disease, disorder, or condition; or (5) curing the disease, disorder, or condition. A treatment may be administered prior to the onset of the disease, disorder, or condition, for a prophylactic or preventive action. Alternatively or additionally, the treatment may be administered after initiation of the disease, disorder, or condition, for a therapeutic action.

DETAILED DESCRIPTION OF CERTAIN EMBODIMENTS

The present invention is directed, among other things, to methods of inhibiting and/or reducing angiogenesis. Methods provided herein often comprise administration of a chlorotoxin agent that may or may not be associated with a cytotoxic moiety, a second therapeutic agent, a labeling moiety and/or combinations thereof. Chlorotoxin agents may be covalently attached to a polymer such as, for example, polyethylene glycol. In certain embodiments, the formation of new blood vessels is inhibited and/or existing neovasculature regresses.

In accordance with the present invention there may be employed conventional molecular biology, microbiology, and recombinant DNA techniques within the skill of the art. Such techniques are explained fully in the literature. See, e.g., Maniatis, Fritsch & Sambrook, "*Molecular Cloning: A Laboratory Manual*", 1982; "*DNA Cloning: A Practical Approach*," Volumes I and II, D. N. Glover (Ed.), 1985; "*Oligonucleotide Synthesis*", M. J. Gait (Ed.), 1984; "*Nucleic Acid Hybridization*", B. D. Hames & S. J. Higgins (Eds.), 1985; "*Transcription and Translation*" B. D. Hames & S. J. Higgins (Eds.), 1984; "*Animal Cell Culture*", R. I. Freshney (Ed.), 1986; "*Immobilized Cells And Enzymes*", IRL Press, 1986; B. Perbal, "*A Practical Guide To Molecular Cloning*", 1984.

I. Agents and Moieties

Methods of the present invention may involve administration to a subject (such as, for example, a subject who has, has had, or is at risk of developing a condition or disease characterized by aberrant angiogenesis), of amount of a chlorotoxin agent effective such that angiogenesis is reduced as compared to a control.

A. Chlorotoxin Agents

As used herein, the term "chlorotoxin agent" refers to a compound that comprises at least one chlorotoxin moiety. In certain embodiments, a chlorotoxin agent is associated with a second therapeutic agent (e.g., an anti-cancer agent). The chlorotoxin agent (and/or therapeutic agent) may be associated with at least one labeling moiety.

As used herein, the term "chlorotoxin moiety" refers to a chlorotoxin, a biologically active chlorotoxin subunit or a chlorotoxin derivative.

In certain embodiments, the term "chlorotoxin" refers to the full-length, 36 amino acid polypeptide naturally derived from *Leiurus quinquestriatus* scorpion venom (DeBin et al., Am. J. Physiol., 1993, 264: C361-369), which comprises the amino acid sequence of native chlorotoxin as set forth in SEQ ID NO. 1 of International Application No. WO 2003/101474, the contents of which are incorporated herein by reference. The term "chlorotoxin" includes polypeptides comprising SEQ ID NO. 1 which have been synthetically or recombinantly produced, such as those disclosed in U.S. Pat. No. 6,319,891 (which is incorporated herein by reference in its entirety).

A "biologically active chlorotoxin subunit" is a peptide comprising less than the 36 amino acids of chlorotoxin and which retains at least one property or function of chlorotoxin. As used herein, a "property or function" of chlorotoxin includes, but is not limited to, its ability to ability to suppress formation of and/or cause regression of neovessels; ability to interfere with activity of its binding partner(s) (which may include, for example, Annexin A2); ability to arrest abnormal cell growth; ability to specifically bind to a tumor/cancer cell compared to a normal cell; ability to specifically bind to a metastasizing tumor/cancer cell or a tumor/cancer cell in a metastasis compared to a normal cell; ability to be internalized into a tumor/cancer cell; ability to kill a tumor/cancer cell. The tumor/cancer cell may be in vitro, ex vivo, in vitro, part of a metastasis, a primary isolate from a subject, a cultured cell, or a cell line.

As used herein, the term "biologically active chlorotoxin derivative" refers to any of a wide variety of derivatives, analogs, variants, polypeptide fragments and mimetics of chlorotoxin and related peptides which retain at least one property or function of chlorotoxin (as described above). Examples of chlorotoxin derivatives include, but are not limited to, peptide variants of chlorotoxin, peptide fragments of chlorotoxin, for example, fragments comprising or consisting of contiguous 10-mer peptides of SEQ ID No. 1, 2, 3, 4, 5, 6, or 7 as set forth in International Application No. WO 2003/101474 or comprising residues 10-18 or 21-30 of SEQ ID No. 1 as set forth in International Application No. WO 2003/101474, core binding sequences, and peptide mimetics.

Examples of chlorotoxin derivatives include peptides having a fragment of the amino acid sequence set forth in SEQ ID No. 1 of International Application No. WO 2003/101474, having at least about 7, about 8, about 9, about 10, about 15, about 20, about 25, about 30 or about 35 contiguous amino acid residues, associated with the activity of chlorotoxin. Such fragments may contain functional regions of the chlorotoxin peptide, identified as regions of the amino acid sequence that correspond to known peptide domains, as well as regions of pronounced hydrophilicity. Such fragments may also include two core sequences linked to one another, in any order, with intervening amino acid removed or replaced by a linker.

Derivatives of chlorotoxin include polypeptides comprising a conservative or non-conservative substitution of at least one amino acid residue when the derivative sequence and the chlorotoxin sequence are maximally aligned. The substitution may be one that enhances at least one property or function of chlorotoxin, inhibits at least one property or function of chlorotoxin, or is neutral to at least one property or function of chlorotoxin.

Examples of derivatives of chlorotoxin suitable for use in the practice of the present invention are described in International Application No. WO 2003/101474 (which is incorporated herein by reference in its entirety). Particular examples include polypeptides that comprise or consist of SEQ ID NO. 8 or SEQ ID NO. 13 as set forth in this International Application, as well as variants, analogs, and derivatives thereof.

Other examples of chlorotoxin derivatives include those polypeptides containing pre-determined mutations by, e.g., homologous recombination, site-directed or PCR mutagenesis, and the alleles or other naturally-occurring variants of the family of peptides; and derivatives wherein the peptide has been covalently modified by substitution, chemical, enzymatic or other appropriate means with a moiety other than a naturally-occurring amino acid (for example a detectable moiety such as enzyme or a radioisotope).

Chlorotoxin and peptide derivatives thereof can be prepared using any of a wide variety of methods, including standard solid phase (or solution phase) peptide synthesis methods, as is known in the art. In addition, the nucleic acids encoding these peptides may be synthesized using commercially available oligonucleotide synthesis instrumentation and the proteins may be produced recombinantly using standard recombinant production systems.

Other suitable chlorotoxin derivatives include peptide mimetics that mimic the three-dimensional structure of chlorotoxin. Such peptide mimetics may have significant advantages over naturally occurring peptides including, for example, more economical production, greater chemical stability, enhanced pharmacological properties (half-life, absorption, potency, efficacy, etc), altered specificity (e.g., broad-spectrum biological activities, reduced antigenicity and others).

In certain embodiments, mimetics are molecules that mimic elements of chlorotoxin peptide secondary structure. Peptide backbones of proteins exist mainly to orient amino acid side chains in such a way as to facilitate molecular interactions, such as those of antibody and antigen. A peptide mimetic is expected to permit molecular interactions similar to the natural molecule. Peptide analogs are commonly used in the pharmaceutical industry as non-peptide drugs with properties analogous to those of the template peptide. These types of compounds are also referred to as peptide mimetics or peptidomimetics (see, for example, Fauchere, Adv. Drug Res., 1986, 15: 29-69; Veber & Freidinger, 1985, Trends Neurosci., 1985, 8: 392-396; Evans et al., J. Med. Chem., 1987, 30: 1229-1239) and are usually developed with the aid of computerized molecular modeling.

Generally, peptide mimetics are structurally similar to a paradigm polypeptide (i.e., a polypeptide that has a biochemical property or pharmacological activity), but have one or more peptide linkages optionally replaced by a non-peptide linkage. The use of peptide mimetics can be enhanced through the use of combinatorial chemistry to create drug libraries. The design of peptide mimetics can be aided by identifying amino acid mutations that increase or decrease the binding of a peptide to, for example, a tumor cell. Approaches that can be used include the yeast two hybrid method (see, for example, Chien et al., Proc. Natl. Acad. Sci. USA, 1991, 88: 9578-9582) and using the phase display method. The two-hybrid method detects protein-protein interactions in yeast (Field et al., Nature, 1989, 340: 245-246). The phage display method detects the interaction between an immobilized protein and a protein that is expressed on the surface of phages such as lambda and M13 (Amberg et al., Strategies, 1993, 6: 2-4; Hogrefe et al., Gene, 1993, 128: 119-126). These methods allow positive and negative selection of peptide-protein interactions and the identification of the sequences that determine these interactions.

In certain embodiments, a chlorotoxin agent comprises a polypeptide toxin of another scorpion species that displays similar or related activity to chlorotoxin described above. As used herein, the term "similar or related activity to chlorotoxin" refers, in particular, to the selective/specific binding to tumor/cancer cells. Examples of suitable related scorpion toxins include, but are not limited to toxins or related peptides of scorpion origin that display amino acid and/or nucleotide sequence identity to chlorotoxin. Examples of related scorpion toxins include, but are not limited to, CT neurotoxin from *Mesobuthus martenssi* (GenBank Accession No. AAD473730), Neurotoxin BmK 41-2 from *Buthus martensii karsch* (GenBank Accession No. A59356), Neurotoxin Bm12-b from *Buthus martensii* (GenBank Accession No. AAK16444), Probable Toxin LGH 8/6 from *Leiurus quinquestriatus hebraeu* (GenBank Accession No. P55966), and Small toxin from *Mesubutus tamulus sindicus* (GenBank Accession No. P15229).

Related scorpion toxins suitable for use in the present invention comprise polypeptides that have an amino acid sequence of at least about 75%, at least about 85%, at least about 90%, at least about 95%, or at least about 99% sequence identity with the entire chlorotoxin sequence as set forth in SEQ ID No. 1 of International Application No. WO 2003/101474 (which is incorporated herein by reference in its entirety). In certain embodiments, related scorpion toxins include those scorpion toxins that have a sequence homologous to SEQ ID NO. 8 or SEQ ID NO. 13 of chlorotoxin, as set forth in International Application No. WO 2003/101474.

Modifications

In certain embodiments, chlorotoxin agents are unlabeled. In certain embodiments, chlorotoxin agents are labeled. Examples of labeling methods and labeling moieties are described herein.

In certain embodiments, chlorotoxin agents are modified by covalent attachment to macromolecules such as polymers. Without wishing to be bound by any particular theory, covalent attachment of, for example, polymers, may mask the chlorotoxin agent antigenically such that the agent's bioavailability and/or tolerance in an animal's body is improved. An example of such a polymer is polyethylene glycol (PEG), which can often be covalently attached to N and/or C termini and/or to cysteines in peptides and/or polypeptides. "PEGylation" refers to the covalent addition of PEG to a molecule.

In some embodiments, chlorotoxin agents are not modified at any site. In some embodiments, chlorotoxin agents are modified (e.g., by PEGylation) at one site per molecule. In some embodiments, chlorotoxin agents are modified (e.g., by PEGylation) at more than one site per molecule.

In some embodiments, such modifications increase the half life of chlorotoxin agents in vivo. For example, the half life may be at least approximately 10 hours, at least approximately 16 hours, etc. (See, e.g., Example 7). Such improved bioavailability may in some embodiments facilitate dosing regimens that involve lower frequencies of dosing. (Dosing regimens are discussed herein.)

Binding of Chlorotoxin Agents to Cells

Chlorotoxin agents may, for example, bind to cells via an antigen present on the outer surface of cell membranes.

Data presented and discussed herein indicate that Annexin A2 is a potential binding partner for chlorotoxin. In some embodiments, the antigen is Annexin A2 or a related family member. In some embodiments, chlorotoxin agents bind Annexin A2 directly. In some embodiments, chlorotoxin agents bind Annexin A2 indirectly, e.g., through association with other molecules. Chlorotoxin agents and Annexin A2 may, for example, exist in a complex that comprises other molecules.

In certain embodiments, chlorotoxin agents bind to cancer cells; in some such embodiments, chlorotoxin agents selectively target cancer cells over normal cells.

B. Second Therapeutic Agents

As already mentioned above, in certain embodiments, a chlorotoxin agent may be associated with second therapeutic agent and/or the methods may comprise further steps including administering a second therapeutic agent. In some embodiments, the chlorotoxin agent and the second therapeutic agent are administered at the same time. In some embodiments, the chlorotoxin agent is administered before and/or after the second therapeutic agent is administered. In some embodiments, the chlorotoxin agent and the second therapeutic agent are administered within a time window such that their periods of activity and/or efficacy in the body overlap. Without wishing to be bound by any particular theory, administering a second therapeutic agent in combination with chlorotoxin agents may, in some embodiments, provide an additive and/or synergistic effect on inhibiting and/or preventing angiogenesis.

Suitable therapeutic agents include any of a large variety of substances, molecules, compounds, agents or factors that are effective in the treatment of a disease or clinical condition. In certain embodiments, a second therapeutic agent is a chemotherapeutic (i.e., an anti-cancer drug). Suitable anti-cancer drugs include any of a large variety of substances, molecules, compounds, agents or factors that are directly or indirectly toxic or detrimental to cancer cells.

As will be appreciated by one of ordinary skill in the art, a therapeutic agent may be a synthetic or natural compound: a single molecule, a mixture of different molecules or a complex of different molecules. Suitable therapeutic moieties can belong to any of a variety of classes of compounds including, but not limited to, small molecules, peptides, proteins, saccharides, steroids, antibodies (including fragments and variants thereof), fusion proteins, antisense polynucleotides, ribozymes, small interfering RNAs, peptidomimetics, radionuclides, and the like.

When a second therapeutic agent comprises an anti-cancer drug, the anti-cancer drug can be found, for example, among the following classes of anti-cancer drugs: alkylating agents, anti-metabolic drugs, anti-mitotic antibiotics, angiogenesis inhibitors, alkaloidal anti-tumor agents, hormones and anti-hormones, interferons, non-steroidal anti-inflammatory drugs, and various other anti-tumor agents such as kinase inhibitors, proteasome inhibitors and NF-κB inhibitors.

Examples of anti-cancer drugs include, but are not limited to, alkylating drugs (e.g., mechlorethamine, chlorambucil, cyclophosphamide, melphalan, ifosfamide, temozolomide, etc.), antimetabolites (e.g., methotrexate, etc.), purine antagonists and pyrimidine antagonists (e.g., 6-mercaptopurine, 5-fluorouracil, cytraribine, gemcitabine, etc.), spindle poisons (e.g., vinblastine, vincristine, vinorelbine, paclitaxel, etc.), podophyllotoxins (e.g., etoposide, irinotecan, topotecan, etc.), antibiotics (e.g., doxorubicin, bleomycin, mitomycin, etc.), nitrosureas (e.g., carmustine, lomustine, nomustine, etc.), inorganic ions (e.g., cisplatin, carboplatin, etc.), enzymes (e.g., asparaginase, etc.), and hormones (e.g., tamoxifen, leuprolide, flutamide, megestrol, etc.), to name a few. For a more comprehensive discussion of updated cancer therapies see, http://www.cancer.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Some anti-cancer drugs act by arresting the growth and/or replication of cancer cells. Such drugs are generally classified as "cytostatic." In certain embodiments, a therapeutic agent comprises a cytostatic agent. Examples of cytostatic agents include alkylating agents, anti-metabolites, plant alkyloids and terpenoids (including vinca alkaloids, podophyllotoxin, taxanes, etc.; VP-16 is an example of a plant alkaloid), topoisomerase inhibitors, antitumor antibodies, hormones, etc.

In certain embodiments, a second therapeutic agent comprises an angiogenesis inhibitor. Suitable angiogenesis inhibitors may include, but are not limited to, αVβ3 (integrin) antagonist, AG3340, AGM-1470 (a fumagillin analogue), angiopoietin-2, angiostatin, angiostatin-endostatin fusion protein, ANGIOZYME™, anti-Flk/KDR, anti-Invasive Factor, anti-VE cadherins, anti-VEGF, BMS-275291, aptamer antagonist of VEGF, batimastat, bevacizumab (Avastin™), canstatin, captopril, carboxyamidotriazole (CAI), cartilage-derived inhibitor (CDI), CM101, COL-3, combretastin A4, EMD-121974, endostatin, erlotinib (Tarceva™), estradiol derivatives, flt-1, fumagillin, gefitinib (Iressa™), genistein, IM862, interferon-alpha, interleukin-12, K5, lavendustin Alenalidomide, LM609 (antibody against αVβ3), marimastat, maspin, metastat, 2-methoxy-estradiol, neoretna, neovastat, NX 1838, pegaptanib (Macugen™), PD-173074, PI-88, oxindole derivatives, paclitaxel, psovascar, PTK787/ZK 22584, ranabizumab (Lucentis™), retinoic acids, RG8803, squalamine, S-836, SC-68448, SU5416, SU6668, SU11248 (sunitinib), TBC-1635, TBC-2653, TBC-3685, thalidomide, thiazolopyrimidine derivatives, thrombospondin 2, TNP470 (a fumagillin analogue), troponin I, vasculostatin, vitaxin, ZD0101, etc. (This list is not comprehensive.)

VEGF inhibitors include antibodies and antibody fragments against VEGF (such as, for example, Avastin™ (bevacizumab) and Lucentis™ (ranabizumab)), anti-VEGF ribozymes, aptamer inhibitors of VEGF, etc.

In some embodiments, the second therapeutic agent is a broad spectrum inhibitor. In some embodiments, the second therapeutic agent inhibits angiogenesis stimulated by one or more factors selected from the group consisting of VEGF, bFGF, LPS, EGF, IL-6, PDGF, TNFα, and HPF. In some embodiments, the second therapeutic agent does not inhibit angiogenesis stimulated by VEGF, bFGF, LPS, EGF, IL-6, PDGF, TNFα, or HPF.

In some embodiments, the second therapeutic agent is Avastin™ (bevacizumab), Lucentis™ (ranabizumab), or a combination thereof.

In certain embodiments, a second therapeutic agent comprises a cytotoxic agent. Examples of cytotoxic agents include toxins, other bioactive proteins, conventional chemotherapeutic agents, enzymes, and radioisotopes.

Examples of suitable cytotoxic toxins include, but are not limited to, bacterial and plant toxins such as gelonin, ricin, saponin, *Pseudomonas* exotoxin, pokeweed antiviral protein, diphtheria toxin, etc.

Examples of suitable cytotoxic bioactive proteins include, but are not limited to, proteins of the complement system (or complement proteins). The complement system is a complex biochemical cascade that helps clear pathogens from an organism, and promotes healing (B. P. Morgan, Crit. Rev. Clin. Lab. Sci., 1995, 32: 265). The complement system consists of more than 35 soluble and cell-bound proteins, 12 of which are directly involved in the complement pathways.

Examples of suitable cytotoxic chemotherapeutic agents include, but are not limited to, taxanes (e.g., docetaxel, paclitaxel, etc.), maytansines, duocarmycins, CC-1065, auristatins, calicheamincins and other enediyne anti-tumor antibiotics. Other examples include the anti-folates (e.g., aminopterin, methotrexate, pemetrexed, raltitrexed, etc.), vinca alkaloids (e.g., vincristine, vinblastine, etoposide, vindesine, vinorelbine, etc.), and anthracyclines (e.g., daunorubicin, doxorubicin, epirubicin, idarubicin, mitoxantrone, valrubicin, etc.).

Examples of suitable cytotoxic enzymes include, but are not limited to, nucleolytic enzymes.

Examples of suitable cytotoxic radioisotopes include any α-, β- or γ-emitter which, when localized at a tumor site, results in cell destruction (S. E. Order, "*Analysis, Results, and Future Prospective of the Therapeutic Use of Radiolabeled Antibody in Cancer Therapy*", Monoclonal Antibodies for Cancer Detection and Therapy, R. W. Baldwin et al. (Eds.), Academic Press, 1985). Examples of such radioisotopes include, but are not limited to, iodine-131 ($^{131}$I) iodine-125 ($^{125}$I), bismuth-212 ($^{212}$Bi), bismuth-213 ($^{213}$Bi), astatine-211 ($^{211}$At), rhenium-186 ($^{186}$Re), rhenium-186 ($^{188}$Re), phosphorus-32 ($^{32}$P), yttrium-90 ($^{90}$Y), samarium-153 ($^{153}$Sm), and lutetium-177 ($^{117}$Lu).

Alternatively or additionally, therapeutic agents suitable for use in the present invention may be any of the therapeutic moieties described in co-owned provisional applications entitled "Chlorotoxins as Drug Carriers" (U.S. Ser. No. 60/954,409) filed on Aug. 7, 2007, "Systemic Administration of Chlorotoxin Agents for the Diagnosis and Treatment of Tumors" (U.S. Ser. No. 60/979,714) filed on Oct. 12, 2007, the entire contents of which are incorporated herein by reference in their entirety. Examples of classes of such therapeutic agents include, but are not limited to, poorly water soluble anti-cancer agents, anti-cancer agents associated with drug resistance, antisense nucleic acids, ribozymes, triplex agents, short-interfering RNAs (siRNAs), photosensitizers, radiosensitizers, superantigens, prodrug activating enzymes, and anti-angiogenic agents.

In certain embodiments, a therapeutic (e.g., anti-cancer, anti-angiogenic, etc) agent that is associated with a chlorotoxin agent is a nucleic acid agent.

Numerous cancers and tumors have been shown to be associated with varying degrees of genetic impairment, such as point mutations, gene deletions, or duplications. Many new strategies for the treatment of cancer, such as "antisense", "antigene", and "RNA interference" have been developed to modulate the expression of genes (A. Kalota et al., Cancer Biol. Ther., 2004, 3: 4-12; Y. Nakata et al., Crit. Rev. Eukaryot. Gene Expr., 2005, 15: 163-182; V. Wacheck and U. Zangmeister-Wittke, Crit. Rev. Oncol. Hematol., 2006, 59: 65-73; A. Kolata et al., Handb. Exp. Pharmacol., 2006, 173: 173-196). These approaches utilize, for example, antisense nucleic acids, ribozymes, triplex agents, or short interfering RNAs (siRNAs) to block the transcription or translation of a specific mRNA or DNA of a target gene, either by masking that mRNA with an antisense nucleic acid or DNA with a triplex agent, by cleaving the nucleotide sequence with a ribozyme, or by destruction of the mRNA, through a complex mechanism involved in RNA-interference. In all of these strategies, mainly oligonucleotides are used as active agents, although small molecules and other structures have also been applied. While the oligonucleotide-based strategies for modulating gene expression have a huge potential for the treatment of some cancers, pharmacological applications of oligonucleotides have been hindered mainly by the ineffective delivery of these compounds to their sites of action within cancer cells. (P. Herdewijn et al., Antisense Nucleic Acids Drug Dev., 2000, 10: 297-310; Y. Shoji and H. Nakashima, Curr. Charm. Des., 2004, 10: 785-796; A. W Tong et al., Curr. Opin. Mol. Ther., 2005, 7: 114-124).

In some embodiments, agent is administered in combination with and/or comprises a second therapeutic agent that comprises a nucleic acid molecule that is useful as a therapeutic (e.g., anti-cancer) agent. A variety of chemical types and structural forms of nucleic acid can be suitable for such strategies. These include, by way of non-limiting example, DNA, including single-stranded (ssDNA) and double-stranded (dsDNA); RNA, including, but not limited to ssRNA, dsRNA, tRNA, mRNA, rRNA, enzymatic RNA; RNA:DNA hybrids, triplexed DNA (e.g., dsDNA in association with a short oligonucleotide), and the like.

In some embodiments of the present invention, the nucleic acid agent is between about 5 and 2000 nucleotides long. In some embodiments, the nucleic acid agent is at least about 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40 41, 42, 43, 44, 45, 46, 47, 48, 49, 50 or more nucleotides long. In some embodiments, the nucleic acid agent is less than about 2000, 1900, 1800, 1700, 1600, 1500, 1400, 1300, 1200, 1100, 1000, 900, 800, 700, 600, 500, 450, 400, 350, 300, 250, 200, 150, 100, 50, 45, 40, 35, 30, 25, 20 or fewer nucleotides long.

In some embodiments, a nucleic acid agent comprises a promoter and/or other sequences that regulate transcription. In some embodiments, a nucleic acid agent comprises an origin of replication and/or other sequences that regulate replication. In some embodiments, a nucleic acid agent does not include a promoter and/or an origin of replication.

Nucleic acid anti-cancer agents suitable for use in the practice of the present invention include those agents that target genes associated with tumorigenesis and cell growth or cell transformation (e.g., proto-oncogenes, which code for proteins that stimulate cell division), angiogenic/anti-angiogenic genes, tumor suppressor genes (which code for proteins that suppress cell division), genes encoding proteins associated with tumor growth and/or tumor migration, and suicide genes which induce apoptosis or other forms of cell death, especially suicide genes that are most active in rapidly dividing cells.

Examples of gene sequences associated with tumorigenesis and/or cell transformation include MLL fusion genes, BCR-ABL, TEL-AML1, EWS-FLI1, TLS-FUS, PAX3-FKHR, Bcl-2, AML1-ETO, AML1-MTG8, Ras, Fos PDGF, RET, APC, NF-1, Rb, p53, MDM2 and the like; overexpressed sequences such as multidrug resistance genes; cyclins; beta-Catenin; telomerase genes; c-myc, n-myc, Bcl-2, Erb-B1 and Erb-B2; and mutated sequences such as Ras, Mos, Raf, and Met. Examples of tumor suppressor genes include, but are not limited to, p53, p21, RB1, WT1, NF1, VHL, APC, DAP kinase, p16, ARF, Neurofibromin, and PTEN. Examples of genes that can be targeted by nucleic acid molecules useful in anti-cancer therapy include genes encoding proteins associated with tumor migration such as integrins, selectins and metalloproteinases; anti-angiogenic genes encoding proteins that promote the formation of new vessels such as Vascular Endothelial Growth Factor (VEGF) or VEGFr; anti-angiogenic genes encoding proteins that inhibit neovascularization such as endostatin, angiostatin, and VEGF-R2; and genes encoding proteins such as interleukins, interferon, fibroblast growth factor ($\alpha$-FGF and $\beta$-FGF), insulin-like growth factor (e.g., IGF-1 and IGF-2), Platelet-derived growth factor (PDGF), tumor necrosis factor (TNF), Transforming Growth Factor (e.g., TGF-$\alpha$ and TGF-$\beta$), Epidermal growth factor (EGF), Keratinocyte Growth Factor (KGF), stem cell factor and its receptor c-Kit (SCF/c-Kit) ligand, CD40L/CD40, VLA-4 VCAM-1, ICAM-1/LFA-1, hyalurin/CD44, and the like. As will be recognized by one skilled in the art, the foregoing examples are not exclusive.

Nucleic acids for use in accordance with the present invention may have any of a variety of activities including, for example, as anti-cancer or other therapeutic agents, probes, primers, etc. Nucleic acids may have enzymatic activity (e.g., ribozyme activity), gene expression inhibitory activity (e.g., as antisense or siRNA agents, etc), and/or other activities. Nucleic acids may be active themselves or may be vectors that deliver active nucleic acid agents (e.g., through replication and/or transcription of a delivered nucleic acid). For purposes of the present specification, such vector nucleic acids are considered "therapeutic agents" if they encode or otherwise deliver a therapeutically active agent, even if they do not themselves have therapeutic activity.

In certain embodiments, a chlorotoxin agent is administered in combination with and/or comprises a nucleic acid therapeutic agent that comprises or encodes an antisense compound. The terms "antisense compound or agent", "antisense oligomer", "antisense oligonucleotide", and "antisense oligonucleotide analog" are used herein interchangeably, and refer to a sequence of nucleotide bases and a subunit-to-subunit backbone that allows the antisense compound to hybridize to a target sequence in an RNA by Watson-Crick base pairing to form an RNA oligomer heteroduplex within the target sequence. The oligomer may have exact sequence complementarity within the target sequence or near complementarity. Such antisense oligomers may block or inhibit translation of the mRNA containing the target sequence, or inhibit gene transcription. Antisense oligomers may bind to double-stranded or single-stranded sequences.

Examples of antisense oligonucleotides suitable for use in the practice of the present invention include, for example, those mentioned in the following reviews: R. A Stahel et al., Lung Cancer, 2003, 41: S81-S88; K. F. Pirollo et al., Pharmacol. Ther., 2003, 99: 55-77; A. C. Stephens and R. P. Rivers, Curr. Opin. Mol. Ther., 2003, 5: 118-122; N. M. Dean and C. F. Bennett, Oncogene, 2003, 22: 9087-9096; N. Schiavone et al., Curr. Pharm. Des., 2004, 10: 769-784; L. Vidal et al., Eur. J. Cancer, 2005, 41: 2812-2818; T. Aboul-Fadl, Curr. Med. Chem., 2005, 12: 2193-2214; M. E. Gleave and B. P. Monia, Nat. Rev. Cancer, 2005, 5: 468-479; Y. S. Cho-Chung, Curr. Pharm. Des., 2005, 11: 2811-2823; E. Rayburn et al., Lett. Drug Design & Discov., 2005, 2: 1-18; E. R. Rayburn et al., Expert Opin. Emerg. Drugs, 2006, 11: 337-352; I. Tamm and M. Wagner, Mol. Biotechnol., 2006, 33: 221-238 (each of which is incorporated herein by reference in its entirety).

Examples of suitable antisense oligonucleotides include, for example olimerson sodium (also known as Genasense™ or G31239, developed by Genta, Inc., Berkeley Heights, N.J.), a phosphorothioate oligomer targeted towards the initiation codon region of the bcl-2 mRNA, which is a potent inhibitor of apoptosis and is overexpressed in many cancer including, follicular lymphomas, breast, colon and prostate cancers, and intermediate/high-grade lymphomas (C. A. Stein et al., Semin. Oncol., 2005, 32: 563-573; S. R. Frankel, Semin. Oncol., 2003, 30: 300-304). Other suitable antisense oligonucleotides include GEM-231 (HYB0165, Hybridon, Inc., Cambridge, Mass.), which is a mixed backbone oligonucleotide directed against cAMP-dependent protein kinase A (PKA) (S. Goel et al., Clin. Cancer Res., 203, 9: 4069-4076); Affinitak (ISIS 3521 or aprinocarsen, ISIS pharmaceuticals, Inc., Carlsbad, Calif.), an antisense inhibitor of PKC-alpha; OGX-011 (Isis 112989, Isis Pharmaceuticals, Inc.), a 2'-methoxyethyl modified antisense oligonucleotide against clusterin, a glycoprotein implicated in the regulation of the cell cycle, tissue remodeling, lipid transport and cell death and which is overexpressed in cancers of breast, prostate and colon; ISIS 5132 (Isis 112989, Isis Pharmaceuticals, Inc.), a phosphorothioate oligonucleotide complementary to a sequence of the 3'-unstranslated region of the c-raf-1 mRNA (S. P. Henry et al., Anticancer Drug Des., 1997, 12: 409-420; B. P. Monia et al., Proc. Natl. Acad. Sci. USA, 1996, 93: 15481-15484; C. M. Rudin et al., Clin. Cancer Res., 2001, 7: 1214-1220); ISIS 2503 (Isis Pharmaceuticals, Inc.), a phosphorothioate oligonucleotide antisense inhibitor of human H-ras mRNA expression (J. Kurreck, Eur. J. Biochem., 2003, 270: 1628-1644); oligonucleotides targeting the X-linked inhibitor of apoptosis protein (XIAP), which blocks a substantial portion of the apoptosis pathway, such as GEM 640 (AEG 35156, Aegera Therapeutics Inc. and Hybridon, Inc.) or targeting survivin, an inhibitor of apoptosis protein (IAP), such as ISIS 23722 (Isis Pharmaceuticals, Inc.), a 2'-O-methoxyethyl chimeric oligonucleotide; MG98, which targets DNA methyl transferase; and GTI-2040 (Lorus Therapeutics, Inc. Toronto, Canada), a 20-mer oligonucleotide that is complementary to a coding region in the mRNA of the R2 small subunit component of human ribonucleotide reductase.

Other suitable antisense oligonucleotides include antisense oligonucleotides that are being developed against Her-2/neu, c-Myb, c-Myc, and c-Raf (see, for example, A. Biroccio et al., Oncogene, 2003, 22: 6579-6588; Y. Lee et al., Cancer Res., 2003, 63: 2802-2811; B. Lu et al., Cancer Res., 2004, 64: 2840-2845; K. F. Pirollo et al., Pharmacol. Ther., 2003, 99: 55-77; and A. Rait et al., Ann. N.Y. Acad. Sci., 2003, 1002: 78-89).

In certain embodiments, nucleic acid anti-cancer agent for use in accordance with the present invention comprises or encodes an interfering RNA molecule. The terms "interfering RNA" and "interfering RNA molecule" are used herein interchangeably, and refer to an RNA molecule that can inhibit or downregulate gene expression or silence a gene in a sequence-specific manner, for example by mediating RNA interference (RNAi). RNA interference (RNAi) is an evolutionarily conserved, sequence-specific mechanism triggered by double-stranded RNA (dsRNA) that induces degradation of complementary target single-stranded mRNA and "silencing" of the corresponding translated sequences (McManus and Sharp, 2002, Nature Rev. Genet., 2002, 3: 737). RNAi functions by enzymatic cleavage of longer dsRNA strands into biologically active "short-interfering RNA" (siRNA) sequences of about 21-23 nucleotides in length (Elbashir et al., Genes Dev., 2001, 15: 188). RNA interference has emerged as a promising approach for therapy of cancer.

An interfering RNA suitable for use in the practice of the present invention can be provided in any of several forms. For example, an interfering RNA can be provided as one or more of an isolated short interfering RNA (siRNA), double-stranded RNA (dsRNA), micro-RNA (miRNA), or short hairpin RNA (shRNA).

Examples of interfering RNA molecules suitable for use in the present invention include, for example, the iRNAs cited in the following reviews: O. Milhavet et al., Pharmacol. Rev., 2003, 55: 629-648; F. Bi et al., Curr. Gene. Ther., 2003, 3: 411-417; P. Y. Lu et al., Curr. Opin. Mol. Ther., 2003, 5: 225-234; I. Friedrich et al., Semin. Cancer Biol., 2004, 14: 223-230; M. Izquierdo, Cancer Gene Ther., 2005, 12: 217-227; P. Y. Lu et al., Adv. Genet., 2005, 54: 117-142; G. R. Devi, Cancer Gene Ther., 2006, 13: 819-829; M. A. Behlke, Mol. Ther., 2006, 13: 644-670; and L. N. Putral et al., Drug News Perspect., 2006, 19: 317-324 (each of which is incorporated herein by reference in its entirety).

Other examples of suitable interfering RNA molecules include, but are not limited to, p53 interfering RNAs (e.g., T. R. Brummelkamp et al., Science, 2002, 296: 550-553; M. T. Hemman et al., Nat. Genet., 2003, 33: 396-400); interfering RNAs that target the bcr-abl fusion, which is associated with development of chronic myeloid leukemia and acute lymphoblastic leukemia (e.g., M. Scherr et al., Blood, 2003, 101: 1566-1569; M. J. Li et al., Oligonucleotides, 2003, 13: 401-409), interfering RNAs that inhibit expression of NPM-ALK, a protein that is found in 75% of anaplastic large cell lymphomas and leads to expression of a constitutively active kinase associated with tumor formation (U. Ritter et al., Oligonucleotides, 2003, 13: 365-373); interfering RNAs that target oncogenes, such as Raf-1 (T. F. Lou et al., Oligonucleotides, 2003, 13: 313-324), K-Ras (T. R. Brummelkamp et al., Cancer Cell, 2002, 2: 243-247), erbB-2 (G. Yang et al., J. Biol. Chem., 2004, 279: 4339-4345); interfering RNAs that target b-catenin protein, whose over-expression leads to transactivation of the T-cell factor target genes, which is thought to be the main transforming event in colorectal cancer (M. van de Wetering et al., EMBO Rep., 2003, 4: 609-615).

In some embodiments, chlorotoxin agents as described herein are administered in combination with or as part of a therapeutic regimen with one or more therapeutic regimens recommended for treatment of a disease, disorder, or condition associated with angiogenesis. To give but a few examples, recommended regimens for treatment of cancer can be found at the web site have a URL of www.cancer.gov, the website of the National Cancer Institute. Recommended regimens for treatment of macular degeneration can be found at the web site having URL www.mayoclinic.org/macular-degeneration/treatment.html. Treatment regimens may include chemotherapy, surgery, and/or radiation therapy.

C. Labeling Moieties

In certain embodiments, a chlorotoxin agent is labeled with at least one labeling moiety. For example, one or more chlorotoxin moieties and/or one or more therapeutic moieties may be labeled with a labeling moiety.

A labeling moiety may facilitate detection of the chlorotoxin agent after binding to the tissue to be tested. The labeling moiety may be selected such that it generates a signal that can be measured and whose intensity is related to (e.g., proportional to) the amount of diagnostic agent bound to the tissue.

In some embodiments, labeling does not substantially interfere with the desired biological or pharmaceutical activity of the chlorotoxin agent. In certain embodiments, labeling involves attachment or incorporation of one or more labeling moieties to a chlorotoxin moiety, for example, to non-interfering positions on the peptide sequence of the chlorotoxin moiety. Such non-interfering positions are positions that do not participate in the specific binding of the chlorotoxin moiety to tumor cells.

A labeling moiety may be any entity that allows detection of achlorotoxin agent after binding to a tissue or system of interest. Any of a wide variety of detectable agents can be used as labeling moieties in chlorotoxin agents of the present invention. A labeling moiety may be directly detectable or indirectly detectable. Examples of labeling moieties include, but are not limited to: various ligands, radionuclides (e.g., $^{3}H$, $^{14}C$, $^{18}F$, $^{19}F$, $^{32}P$, $^{35}S$, $^{135}I$, $^{125}I$, $^{123}I$, $^{64}Cu$, $^{187}Re$, $^{111}In$, $^{90}Y$, $^{99m}Tc$, $^{177}Lu$, etc.), fluorescent dyes (for specific exemplary fluorescent dyes, see below), chemiluminescent agents (such as, for example, acridinum esters, stabilized dioxetanes, and the like), bioluminescent agents, spectrally resolvable inorganic fluorescent semiconductors nanocrystals (i.e., quantum dots), metal nanoparticles (e.g., gold, silver, copper, platinum, etc.) nanoclusters, paramagnetic metal ions, enzymes (for specific examples of enzymes, see below), colorimetric labels (such as, for example, dyes, colloidal gold, and the like), biotin, dioxigenin, haptens, and proteins for which antisera or monoclonal antibodies are available.

In certain embodiments, a labeling moiety comprises a fluorescent label. Numerous known fluorescent labeling moieties of a wide variety of chemical structures and physical characteristics are suitable for use in the practice of methods of diagnosis of the present invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, Spectrum Red™, Spectrum Green™, cyanine dyes (e.g., Cy-3™, Cy-5™, Cy-3.5™, Cy-5.5™, etc.), Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660, Alexa Fluor 680, etc.), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "*The Handbook of Fluorescent Probes and Research Products*", 9$^{th}$ Ed., Molecular Probes, Inc., Eugene, Oreg. Favorable properties of fluorescent labeling agents include high molar absorption coefficient, high fluorescence quantum yield, and photostability. In certain embodiments, labeling fluorophores desirably exhibit absorption and emission wavelengths in the visible (i.e., between 400 and 750 nm) rather than in the ultraviolet range of the spectrum (i.e., lower than 400 nm).

In certain embodiments, a labeling moiety comprises an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a chlorotoxin moiety using a linker group such as a carbodiimide, a diisocyanate, a glutaraldehyde, and the like.

In certain embodiments, a labeling moiety comprises a radioisotope that is detectable by Single Photon Emission Computed Tomography (SPECT) or Position Emission Tomography (PET). Examples of such radionuclides include, but are not limited to, iodine-131 ($^{131}I$), iodine-125 ($^{125}I$), bismuth-212 ($^{212}Bi$), bismuth-213 ($^{213}Bi$), astatine-221 ($^{211}At$), copper-67 ($^{67}Cu$), copper-64 ($^{64}Cu$), rhenium-186 ($^{186}Re$), rhenium-186 ($^{188}Re$), phosphorus-32 ($^{32}P$), samarium-153 ($^{153}Sm$), lutetium-177 ($^{117}Lu$), technetium-99m ($^{99m}Tc$), gallium-67 ($^{67}Ga$), indium-111 ($^{111}In$), and thallium-201 ($^{201}Tl$).

In certain embodiments, a labeling moiety comprises a radioisotope that is detectable by Gamma camera. Examples of such radioisotopes include, but are not limited to, iodine-131 ($^{131}I$), and technetium-99m ($^{99m}Tc$).

In certain embodiments, a labeling moiety comprises a paramagnetic metal ion that is a good contrast enhancer in Magnetic Resonance Imaging (MRI). Examples of such paramagnetic metal ions include, but are not limited to, gadolinium III ($Gd^{3+}$), chromium III ($Cr^{3+}$), dysprosium III ($Dy^{3+}$), iron III ($Fe^{3+}$), manganese II ($Mn^{2+}$), and ytterbium III ($Yb^{3+}$). In certain embodiments, the labeling moieties comprises gadolinium III ($Gd^{3+}$). Gadolinium is an FDA-approved contrast agent for MRI, which accumulates in abnormal tissues causing these abnormal areas to become very bright (enhanced) on the magnetic resonance image. Gadolinium is known to provide great contrast between normal and abnormal tissues in different areas of the body, in particular in the brain.

In certain embodiments, a labeling moiety comprises a stable paramagnetic isotope detectable by nuclear magnetic resonance spectroscopy (MRS). Examples of suitable stable paramagnetic isotopes include, but are not limited to, carbon-13 ($^{13}C$) and fluorine-19 ($^{19}F$).

D. Associations Between Chlorotoxin Agents Therapeutic Agents and/or Labeling Moieties In certain embodiments, a chlorotoxin agent is moiety associated with at least a second therapeutic agent and/or labeling moiety.

Association between a chlorotoxin agent and a therapeutic agent and/or labeling moiety may be covalent or non-covalent. Irrespective of the nature of the binding, interaction, or coupling, the association between a chlorotoxin agent and a therapeutic agent is, in some embodiments, selective, specific and strong enough so that the second therapeutic agent does not dissociate from the chlorotoxin agent before or during transport/delivery to and into the tumor. Association between a chlorotoxin agent and a second therapeutic agent may be achieved using any chemical, biochemical, enzymatic, or genetic coupling known to one skilled in the art.

In certain embodiments, association between a chlorotoxin agent and a therapeutic agent and/or labeling moiety is non-covalent. Examples of non-covalent interactions include, but are not limited to, hydrophobic interactions, electrostatic interactions, dipole interactions, van der Waals interactions, and hydrogen bonding.

In certain embodiments, association between a chlorotoxin agent and a therapeutic agent and/or labeling moiety is covalent. As will be appreciated by one skilled in the art, the moieties may be attached to each other either directly or indirectly (e.g., through a linker, as described below).

In certain embodiments, a chlorotoxin agent and therapeutic agent and/or labeling moiety are directly covalently linked to each other. Direct covalent binding can be through a linkage such as an amide, ester, carbon-carbon, disulfide, carbamate, ether, thioether, urea, amine, or carbonate linkage. Covalent binding can be achieved by taking advantage of functional groups present on the chlorotoxin agent and/or the therapeutic agent. Alternatively, a non-critical amino acid may be replaced by another amino acid that will introduce a useful group (amino, carboxy or sulfhydryl) for coupling purposes. Alternatively, an additional amino acid may be added to the chlorotoxin agent to introduce a useful group (amino, carboxy or sulfhydryl) for coupling purposes. Suitable functional groups that can be used to attach moieties together include, but are not limited to, amines, anhydrides, hydroxyl groups, carboxy groups, thiols, and the like. An activating agent, such as a carbodiimide, can be used to form a direct linkage. A wide variety of activating agents are known in the art and are suitable for linking a therapeutic agent and a chlorotoxin moiety.

In other embodiments, a chlorotoxin agent and a therapeutic agent and/or labeling moiety are indirectly covalently linked to each other via a linker group. This can be accomplished by using any number of stable bifunctional agents well known in the art, including homofunctional and heterofunctional agents (for examples of such agents, see, e.g., Pierce Catalog and Handbook). The use of a bifunctional linker differs from the use of an activating agent in that the former results in a linking moiety being present in the resulting chlorotoxin agent, whereas the latter results in a direct coupling between the two moieties involved in the reaction. The role of a bifunctional linker may be to allow reaction between two otherwise inert moieties. Alternatively or additionally, the bifunctional linker that becomes part of the reaction product may be selected such that it confers some degree of conformational flexibility to the chlorotoxin agent (e.g., the bifunctional linker comprises a straight alkyl chain containing several atoms, for example, the straight alkyl chain contains between 2 and 10 carbon atoms). Alternatively or additionally, the bifunctional linker may be selected such that the linkage formed between a chlorotoxin agent and therapeutic agent is cleavable, e.g. hydrolysable (for examples of such linkers, see e.g. U.S. Pat. Nos. 5,773,001; 5,739,116 and 5,877,296, each of which is incorporated herein by reference in its entirety). Such linkers, for example, may be used when higher activity of the chlorotoxin agent and/or of the therapeutic agent is observed after hydrolysis of the conjugate. Exemplary mechanisms by which a therapeutic agent may be cleaved from a chlorotoxin agent include hydrolysis in the acidic pH of the lysosomes (hydrazones, acetals, and cis-aconitate-like amides), peptide cleavage by lysosomal enzymes (the capthepsins and other lysosomal enzymes), and reduction of disulfides). Another mechanism by which a therapeutic agent is cleaved from the chlorotoxin agent includes hydrolysis at physiological pH extra- or intra-cellularly. This mechanism applies when the crosslinker used to couple the therapeutic agent to the chlorotoxin moiety is a biodegradable/bioerodible entity, such as polydextran and the like.

For example, hydrazone-containing chlorotoxin agents can be made with introduced carbonyl groups that provide the desired release properties. Chlorotoxin agents can also be made with a linker that comprise an alkyl chain with a disulfide group at one end and a hydrazine derivative at the other end. Linkers containing functional groups other than hydrazones also have the potential to be cleaved in the acidic milieu of lysosomes. For example, chlorotoxin agents can be made from thiol-reactive linkers that contain a group other than a hydrazone that is cleavable intracellularly, such as esters, amides, and acetals/ketals.

Another example of class of pH sensitive linkers are the cis-aconitates, which have a carboxylic acid group juxtaposed to an amide group. The carboxylic acid accelerates amide hydrolysis in the acidic lysosomes. Linkers that achieve a similar type of hydrolysis rate acceleration with several other types of structures can also be used.

Another potential release method for chlorotoxin agents is the enzymatic hydrolysis of peptides by the lysosomal enzymes. In one example, a peptidic toxin is attached via an amide bond to para-aminobenzyl alcohol and then a carbamate or carbonate is made between the benzyl alcohol and the therapeutic agent. Cleavage of the peptide leads to collapse of the amino benzyl carbamate or carbonate, and release of the therapeutic agent. In another example, a phenol can be cleaved by collapse of the linker instead of the carbamate. In another variation, disulfide reduction is used to initiate the collapse of a para-mercaptobenzyl carbamate or carbonate.

In embodiments where a therapeutic agent and/or labeling moiety is a protein, a polypeptide or a peptide, the chlorotoxin agent and the therapeutic agent may together form a fusion protein. As already defined above, a fusion protein is a molecule comprising two or more proteins or peptides linked by a covalent bond via their individual peptide backbones. Fusion proteins used in methods of the present invention can be produced by any suitable method known in the art. For example, they can be produced by direct protein synthetic methods using a polypeptide synthesizer. Alternatively, PCR amplification of gene fragments can be carried out using anchor primers which give rise to complementary overhangs between two consecutive gene fragments that can subsequently be annealed and re-amplified to generate a chimeric gene sequence. Fusion proteins can be obtained by standard recombinant methods (see, for example, Maniatis et al. "*Molecular Cloning: A Laboratory Manual*", $2^{nd}$ Ed., 1989, Cold Spring Harbor Laboratory, Cold Spring, N.Y.). These methods generally comprise (1) construction of a nucleic acid molecule that encodes the desired fusion protein; (2) insertion of the nucleic acid molecule into a recombinant expression vector; (3) transformation of a suitable host cell with the expression vector; and (4) expression of the fusion protein in the host cell. Fusion proteins produced by such methods may be recovered and isolated, either directly from the culture medium or by lysis of the cells, as known in the art. Many methods for purifying proteins produced by transformed host cells are well-known in the art. These include, but are not limited to, precipitation, centrifugation, gel filtration, and (ion-exchange, reverse-phase, and affinity) column chromatography. Other purification methods have been described (see, for example, Deutscher et al. "*Guide to Protein Purification*" in Methods in Enzymology, 1990, Vol. 182, Academic Press).

As can readily be appreciated by one skilled in the art, a chlorotoxin agent used in methods of the present invention can comprise any number of chlorotoxin moieties and be associated with any number of therapeutic agents and/or labeling moieties, associated to one another by any number of different ways. The design of a conjugate will be influenced by its intended purpose(s) and the properties that are desirable in the particular context of its use. Selection of a method to associate or bind a chlorotoxin moiety to a therapeutic agent to form a chlorotoxin agent is within the knowledge of one skilled in the art and will generally depend on the nature of the interaction desired between the moieties (i.e., covalent vs. non-covalent and/or cleavable vs. non-cleavable), the nature of the therapeutic agent, the presence and nature of functional chemical groups on the moieties involved and the like.

In labeled chlorotoxin agents, association between a chlorotoxin agent (or therapeutic agent) and a labeling moiety may be covalent or non-covalent. In case of covalent association, the chlorotoxin (or therapeutic) and labeling moieties may be attached to each other either directly or indirectly, as described above.

In certain embodiments, association between a chlorotoxin moiety (or therapeutic agent) and a labeling moiety is non-covalent. Examples of non-covalent associations include, but are not limited to, hydrophobic interactions, electrostatic interactions, dipole interactions, van der Waals interactions, and hydrogen bonding. For example, a labeling moiety can be non-covalently attached to a chlorotoxin agent (or therapeutic agent) by chelation (e.g., a metal isotope can be chelated to a polyHis region attached, e.g., fused, to a chlorotoxin moiety).

In certain embodiments, a chlorotoxin agent (or therapeutic agent) is isotopically labeled (i.e., it contains one or more atoms that have been replaced by an atom having an atomic mass or mass number different from the atomic mass or mass number usually found in nature). Alternatively or additionally, an isotope may be attached to a chlorotoxin agent and/or therapeutic agent.

As can readily be appreciated by one skilled in the art, a labeled chlorotoxin agent used in certain methods of the present invention can comprise any number of labeling moieties, and be associated with any number of therapeutic of agents. Such agents and labeling moieties can be associated to one another by any number of different ways. The design of a labeled chlorotoxin agent will be influenced by its intended purpose(s), the properties that are desirable in the context of its use, and the method selected from the detection.

II. Methods of Reducing Angiogenesis

Methods of reducing angiogenesis of the present invention often comprise administering an amount of chlorotoxin agent to a subject, wherein the amount of chlorotoxin is effective such that extent of angiogenesis is reduced as compared with that observed or expected for a control subject to whom chlorotoxin agent is not administered.

A. Indications

Methods of the invention may be useful for ameliorating and/or treating diseases or conditions involving aberrant angiogenesis. "Aberrant angiogenesis," as used herein refers to angiogenesis that does not occur in normal biological processes such as development, reproduction, wound healing etc. Angiogenesis that may be reduced using methods of the invention may be stimulated, in some embodiments, by a factor selected from the group consisting of vascular endothelial growth factor (VEGF), basic fibroblast growth factor (bFGF), lipopolysaccharide (LPS), epidermal growth factor (EGF), interleukin-6 (IL-6), platelet-derived growth factor (PDGF), tumor necrosis factor (TNFα), hepatocyte growth factor (HGF), and combinations thereof.

As angiogenesis is involved in a variety of pathologic processes, inventive methods may be useful in treating and/or ameliorating diseases such as, for example cancer (including metastatic cancer), ocular neovascularization (such as macular degeneration), inflammatory diseases (such as arthritis), etc.

Tumors often come to depend on the formation of new blood vessels in order to continue growing and/or develop metastases. Thus, inventive methods may be useful in ameliorating and/or treating tumors. Subjects that may be administered chlorotoxin agents may have tumors that are beginning to metastasize or have already metastasized. Subjects may have one or more metastases. In some embodiments, sizes of tumors and/or metastases are reduced.

In some embodiments, the subject is suffering from or at risk for a condition or disease characterized by choroidal neovascularization. Such conditions include, but are not limited to, macular degeneration, myopia, ocular trauma, pseudoxanthoma elasticum, and combinations thereof.

Macular degeneration is the leading cause of vision loss and blindness in Americans aged 65 and older. Macular degeneration typically occurs in the age-related form (often called AMD or ARMD), though juvenile macular degeneration occurs as well. In AMD/ARMD, the macula—the part of the retina that is responsible for sharp, central vision—degenerates. Macular degeneration is typically diagnosed as either dry (non-neovascular) or wet (neovascular).

In dry macular degeneration, yellowish spots known as drusen begin to accumulate from deposits or debris from deteriorating tissue from mostly around the macula. Central vision less usually occurs gradually and is not as severe as vision loss in wet macular degeneration.

Wet macular degeneration, as the "neovascular" designation suggests, is characterized by new blood vessels growing aberrantly, e.g., on the macula. Such new blood vessels may grow beneath the retina, leaking blood and fluid. Such leakage causes permanent damage to light-sensitive retinal cells, which die and create blind spots in central vision. Wet macular degeneration may be further grouped into two categories. In the occult form of wet macular degeneration, new blood vessel growth beneath the retina is not as pronounced and leakage is less evident, typically resulting in less severe vision less. In the classic form of wet macular degeneration, blood vessel growth and scarring have very clear, delineated outlines that are observable beneath the retina. Classic wet macular degeneration is also known as classic choroidal neovascularization and usually results in more severe vision loss.

Given the role of angiogenesis in wet macular degeneration, which comprises many AMD/ARMD cases, inventive methods may be useful in treating and/or ameliorating such disorders. Current therapies for wet macular degeneration involve angiogenesis inhibitors such as Lucentis™, Macugen™, and/or Visudyne™, optionally combined with photodynamic therapy (PDT) to target drugs to specific cells. Photocoagulation, in which a high energy laser beam is used to create small burns in areas of the retina ith abnormal blood vessels, is also used to treat wet macular degeneration.

In some embodiments, the subject suffers from wet macular degeneration and/or age-related macular degeneration. Among subjects suffering from wet macular degeneration, subjects may suffer from the occult or the classic form. In some embodiments, chlorotoxin agents cause regression of existing neovasculature. In some embodiments, chlorotoxin agents prevent sprouting of new vessels. In certain embodiments, chlorotoxin agents are combined with other treatments for wet macular degeneration, such as photocoagulation, treatment with other angiogenesis inhibitors, photodynamic therapy, etc.

B. Dosages and Administrations

In methods of the present invention, a chlorotoxin agent, or a pharmaceutical composition thereof, will generally be administered in such amounts and for such a time as is necessary or sufficient to achieve at least one desired result. For example, a chlorotoxin agent can be administered in such amounts and for such a time that it slows or inhibits the formation of blood vessels and/or causes the regression of existing neovasculature. Such effects may yield clinical benefits that may, for example, be detectable in other ways. For example, reduction of angiogenesis in a cancer patient may result in a reduction of tumor size, decrease in number of metastases, prevention of the formation of metastases, etc. Similarly, reduction of angiogenesis in a patient with macular degeneration may result in improvement in sight. As another example, in arthritis patients, reduce angiogenesis may decrease inflammation and relieve symptoms.

A dosing regimen according to the present invention may consist of a single dose or a plurality of doses over a period of time. Administration may be one or multiple times daily, weekly (or at some other multiple day interval) or on an intermittent schedule. The exact amount of a chlorotoxin agent, or pharmaceutical composition thereof, to be administered will vary from subject to subject and will depend on several factors (see below). As discussed in Example 7, modification of chlorotoxin agents by, for example, PEGylation may allow lower frequencies of administration while maintaining efficacy against angiogenesis. In some embodiments of the invention, chlorotoxin agents are administered fewer than five times per week. In some embodiments, chlorotoxin agents are administered fewer than two times per week.

Chlorotoxin agents, or pharmaceutical compositions thereof, may be administered using any administration route effective for achieving the desired therapeutic effect. In certain embodiments of the invention, chlorotoxin agents (or pharmaceutical compositions thereof) are delivered systemically. Typical systemic routes of administration include, but are not limited to, intramuscular, intravenous, pulmonary, and oral routes. Systemic administration may also be performed, for example, by infusion or bolus injection, or by absorption through epithelial or mucocutaneous linings (e.g., oral, mucosa, rectal and intestinal mucosa, etc). In certain embodiments, the chlorotoxin agent is administered intravenously.

Other routes of administration may also be used. In certain embodiments, the chlorotoxin agent is administered by a route selected from the group consisting of intravenous, intracranial, intramuscular, intratumoral, subcutaneous, intraocular, periocular, topical application, or by combinations thereof.

It may be desirable to reduce extent of angiogenesis in ocular neovascularization diseases. In some embodiments, chlorotoxin agents may be delivered to the eye. Delivery to the eye may be achieved, for example, using intraocular and/or periocular routes such as intravitreal injection, subconjunctival injection, etc. Topical application of chlorotoxin agents to the eye may also be achieved, for example, using eye drops.

Ocular routes of administration may be particularly useful for treatment of ocular neovascularization diseases such as macular degeneration.

Depending on the route of administration, effective doses may be calculated according to the body weight; body surface area; primary organ/tumor size; and/or number, sizes, and/or types of metastases of the subject to be treated. Optimization of the appropriate dosages can readily be made by one skilled in the art in light of pharmacokinetic data observed in human clinical trials. The final dosage regimen will be determined by the attending physician, considering various factors which modify the action of the drugs, e.g., the drug's specific activity, the severity of the damage and the responsiveness of the patient, the age, condition, body weight, sex and diet of the patient, the severity of any present infection, time of administration, the use (or not) of other therapies, and other clinical factors. As studies are conducted using chlorotoxin agents, further information will emerge regarding the appropriate dosage levels and duration of treatment.

Typical dosages comprise 1.0 pg/kg body weight to 100 mg/kg body weight. For example, for systemic administration, dosages may be 100.0 ng/kg body weight to 10.0 mg/kg body weight.

More specifically, in certain embodiments where a chlorotoxin agent is administered intravenously, dosing of the agent may comprise administration of one or more doses comprising about 0.005 mg/kg to about 5 mg/kg, e.g., from about 0.005 mg/kg to about 5 mg/kg, from about 0.01 mg/kg to about 4 mg/kg, from about 0.02 mg/kg to about 3 mg/kg, from about 0.03 mg/kg to about 2 mg/kg or from about 0.03 mg/kg to about 1.5 mg/kg of chlorotoxin. For example, in certain embodiments, one or more doses of chlorotoxin agent may be administered that each contains about 0.03 mg/kg, about 0.04 mg/kg, about 0.05 mg/kg, about 0.06 mg/kg, about 0.07 mg/kg, about 0.09 mg/kg, about 1.0 mg/kg or more than 1.0 mg/kg of chlorotoxin. In other embodiments, one or more doses of chlorotoxin agent may be administered that each contains about 0.05 mg/kg, about 0.10 mg/kg, about 0.15 mg/kg, about 0.20 mg/kg, about 0.25 mg/kg, about 0.30 mg/kg, about 0.35 mg/kg, about 0.40 mg/kg, about 0.45 mg/kg, about 0.50 mg/kg, about 0.55 mg/kg, about 0.60 mg/kg, about 0.65 mg/kg, about 0.70 mg/kg, about 0.75 mg/kg, about 0.80 mg/kg, about 0.85 mg/kg, about 0.90 mg/kg, about 0.95 mg/kg, about 1.0 mg/kg, or more than about 1 mg/kg of chlorotoxin. In yet other embodiments, one or more doses of chlorotoxin agent may be administered that each contains about 1.0 mg/kg, about 1.05 mg/kg, about 1.10 mg/kg, about 1.15 mg/kg, about 1.20 mg/kg, about 1.25 mg/kg, about 1.3 mg/kg, about 1.35 mg/kg, about 1.40 mg/kg, about 1.45 mg/kg, about 1.50 mg/kg, or more than about 1.50 mg/kg of chlorotoxin. In such embodiments, at treatment may comprise administration of a single dose of chlorotoxin agent or administration of 2 doses, 3 doses, 4 doses, 5 doses, 6 doses or more than 6 doses. Two consecutive doses may be administered at 1 day interval, 2 days interval, 3 days interval, 4 days interval, 5 days interval, 6 days interval, 7 days interval, or more than 7 days interval (e.g., 10 days, 2 weeks, or more than 2 weeks).

C. Extent of Angiogenesis

In inventive methods of reducing angiogenesis, extent of angiogenesis may be determined in comparison to a control. As is understood by those of ordinary skill in the art, control levels may be obtained and/or estimated in a variety of ways. Data from control subjects that are similar to the subject being administered may be used for comparisons. Alternatively or additionally, standard values may be used as control values. Such standard values may be calculated and/or extrapolated from known data, values, parameters, etc., which may be available, for example, in clinical records, archives, literature, etc.

Extent of angiogenesis may be measured in a variety of ways. For example, hemoglobin content, area of neovascularization, number of branch points counted in a given field of view, etc. may serve as indicia of extent of angiogenesis.

Clinical readouts such as number of metastases (for example, in cancer patients), vision scores (for example, in subjects suffering from ocular neovascularization diseases), etc. may also serve as measures of extent of angiogenesis.

In some embodiments, extent of angiogenesis is reduced by at least 50% as compared to the control subject.

D. Combination Therapies

It will be appreciated that methods of the present invention can be employed in combination with additional therapies (i.e., a treatment according to the present invention can be administered concurrently with, prior to, or subsequently to one or more desired therapeutics or medical procedures). The particular combination of therapies (therapeutics or procedures) to employ in such a combination regimen will take into account compatibility of the desired therapeutics and/or procedures and the desired therapeutic effect to be achieved.

For example, for reducing angiogenesis in cancer, methods of the present invention can be employed together with other procedures including surgery, radiotherapy (e.g., γ-radiation, neuron beam radiotherapy, electron beam radiotherapy, proton therapy, brachytherapy, systemic radioactive isotopes), endocrine therapy, hyperthermia, and cryotherapy, depending on the tumor to be treated.

In many cases of metastatic brain tumor, a method of the present invention will often be administered after surgery to remove the primary tumor. In the treatment of brain tumor, the main goal of surgery is to achieve a gross-total resection, i.e., removal of all visible primary tumor. One of the difficulties in achieving such a goal is that these tumors are infiltrative, i.e., they tend to weave in and out among normal brain structures. Furthermore, there is a great variability in the amount of tumor that can be safely removed from the brain of a patient. Removal is generally not possible if all or part of the tumor is located in a region of the brain controlling critical functions. Furthermore, it may not be possible or practical to remove and/or destroy metastases at distant sites with surgery alone.

In many cases of metastatic brain tumor, a treatment of the present invention will often be administered in combination with (i.e., concurrently with, prior to, or subsequently to) radiotherapy. In conventional treatments, radiotherapy generally follows surgery. Radiation is generally given as a series of daily treatments (called fractions) over several weeks. This "fractionated" approach to administering radiation is important to maximize the destruction of tumor cells and minimize side effects on normal adjacent brain. The area over which the radiation is administered (called the radiation field) is carefully calculated to avoid including as much of normal brain as is feasible.

Alternatively or additionally, methods of the present invention can be administered in combination with other therapeutic agents, such as agents that attenuate any adverse effects (e.g., antiemetics, etc.) and/or with other approved chemotherapeutic drugs. Examples of chemotherapeutics include, but are not limited to, alkylating drugs (e.g., mechlorethamine, chlorambucil, cyclophosphamide, melphalan, ifosfamide, etc.), antimetabolites (e.g., methotrexate, etc.), purine antagonists and pyrimidine antagonists (e.g., 6-mercaptopurine, 5-fluorouracil, cytarabine, gemcitabine, etc.), spindle poisons (e.g., vinblastine, vincristine, vinorelbine, paclitaxel, etc.), podophyllotoxins (e.g., etoposide, irinotecan, topotecan, etc.), antibiotics (e.g., doxorubicin, bleomycin, mitomycin, etc.), nitrosureas (e.g., carmustine, lomustine, nomustine, etc.), inorganic ions (e.g., cisplatin, carboplatin, etc.), enzymes (e.g., asparaginase, etc.), and hormones (e.g., tamoxifen, leuprolide, flutamide, megestrol, etc.), to name a few. For a more comprehensive discussion of updated cancer therapies see, http://www.cancer.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Methods of the present invention can also be employed together with one or more further combinations of cytotoxic agents as part of a treatment regimen, wherein the further combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine); ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChlVPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP(B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylpredisolone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP(B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

As will be appreciated by one skilled in the art, the selection of one or more therapeutic agents to be administered in combination with a method of treatment of the present invention will depend on the metastatic tumor to be treated.

For example, chemotherapeutic drugs prescribed for brain tumors include, but are not limited to, temozolomide (Temodar®), procarbazine)(Matulane®, and lomustine (CCNU), which are taken orally; vincristine (Oncovin® or Vincasar PFS®), cisplatin (Platinol®), carmustine (BCNU, BiCNU), and carboplatin (Paraplatin®), which are administered intravenously; and mexotrexate (Rheumatrex® or Trexall®), which can be administered orally, intravenously or intrathecally (i.e., injected directly into spinal fluid). BCNU is also given under the form of a polymer wafer implant during surgery (Giadel® wafers). One of the most commonly prescribed combination therapy for brain tumors is PCV (procarbazine, CCNU, and vincristine) which is usually given every six weeks.

In embodiments where the tumor to be treated is a brain tumor of neuroectodermal origin, a method of the present invention may be used in combination with agents for the management of symptoms such as seizures and cerebral edema. Examples of anticonvulsants successfully administered to control seizures associated with brain tumors include, but are not limited to, phenyloin (Dilantin®), Carbamazepine (Tegretol®) and divalproex sodium (Depakote®). Swelling of the brain may be treated with steroids (e.g., dexamethasone (Decadron®).

D. Pharmaceutical Compositions

As mentioned above, methods of reducing extent of angiogenesis of the present invention include administration of a chlorotoxin agent per se or in the form of a pharmaceutical composition. A pharmaceutical composition will generally comprise an effective amount of at least one chlorotoxin agent and at least one pharmaceutically acceptable carrier or excipient.

Pharmaceutical compositions may be formulated using conventional methods well-known in the art. The optimal pharmaceutical formulation can be varied depending upon the route of administration and desired dosage. Such formulations may influence the physical state, stability, rate of in vivo release, and rate of in vivo clearance of the administered compounds. Formulation may produce solid, liquid or semi-liquid pharmaceutical compositions.

Pharmaceutical compositions may be formulated in dosage unit form for ease of administration and uniformity of dosage. The expression "unit dosage form", as used herein, refers to a physically discrete unit of chlorotoxin agent for the patient to be treated. Each unit contains a predetermined quantity of active material calculated to produce the desired therapeutic effect. It will be understood, however, that the total dosage of the composition will be decided by the attending physician within the scope of sound medical judgment.

As mentioned above, in certain embodiments, the chlorotoxin agent is administered intravenously through injection or infusion. Pharmaceutical compositions suitable for administration by injection or infusion may be formulated according to the known art using suitable dispersing or wetting agents, and suspending agents. The pharmaceutical composition may also be a sterile injectable solution, suspension or emulsion in a non-toxic diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspension medium. For this purpose, any bland fixed oil can be used including synthetic mono- or di-glycerides. Fatty acids such as oleic acid may also be used in the preparation of injectable formulations.

Injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from injection. This may be accomplished by dissolving or suspending the active ingredient in an oil vehicle. Injectable depot forms are made by forming micro-encapsulated matrices of the drug in biodegradable polymers such as polylactide-polyglycolide. Depending on the ratio of drug to polymer and the nature of the particular polymer employed, the rate of drug release can be controlled. Depot injectable formulations can also be prepared by entrapping the drug in liposomes or microemulsions that are compatible with body tissues.

As discussed herein, modifications to chlorotoxin agents (such as, for example, covalent bonding to polymers) may be used to increase bioavailability of chlorotoxin agents.

III. Binders and Modulators of Annexin A2

Annexin A2 (also known as annexin II, ANX2, lipocortin, etc.) can be found docked to cell membranes at surfaces of epithelial cells. Annexin A2 has been implicated in a wide range of roles, including cell growth regulation, signal transduction pathways, and plasmin generation. Annexin A2 has been shown to be overexpressed in cancer cells.

Data presented herein support a role for Annexin A2 as a binding partner for chlorotoxin. Given chlorotoxin's anti-angiogenic and anti-tumor effects (established herein and in the art), its potential interaction with Annexin A2 is especially interesting. Annexin A2 promotes generation of plasmin (a serine protease) on endothelial cells. This action may be mediated by Annexin A2 binding to tPA (tissue plasminogen activator) and to plasminogen. Plasmin overproduction has been linked to angiogenesis and metastasis. At the same time, plasmin-cleaved $\beta$-2-Glycoprotein 1 has been observed to inhibit angiogenesis.

Data presented herein provide an interesting link between chlorotoxin's observed effects on angiogenesis and its potential binding partner.

Identification of Annexin A2 as a potential interaction partner for chlorotoxin validates Annexin A2 as a target for developing novel therapies. Agents that bind to and/or modulate Annexin A2, as chlorotoxin potentially does, may serve as useful therapeutic agents. Screening for such modulators may uncover new therapies, some of which may have different characteristics than chlorotoxin. Such new therapies may allow, for example, treatment and/or amelioration of a broader range of diseases, targeting to different cell types, dosing via different regimens and routes of administration, etc.

In certain embodiments, methods of identifying agents that bind to Annexin A2 are provided. Such agents may be useful in developing additional therapies, for example, for angiogenesis-related disorders. Such methods typically comprise steps of providing a sample comprising cells that express Annexin A2; contacting the sample with a test agent; determining whether the test agent binds to Annexin A2; and identifying, based on the determination, the test agent as an agent that binds to Annexin A2. In some embodiments, a further step of determining whether the test agent modulates Annexin A2 function is performed.

In certain embodiments, provided are methods of modulating Annexin A2 activity in a cell that expresses Annexin A2, comprising contacting the cell with an agent that modulates Annexin A2 such that Annexin A2 activity is altered.

Any of a variety of test agents may be used in accordance with inventive methods. Small molecules (such as, for example, those that can be found in compound libraries) can be screened in parallel assays, and those that bind to Annexin A2 and/or modulate Annexin A2 activity can be identified. Compound libraries such as those from historical collections of compounds and/or libraries from diversity-oriented syntheses may be suitable for use in inventive methods.

Alternatively or additionally, chlorotoxin fragments, derivatives, and/or variants may be screened using inventive methods to identify chlorotoxin fragments, derivatives, and/or variants having certain novel and/or desired characteristics. As another example, other toxins and fragments, derivatives, and variants thereof may be tested for ability to bind to and/or modulcate Annexin A2. Related scorpion toxins have been discussed herein.

Activities of Annexin A2 that may be modulated may involve, in some embodiments, regulation of the plasminogen/plasmin activator system. For example, Annexin A2 interacts with plasminogen and tPA (tissue plasminogen activator) and is involved in plasmin generation.

In some embodiments, Annexin A2 activity comprises binding to certain binding partners. Known binding partners of Annexin A2 include, but are not limited to, plasminogen, tPA (tissue plasminogen activator), S100A10 (S100 calcium binding protein A10, also known as calpactin light chain and annexin II light chain), F-actin, $\beta_2$-glycoprotein I, phospholipase A2, and Rac-1 containing complexes.

In some embodiments, Annexin A2 activity comprises localization to cell membrane surfaces, localization to endothelian cells, localization to calcium-dependent phospholipid membranes, localization at endothelial adherens junctions, localization at epithelial adherens junctions, localization at F-actin assembly platforms, and/or localization to endosomes.

In some embodiments, Annexin A2 activity comprises cell growth regulation, signal transduction. In some embodiments, Annexin A2 activity comprises suppression of phospholipase A2.

Annexin A2 is also thought to be involved in certain functions inside the cell. In some embodiments, Annexin A2 activity comprises involvement in actin assembly, sorting endosomes, stabilizing membrane domains, or combinations thereof.

Annexin A2 is also suspected or known to have certain functions outside the cell as well. Such activities include involvement in anticoagulant reactions (likely through its effect as a mediator of the plasmin/plasminogen activator system) and action as an autocrine factor involved in osteoclast formation and bone resorption.

EXAMPLES

The following examples describe some of the modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Anti-Angiogenic Activity of Chlorotoxin in the Chick Chorioallantoic Membrane (CAM) Assay The present Example demonstrates that TM-601 (a synthetic form of chlorotoxin) has a dose-dependent inhibitory effect on angiogenesis. In a chick chorioallantoic membrane (CAM) assay, pro-angiogenic factors (vascular endothelial growth factor (VEGF), basic fibroblast growth factor (bFGF), lipolysaccharide (LPS), epidermal growth factor (EGF), IL-6, platelet-derived growth factor (PDGF), tumor necrosis factor (TNFα) and hepatocyte growth factor (HGF) were tested in combination with TM-601. TM-601 inhibited angiogenesis stimulated by each of these factors in dose-dependent manner.

Materials and Methods

The CAM assay was performed as published previously. (See, e.g., Mousa S. S. et al. Effect of resveratrol on angiogenesis and platelet/fibrin-accelerated tumor growth in the chick chorioallantoic membrane model. *Nutrition and Cancer.* 2005; 52(1): 59-65, the contents of which are herein incorporated by reference in their entirety.) Fertilized chick eggs were incubated at 37° C. with 55% humidity. Ten days after fertilization, a small hole was created by puncturing with a hypodermic needle in the area of the shell concealing the air sac. A second hole was punctured in the shell on the broadside of the egg directly over an avascular portion of the embryonic membrane. A false air sac was created beneath the second hole by applying negative pressure to the first hole, which caused the membrane to separate from the shell. A window of approximately 1.0 cm$^2$ in area was cut in the shell over the dropped CAM using a small grinding wheel, allowing direct access to the underlying CAM. Filter disks were soaked in 3 mg/mL cortisone acetate and subsequently air dried under sterile conditions.

Each experiment involved a negative control (PBS), a positive control (pro-angiogenic factor), and treatment groups with a pro-angiogenic factor and TM-601 at different doses. Sterile filter disks with VEGF (2 μg/mL), bFGF (1 μg/mL), LPS (5 μg/mL), EGF (100 μg/mL)) IL-6 (10 μg/mL), PDGF (10 μg/mL), TNFα (10 μg/mL) or HGF (10 μg/ml) were placed on the growing CAMs. At 24 hours, TM-601 (0.001-100 μg) or the control vehicle was added topically to the CAMs. CAMs were harvested on the third day of stimulation. CAM tissue directly beneath the filter disk was removed from the embryos and tissues were washed three times with PBS. Blood vessel branch points in the 5-mm filter disk area were counted at 30× magnification as a quantitative indicator of vascular sprouting operators and the average reading was reported. The following equation was used to calculate the mean percent angiogensis inhibition with VEGF-stimulation:

$$\text{Mean \% inhibition} = \frac{(\text{\# branch points for } \textit{VEGF}) - (\text{\# branch points for } \textit{TM-}601)}{(\text{\# branch points for } \textit{VEGF}) - (\text{\# branch points for } \textit{PBS})} \quad \text{(Eq. 1)}$$

The experiments were designed to have eight eggs per group. However, due to technical reasons, fewer evaluable eggs remained in most experimental groups. In addition, the bFGF experiment was performed in two separate experiments, each with their own saline controls and positive bFGF control. This data was pooled to show the dose-dependent inhibitory effect across the concentration range of TM-601.

Results

Figure 2:
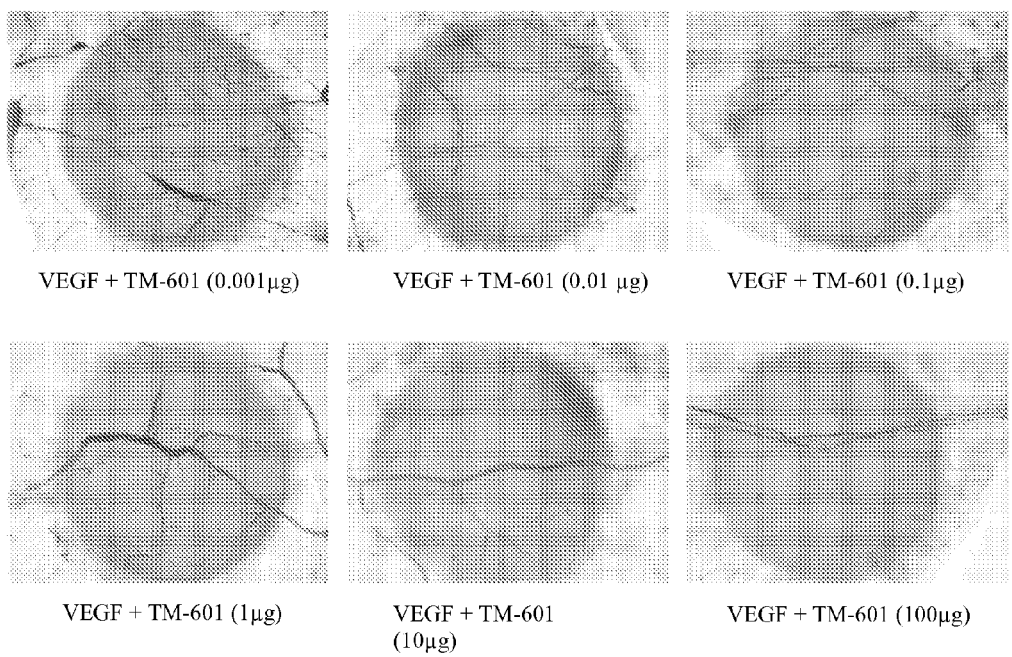
FIG. 2 depicts photographs showing that synthetic chlorotoxin (TM-601) inhibits VEGF-stimulated angiogenesis in a dose-dependent manner. Numbers of vascular branch points decreased as doses of TM-601 increased.
Figure 3:
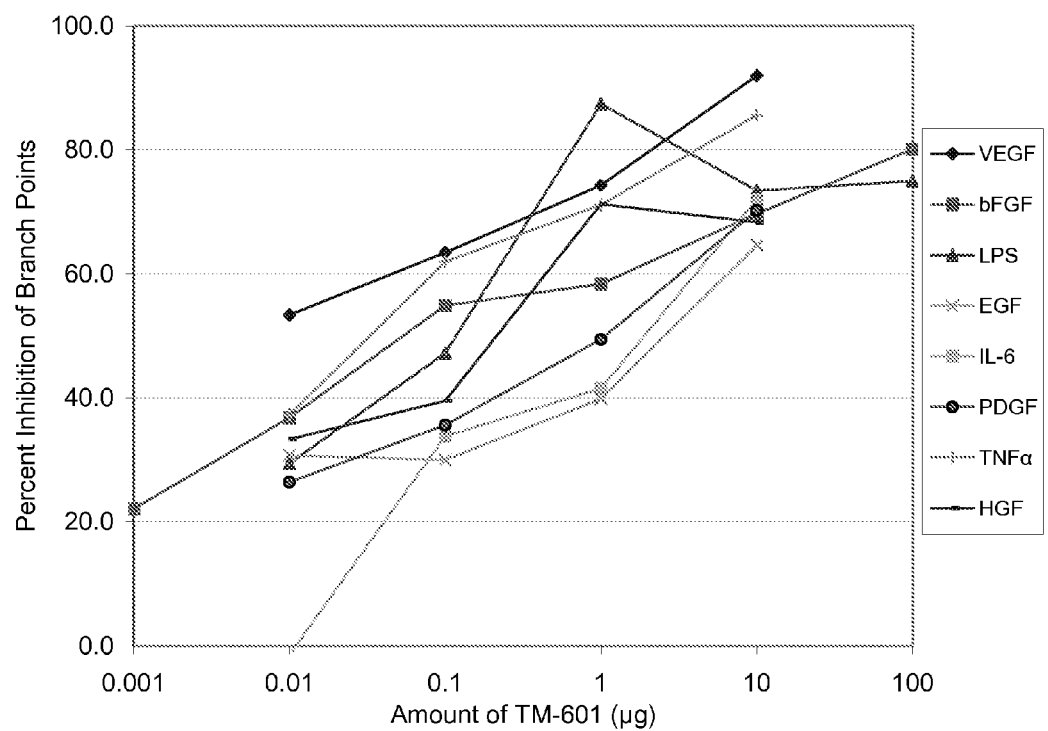
FIG. 3 depicts plots showing the inhibitory effect of TM-601 on angiogenesis stimulated by a various pro-angiogenic factors (VEGF, bFGF, LPS, EGF, IL-6, PDGF, TNFα, and HGF). Percent inhibition of branch points was plotted against concentrations of TM-601 for each factor.

Each of the pro-angiogenic factors strongly stimulated angiogenesis in the CAM assay (FIG. 1). Quantitative measurements of the number of vascular branch points was used to assess angiogenic sprouting. Percent inhibition of neovascularization was calculated at each test article dose. TM-601 was a potent inhibitor of angiogenesis in a dose-dependent manner for each of the pro-angiogenic compounds tested (VEGF, bFGF, LPS, EGF, IL-6, PDGF, TNFα, and HGF) (FIGS. 2 and 3). Such broad spectrum inhibition of angiogenesis is unlike many other angiogenesis inhibitors. Known angiogenesis inhibitors typically inhibit only one part or a subset of pathways involved in angiogenesis and are not effective against tumors that can adapt and/or use other signaling pathways.

The maximum observed inhibitory effect of TM-601 on bFGF, LPS, or EGF-stimulated angiogenesis was approximately 75-85% for the dose range tested. The maximum observed inhibitory effect of TM-601 on IL-6, PDGF, TNFα, or HGF-stimulated angiogenesis was approximately 65-75% for the dose rage tested. Without wishing to be bound by any particular theory, the inventors speculate that a greater inhibitory effect by TM-601 would be observed with even higher doses of TM-601.

Discussion/Conclusion

The CAM assay has been used to test whether TM-601 has anti-angiogenic activity. TM-601 was shown to have a potent inhibitory effect on angiogenesis stimulated with different pro-angiogenic compounds Inhibition of VEGF-stimulated and EGF-stimulated angiogenesis appeared to have the strongest effect, reaching greater than 90% inhibition at the highest dose tested. Inhibition of VEGF-stimulated angiogenesis reached greater than 50% inhibition even at doses as low as 0.001 μg.

Inhibitory effects of TM-601 on LPS-stimulated angiogenesis was tested. LPS is a major component of the outer membrane of Gram-negative bacteria. LPS induces a strong immune response and also directly induces angiogenesis. (See, e.g., Pollet et al. Bacterial lipopolysaccharide directly induces angiogenesis through TRAF6-mediated activation of NF-κB and c-Jun N-terminal kinase. *Blood.* 2003. 102(5): 1740-2, the entire contents of which are herein incorporated by reference in their entirety.) TM-601 was found also to block angiogenesis stimulated by LPS.

Although each of the pro-angiogenic compounds test bind to different receptors, some share downstream signaling pathways. For example, VEGF, bFGF, and LPS all signal through the p38 MAPK and the ERK1/2 pathways.

Example 2

Anti-Angiogenic Activity of TM-601 as Measured by an In Vivo Matrigel Plug Assay The experiments described in the present Example tested the ability of TM-601 delivered by various administration routes to inhibit angiogenesis in an in vivo matrigel plug assay in mice. TM-601 delivered systemically (10 mg/kg TM-601 via three intravenous injections per week) significantly decreased the formation of new blood vessels, whereas TM-601 delivered locally (i.e. by mixing TM-601 into the matrigel) or via subcutaneous injections (10 mg/kg TM-601 injected daily) did not. Subjects in experimental groups were not observed to have lost any weight, consistent with the idea that TM-601 treatments did not produce severe toxicity. Without wishing to be bound by any particular theory, the inventors propose that the results of these experiments suggest that the route of administration of chlorotoxin may have an effect on anti-angiogenesis ability.

Materials and Methods

Matrigel Matrix High Concentration (from BD Biosciences) was mixed with 100 ng/mL VEGF, 100 ng/mL bFGF, and 3 ng/mL heparin at 4° C. Eight-week old female C57BL/6. were randomly assigned to 5 groups with 5 mice in each group. The experimental design of the study is shown in Table 1.

TABLE 1

Experimental design for mouse matrigel plug experiments

| Group | # Animals | Treatment | Route | Dose | Route/Schedule |
|---|---|---|---|---|---|
| 1 | 5 | none | — | — | — |
| 2 | 5 | TM-601 | in matrigel | 500 ug/plug | — |
| 3 | 5 | TM-601 | in matrigel | 5 ug/plug | — |
| 4 | 5 | TM-601 | i.v. | 10 mg/kg | 3× per week |
| 5 | 5 | TM-601 | s.c. | 10 mg/kg | 7× per week | i.v. = intravenous;
s.c. = subcutaneous

One group of mice was implanted with matrigel as described above to serve as a positive control. The second and third groups of mice were implanted with matrigel that had TM-601 added to the matrigel before implantation. Mice in group two were each implanted with plugs containing 500 μg TM-601 per plug; mice in group three were each implanted with plugs containing 5 μg TM-601 per plug. Mice in groups four and five were implanted with matrigel (without TM-601 added) and received doses of TM-601 throughout the study period at 10 mg/kg/injection given either three times per week intravenously or daily subcutaneously. Each mouse received two 500 μL Matrigel plugs injected bilaterally into subcutaneous tissue. To form a round shaped plug, a wide subcutaneous pocket was formed by swaying the needlepoint right and left after a routine subcutaneous insertion. The injection was performed rapidly with a 21-25 G needled to ensure the entire contents were delivered into the plug. Matrigel plugs were implanted on Day 0 of the study and treatment began on Day 1. During the treatment phase, animals were weighed on Days 1, 4, 8, 11, and 14.

After 14 days, plugs were collected. Mice were euthanized and the skin over the plugs was pulled back. Plugs were dissected out, fixed, and embedded in paraffin for histological analysis. Three sections of 5 μm thickness from each evaluable plug were immunostained with a CD31 antibody and counterstained with hematoxylin and eosin (H&E). Each matrigel plug was analyzed by measuring blood vessel counts in a cross sectional area of the plug under a microscope. For each treatment group, at least 6 matrigel plugs were analyzed to calculate the mean microvessel counts.

Results

Figure 4:
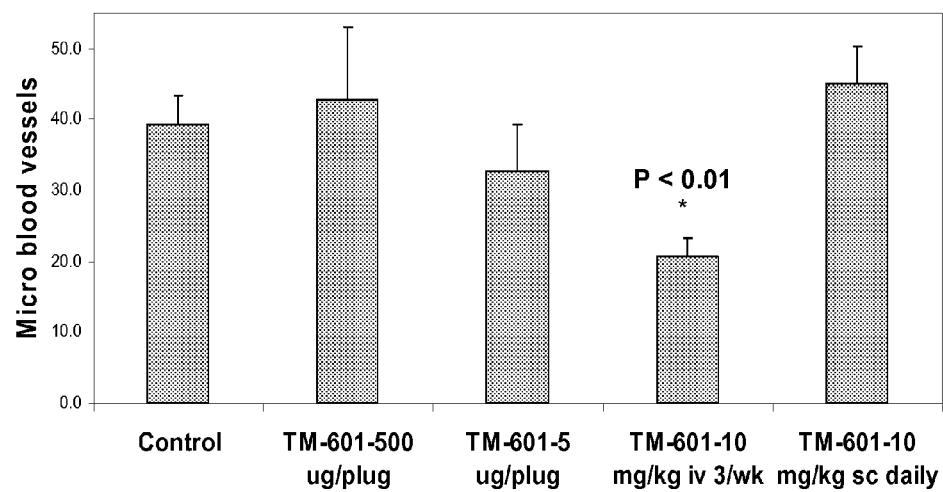
FIG. 4 shows mean microvessel counts in matrigel plugs from mice treated with TM-601 at various doses. Group of animals given 10 mg/kg intravenous injections three times per week showed a significant decrease in angiogenesis ($p<0.01$).
Figure 5:
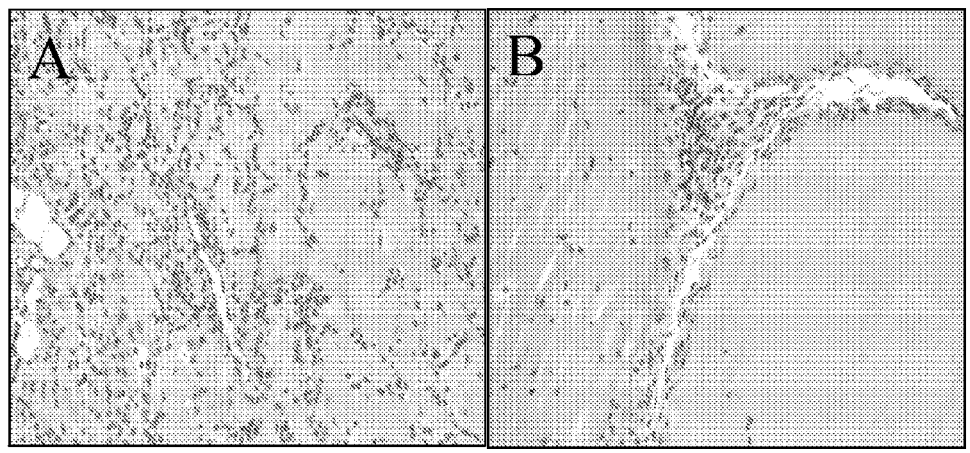
FIG. 5 shows CD31 immunostaining of matrigel plugs. (A) Control matrigel plug. (B) Matrigel plug from animals treated with intravenous injections of 10 mg/kg TM-601 three times per week.

Angiogenesis was stimulated by subcutaneous matrigel plugs that had been supplemented with VEGF, bFGF, and heparin. In order to evaluate whether TM-601 has anti-angiogenic effects in this murine model, TM-601 was either mixed with the matrigel before implantation or given to the animals systemically. After 14 days, mean microvessel counts for each group indicated that one of the treatment groups exhibited a significant decrease in blood vessel growth into the matrigel plug (FIG. 4). Intravenous injections of 10 mg/kg/injection given three times a week resulted in a 1.9-fold decrease in blood vessel counts (p<0.01 vs. control). More frequent systemic delivery of TM-601 at the same dose, but given subcutaneously, was not effective at blocking angiogenesis. Local delivery of 5 or 500 μg TM-601 into the matrigel plug at the start of the study did not significantly decrease angiogenesis. An example of the microvessel staining results is shown in FIG. 5.

Figure 6:
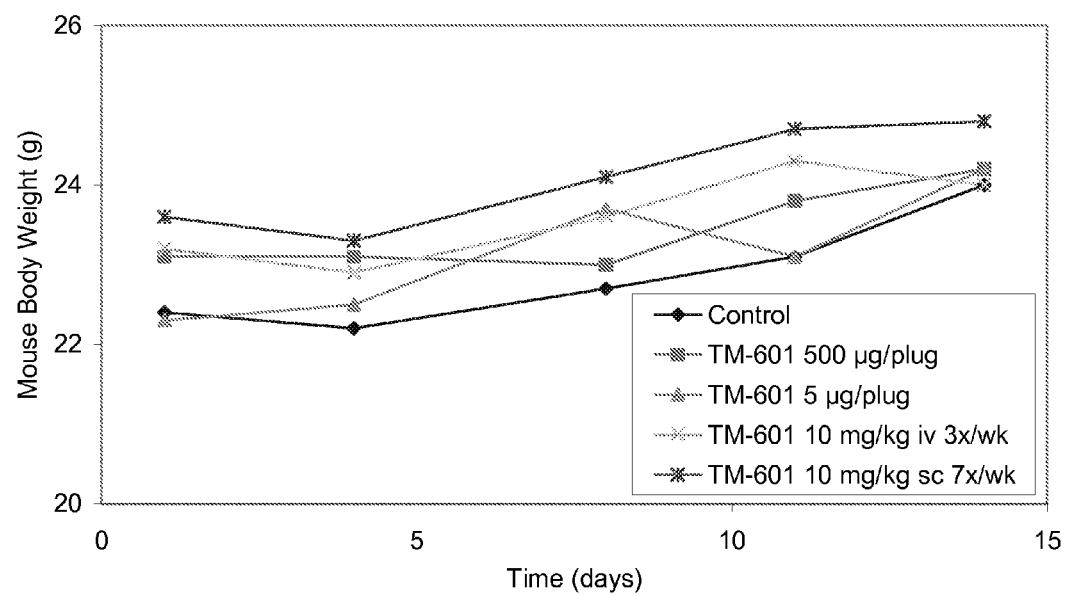
FIG. 6 shows a plot of mouse body weights throughout the course of the study.

Throughout the study, no body weight loss was observed for all mouse groups, suggesting that no severe toxicity was associated with TM-601 treatments (FIG. 6).

Discussion/Conclusion

TM-601 given at an intravenous dose of 10 mg/kg three times a week significantly reduced new blood vessel formation in the matrigel plug assay. On the other hand, more frequent subcutaneous injections at 10 mg/kg did not exhibit a similar effect, suggesting that the anti-angiogenic activity of TM-601 may be sensitive to the route of administration. In previous experiments in which the pharmacokinetics of TM-601 were measured in mice, the intravenous route was shown to yield a higher circulating concentration of TM-601 compared to subcutaneous injections. Even with a more frequent dosing schedule, subcutaneous delivery at 10 mg/kg was did not reduce angiogenesis in this model.

In the experiments described in Example 1, the CAM assay had been used to measure the anti-angiogenic activity of TM-601. In the CAM assay, TM-601 was applied directly to filter paper that had been saturated with a pro-angiogenic compound (VEGF, bFGF, LPS, EGF, IL-6, PDGF, TNFα, or HGF). TM-601 showed a dose-dependent inhibition of each of these pro-angiogenic compounds, with the maximum inhibition being observed at 100 µg, the highest dose tested (FIG. 3). In an attempt to replicate these results with similar local delivery of TM-601 at the site of angiogenesis, either 5 µg or 500 µg of TM-601 was added directly to the matrigel plug at the time of implantation. In contrast to results observed with the CAM assay in these particular experiments, this local mode of drug delivery did not block angiogenesis in the matrigel plug assay. Without wishing to be bound by any particular theory, the inventors speculate that differences in absorption, distribution, metabolism, and/or excretion of TM-601 in the two experimental models may account for the different results.

Example 3

Effects of Dose, Route, and Frequency of Administration on Anti-Angiogenic Activity of TM-601 in In Vivo Matrigel Plug Assays The experiments described in the present Example were conducted to examine anti-angiogenic activity of TM-601 delivered at various doses, by various routes of administration, and at various frequencies. Blood vessel growth into matrigel plugs implanted into mice was measured for a variety of conditions. Doses of 0.4, 2, 10, and 50 mg/kg were tested, as well as administration by intravenous and subcutaneous routes and dosing schedules of 3 times per week, twice a week, and once a week. Delivery of 10 mg/kg or 50 mg/kg TM-601 via three intravenous injections per week significantly reduced the formation of new blood vessels in the matrigel plug. At other dosing parameters tested (i.e. at lower doses, via subcutaneous injection, and less frequent dosing), no TM-601 was not observed to have an inhibitory effect on angiogenesis.

Materials and Methods

Matrigel Matrix High Concentration (from BD Biosciences) was mixed with 100 ng/mL VEGF, 100 ng/mL bFGF, and 3 ng/mL heparin at 4° C. Eight-week old female C57BL/6 mice were randomly assigned to 9 groups with 6 mice in each group. Each mouse received two 500 µL Matrigel plugs injected bilaterally in subcutaneous tissue. To form a round shaped plug, a wide subcutaneous pocket was formed by swaying the needlepoint right and left after a routine subcutaneous insertion. The injection was performed rapidly with a 21-25 G needled to ensure the entire contents were delivered into the plug. Matrigel plugs were implanted on Day 0 of the study and treatment began on Day 1. The experimental design of the study is shown in Table 2.

TABLE 2

Experimental design for mouse matrigel plug experiments at various parameters

| Group | # Animals | Treatment | Route | Dose | Route/ Schedule |
|---|---|---|---|---|---|
| 1 | 6 | none | — | — | — |
| 2 | 6 | TM-601 | i.v. | 50 mg/kg | 3× per week |
| 3 | 6 | TM-601 | i.v. | 10 mg/kg | 3× per week |
| 4 | 6 | TM-601 | i.v. | 2 mg/kg | 3× per week |
| 5 | 6 | TM-601 | i.v. | 0.4 mg/kg | 3× per week |
| 6 | 6 | TM-601 | s.c. | 50 mg/kg | 7× per week |
| 7 | 6 | TM-601 | s.c. | 10 mg/kg | 7× per week |
| 8 | 6 | TM-601 | i.v. | 10 mg/kg | 2× per week |
| 9 | 6 | TM-601 | i.v. | 10 mg/kg | 1× per week |

One group of mice was implanted with matrigel prepared as described above to serve as a positive control. Other animals were dosed with TM601 systemically throughout the study period. During the treatment phase, animals were weighed on Days 1, 5, 8, 12 and 14.

At termination on day 14, before plug removal, blood was collected from mice in groups 2-7 one and thirty minutes after the last dose (animals 1-3 in each group) and fifteen and sixty minutes after the last dose (animals 4-6 in each group). Blood was collected by retro-orbital puncture under $CO_2/O_2$ anesthesia using uncoated hematocrit tubes into lithium heparin tubes. Blood was spun at 1,500×g for 15 minutes and the plasma was transferred to a new tube. Samples were stored at −70° C. and shipped to a different laboratory for analysis.

After 14 days, plugs were collected. Mice were euthanized and the skin over the plugs was pulled back. Plugs were dissected out, fixed, and embedded in paraffin for histological analysis. Three sections of 5 µm thickness from each evaluable plug were immunostained with a CD31 antibody and counterstained with H&E. Each matrigel plug was analyzed by measuring blood vessel counts in a cross sectional area of the plug under a microscope. For each treatment group, seven to ten matrigel plugs were analyzed to calculate the mean microvessel counts.

Enzyme-linked immunosorbent assay (ELISA) analysis of blood was performed as follows. The ELISA method was developed using a rabbit anti-TM-701 antibody. TM-701 differs from TM-601 by one amino acid, a tyrosine substitution at residue 29. Rabbit anti-TM-701 antiserum has been shown to cross react with TM-601. Each well of the 96 well plate was coated with 200 ng of anti-TM-701 antibody in PBS overnight at 4° C. The plate was washed using an automated plate washer. All washes were performed with a cycle of 5 washes of 300 µL wash buffer (PBS containing 0.1% Tween-20). The last four washes in the cycle included a 20 second soak period between each wash. Samples or standards were diluted in diluent (wash buffer containing 1% bovine serum albumin) and 100 µl was analyzed. The plate was incubated at room temperature for 75 to 90 minutes with gentle rocking and then the plate was washed as before. Anti-TM-701 antibody that had been biotinylated using standard procedures was added to each well in a volume of 100 µL of diluent. Each well contained 85 ng of biotinylated antibody (1/3200 dilution of 2.7 mg/ml stock solution). The plate was incubated for 60 minutes with gentle rocking and washed as before. Horseradish peroxidase streptavidin (Vector Laboratories) was diluted 1/500 in diluent and 100 µL was added to each well. The plate was incubated with gentle rocking for 45 to 60 minutes. The plate was then washed as before, except that the last wash was not removed and instead the solution remained on the plate for 5 minutes. The wells were then rinsed with 200 µl PBS and 100 μl of ABTS (Calbiochem) was added to each well. The plate was mixed every 5 minutes and the absorbance at 415 nm was read after 20 minutes using a BioRad Model 550 plate reader. Unknown sample concentrations were calculated using the software package "Microplate Manager v.5.2.1."

Results

Figure 7:
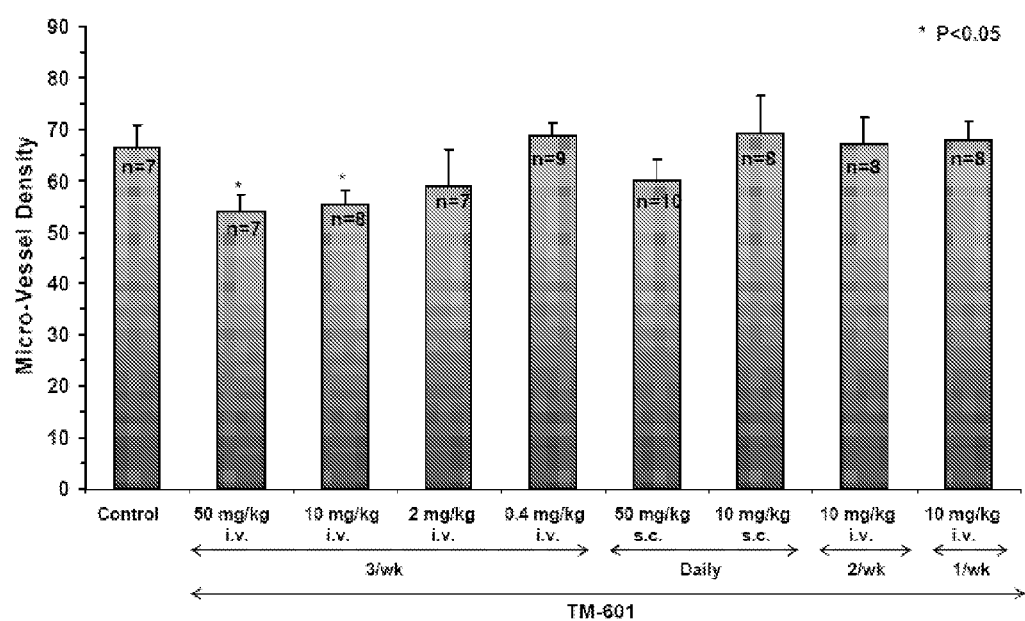
FIG. 7 shows mean microvessel counts in matrigel plugs from mice treated with TM-601 at various doses. Group of animals given 10 or 50 mg/kg intravenous injections three times per week showed a significant decrease in angiogenesis (*, $p<0.05$).
Figure 8:
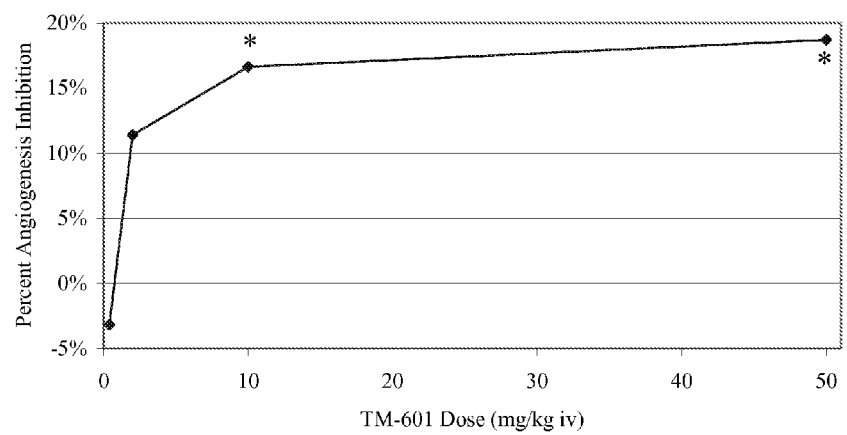
FIG. 8 shows dose-dependent inhibition of angiogenesis by TM-601 given via three weekly intravenous injections. Only the 10 and 50 mg/kg doses are significantly different than the control group. Nevertheless, there appears to be a dose-dependent effect throughout all dose groups.

Angiogenesis was stimulated by subcutaneous matrigel plugs that had been supplemented with VEGF, bFGF and heparin. In order to evaluate whether TM-601 has anti-angiogenic effects in this murine model, TM601 was injected systemically. After 14 days, mean microvessel counts for each group indicated that two of the treatment groups exhibited a significant decrease in blood vessel growth into the matrigel plug: three intravenous injections per week at doses of either 10 or 50 mg/kg (FIG. 7). Although lower doses of TM601 administered intravenously three times a week did not affect angiogenesis in a statistically significant manner, there appeared to be a dose-dependent effect (FIG. 8).

Figure 9:
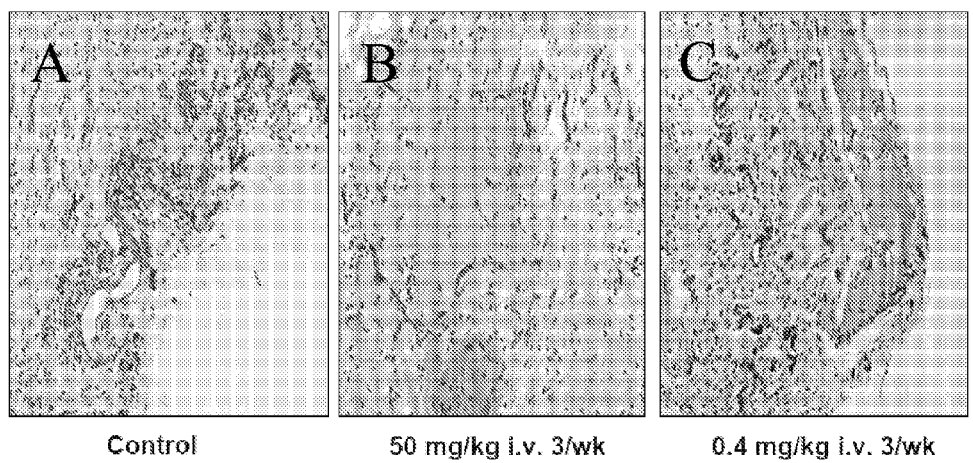
FIG. 9 shows CD31 immunostaining of matrigel plugs. (A) Control matrigel plug. (B) Matrigel plug from animals treated with intravenous injections of 50 mg/kg TM-601 three times per week. (C) Matrigel plug from animal treated with intravenous injections of 0.4 mg/kg TM-601 three times per week.

Interestingly, daily subcutaneous injections of TM601 at five times the 10 mg/kg dose (which decreased angiogenesis with an intravenous route of administration) led to a slight but not statistically significant decrease in angiogenesis. Furthermore, decreasing the frequency of dosing from three times per week to either twice or once per week resulted in loss of anti-angiogenic activity. An example of the microvessel staining results is shown in FIG. 9.

Figure 10:
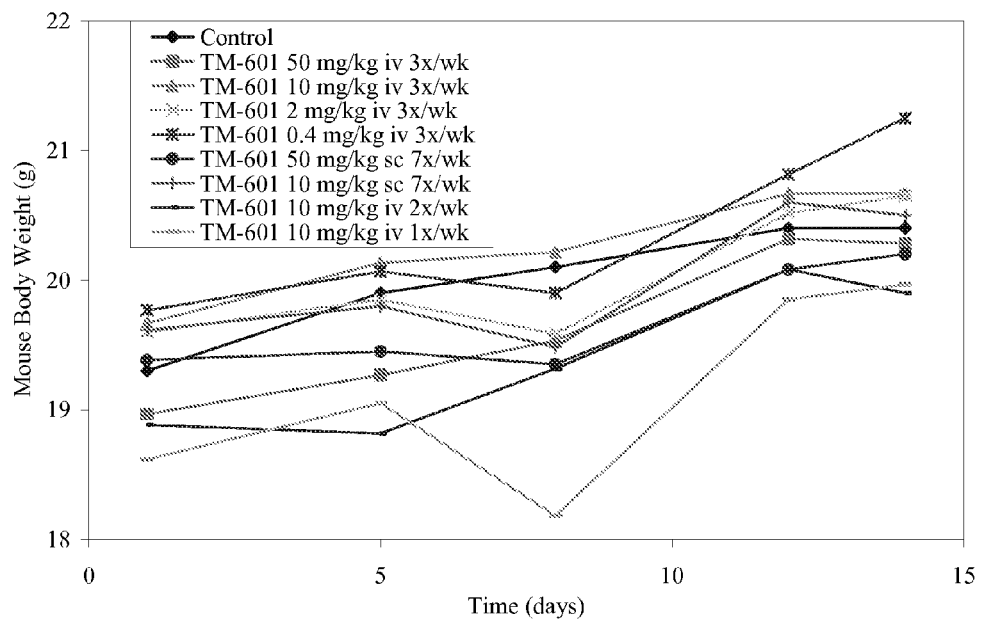
FIG. 10 shows a plot of mouse body weights throughout the course of the study.

Throughout the study, no body weight loss was observed in any treatment groups, suggesting that there was no severe toxicity associated with TM601 treatments (FIG. 10).

Figure 11:
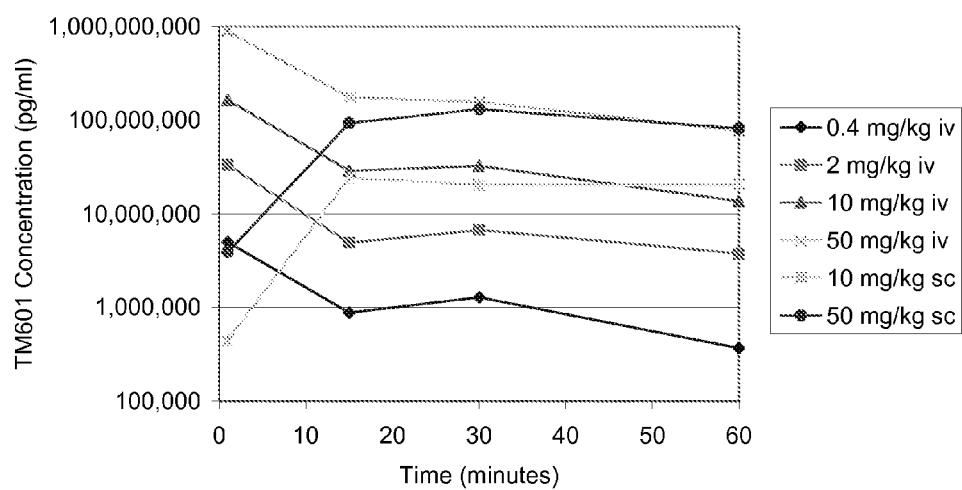
FIG. 11 shows pharmacokinetics of TM-601 in mouse plasma following the last dose. Concentration of TM-601 in plasma is plotted versus time for various doses of TM-601.

Blood samples were collected following the final dose and were analyzed for plasma TM601 levels (FIG. 11). TM601 levels and half-lives were similar to those found in previous studies.

Discussion/Conclusion

TM-601 given at an intravenous dose of 10 or 50 mg/kg three time a week significantly reduced new blood vessel formation in the matrigel plug assay. Nevertheless, more frequent subcutaneous injections at up to 50 mg/kg did not exhibit a similar effect, suggesting that the anti-angiogenic activity of TM-601 may be sensitive to the route of administration. Daily subcutaneous dosing at 50 m/kg represents more than a ten-fold increase in the cumulative dose during the course of the experiment (50 mg/kg×14 subcutaneous injections compared to 10 mg/kg×6 intravenous injections). Thus, even with a more frequent dosing schedule and significantly greater total cumulative dose, subcutaneous delivery at 50 mg/kg led only to a slight but not statistically significant decrease in angiogenesis. A similar finding was described in Example 2. In experiments in which the pharmacokinetics of TM601 were measured in mice, including this one, the intravenous route was shown to yield a higher peak circulating concentration of TM601 compared to subcutaneous injections. (See, for Example, FIG. 11).

Another interesting finding in this study was that the frequency of intravenous delivery is critical for anti-angiogenic effects of TM-601. Whereas a three times per week dosing schedule resulted in significant inhibition of angiogenesis, dosing either twice or once per week did not affect angiogenesis in this model.

All routes, dose levels, and schedules of TM-601 administration, including intravenous delivery of up to 50 mg/kg TM601 given three times a week, were well tolerated in the mice. All groups of animals gained weight throughout the 14-day study.

Example 4

Anti-Tumor Activity of TM-601 on Human Tumors Grown on Choriallantoic Membranes

As demonstrated in Example 1, TM-601 inhibits angiogenesis stimulated by VEGF, bFGF, LPS, EGF, IL-6, PDGF, TNFα, and HGF in a CAM assay. The experiments described in this Example were performed to determine whether TM-601 can slow tumor growth via this anti-angiogenic activity.

Tumor cells implanted on the surface of chick egg CAM stimulate angiogenesis. TM-601 was shown to slow tumor growth in the CAM assay for a number of human tumor cell lines. Nevertheless, TM-601 does not slow tumor cell proliferation in vitro, which suggests that TM-601 affects tumor growth indirectly. It was hypothesized, without wishing to be bound by any particular theory, that TM-601 affects tumor growth through its effects on the vasculature. To test this hypothesis, tumors grown on CAM were treated with either TM-601 or saline and then analyzed for hemoglobin levels. TM-601 was found to significantly decrease the amount of hemoglobin in the tumors and thus presumably decreased the vascularization of the tumors.

Materials and Methods

Cell Culture

Human tumor cell lines were supplied by ATCC and grown according to recommendations from the supplier. Exceptions are the D54-MG line (supplied by Dr. Bigner, Duke University) and a primary isolate from a pancreatic carcinoma. Prior to addition to the CAM, subconfluent cultures were trypsinized and resuspended to a concentration of $1\times10^6$ cells in 30 μL. Table 3 lists tumor cell lines used in the tumor-CAM experiments.

TABLE 3

Cell lines used in tumor-CAM experiments.

| Cell line | Properties |
| --- | --- |
| U87-MG | human glioblastoma (grade III) |
| D54-MG | human glioblastoma (grade III-IV) |
| HS683 | human non-invasive glioma (stage I) |
| H1299 | human non-small cell carcinoma |
| PC-3 | human prostate adenocarcinoma |
| SK-Mel-28 | human malignant melanoma |
| Pancreatic carcinoma | primary cell culture |

Cell Proliferation Studies

U87 and PC-3 cells were cultured according to recommendations by ATCC. For U87 proliferation studies, approximately 200 cells were plated per well in a 96-well tray and incubated overnight at 37° C. with 5% $CO_2$. The media was then aspirated from each well and replaced with fresh media containing approximately 100, 33, 10, 3.3, 1.0, 0.33, 0.1, 0.03, 0.01, 0.03 or 0 μM TM-601 and incubated for 72 hours. To determine the number of cells at the end of this period, the sulforhodamine method was used (Sigma, cat. #TOX-6). First, 25 μL of 50% TCA was added to each well and the plate was incubated at 4° C. for 1 hour. The wells were then washed 4 times with water and air dried. Next, 50 μL of a 4% Sulforhodamine solution was added to each well and cells were stained for 30 minutes. Wells were then washed 3 times with 1% acetic acid and air dried. Finally, 100 μL of 10 mM Tris was added to each well and after 5 minutes the tray was mixed and then the absorbance was read in a plate reader at 565 nm. For PC-3 proliferation studies, cells were plated in 24-well trays at approximately $1\times10^4$ cells per well and incubated overnight at 37° C. in 5% $CO_2$. Media was aspirated from each well and replaced with fresh media containing no additive, 20 nM, or 1 µM TM-601 in duplicate. Cells were then incubated for an additional 72 hours and cells were counted in a hemocytometer following trypsinization.

Tumor CAM

Fertilized chick eggs were incubated at 37° C. with 55% humidity. Ten days after fertilization, a small hole was punctured with a hypodermic needle in the area of the shell concealing the air sac. A second hole was punctured in the shell on the broadside of the egg directly over an avascular portion of the embryonic membrane. A false air sac was created beneath the second hold by the application of negative pressure to the first hole, which caused the membrane to separate from the shell. A window approximately 1.0 cm² in area was cut in the shell over the dropped CAM with the use of a small grinding wheel, allowing direct access to the underlying CAM. The surface of the CAM was dried and 30 µL of cells ($1\times10^6$ cells) was applied to the CAM. At the same time, 10 µg of TM-601 was added directly to the surface of the tumor. Tumors continued to grown for 7 days, at which time the tumor mass was removed and weighed.

A similar method was employed for measuring hemoglobin within the tumors. $1\times10^6$ cells were mixed with matrigel (growth factor reduced from BD Biosciences) and applied to the CAM on day 10 of development. As a control, matrigel alone was applied to the CAM. Cells were treated with TM-601 by mixing the cells with 0.9 µL of a 100 µM stock of TM-601 (360 ng TM-601). In addition, 0.1 µL of a 100 µM stock was applied around the matrigel (40 ng TM-601). Tumors were harvested seven days later and dissected from any underlying vasculature. The tumor was homogenized in 0.5 mL double-distilled water and the samples were spun at 4,000 rpm for 10 minutes. The supernatants were then collected and 50 µL of the supernatant was mixed with 50 µL Drabkin's reagent (Sigma). After 15-30 minutes at room temperature this mixture was placed in a 96-well plate. The optical density at 545 nm was measured and compared to a standard curve of know hemoglobin concentrations.

Results

Figure 12:
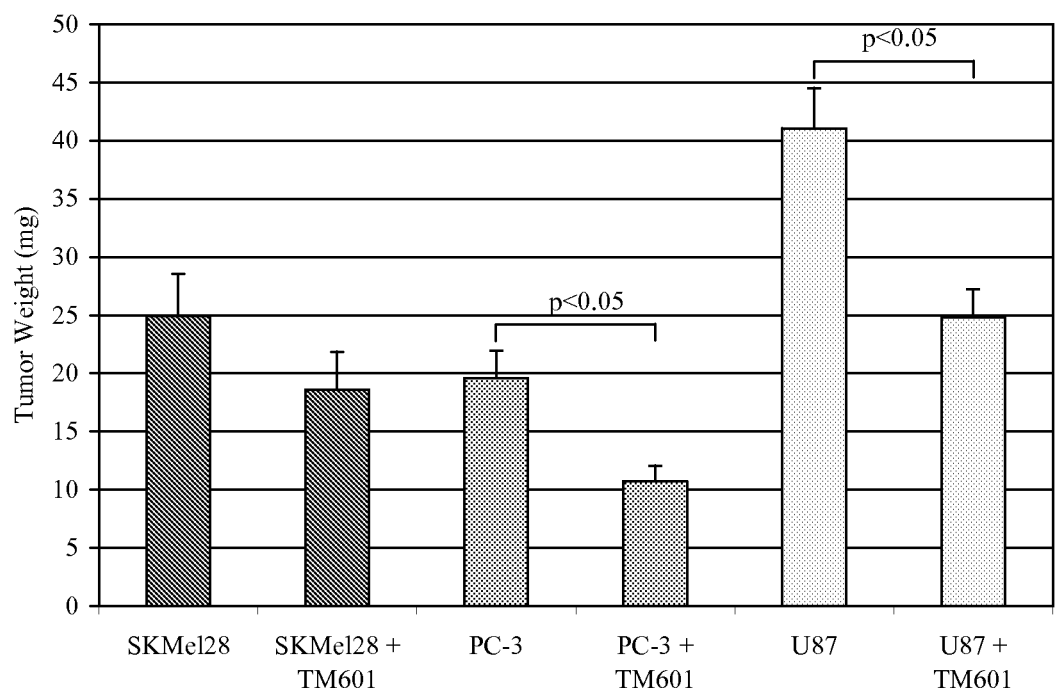
FIG. 12 depicts effect of 10 μg TM-601 on tumor growth in the tumor-CAM. TM-601 significantly slowed tumor growth for PC-3 and U87 tumors grown on the CAM.

Tumor-CAM experiments were preformed on three different occasions. In the first pilot experiment, three tumor lines were tested (PC-3, U87 and Sk-Mel-28). Tumors implanted on the surface of the CAM were either untreated or treated with 10 µg TM-601. Following 7 days of growth, the tumors were weighed (Table 4) and mean tumor values for each tumor were compared. TM-601 treatment of the tumors resulted in a significant decrease in tumor growth ($p<0.05$) for PC-3 and U87 tumors (FIG. 12).

TABLE 4

Raw data of tumor weights

| CAM Condition: | | | | | | | | | | |
|---|---|---|---|---|---|---|---|---|---|---|
| SK-Mel28 – melanoma | 23.3 | 17.6 | 22.5 | 46.0 | 14.0 | 12.7 | 23.6 | 32.9 | 40.9 | 15.7 |
| SK-Mel28 + TM601 | 9.8 | 24.3 | 19.6 | 24.4 | 13.8 | 6.4 | 14.1 | 19.3 | 11.6 | 42.6 |
| PC3 – prostate | 9.0 | 15.7 | 30.7 | 16.0 | 18.1 | 18.2 | 20.5 | 30.9 | 17.1 | |
| PC3 + TM601 | 6.5 | 9.1 | 6.2 | 8.4 | 13.9 | 11.2 | 17.5 | 12.7 | | |
| U87 – glioblastoma | 34.5 | 45.9 | 27.3 | 40.3 | 29.0 | 56.1 | 37.8 | 42.3 | 56.2 | |
| U87 + TM601 | 17.1 | 36.4 | 26.9 | 24.8 | 18.9 | 26.3 | 30.6 | 17.5 | | |

Figure 13:
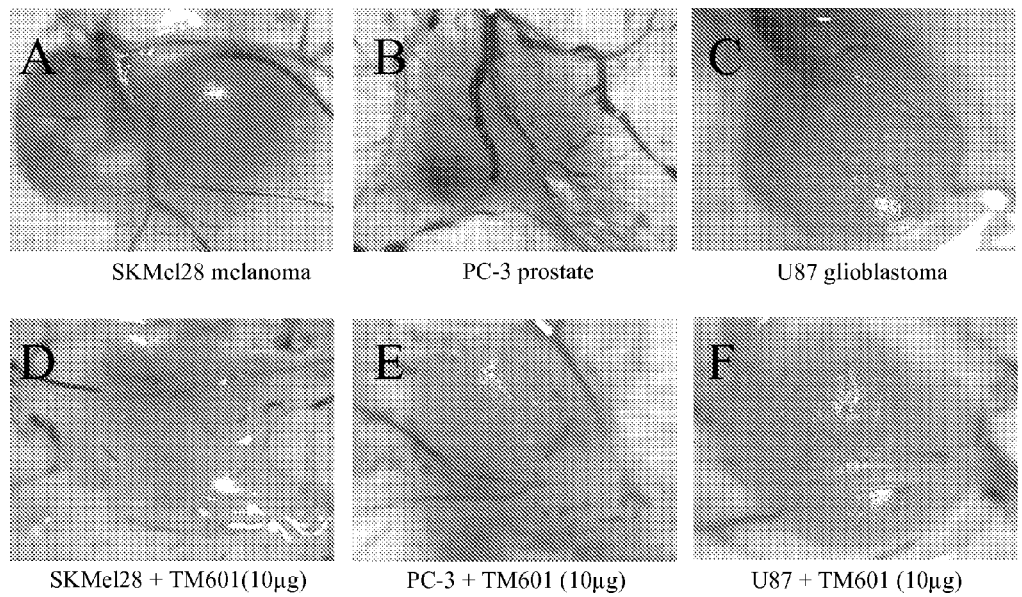
FIG. 13 depicts photomicrographs of representative tumors grown on the CAM without further treatment (A, B, C) or after treatment with 10 ug TM-601 (D, E, F).
Figure 14:
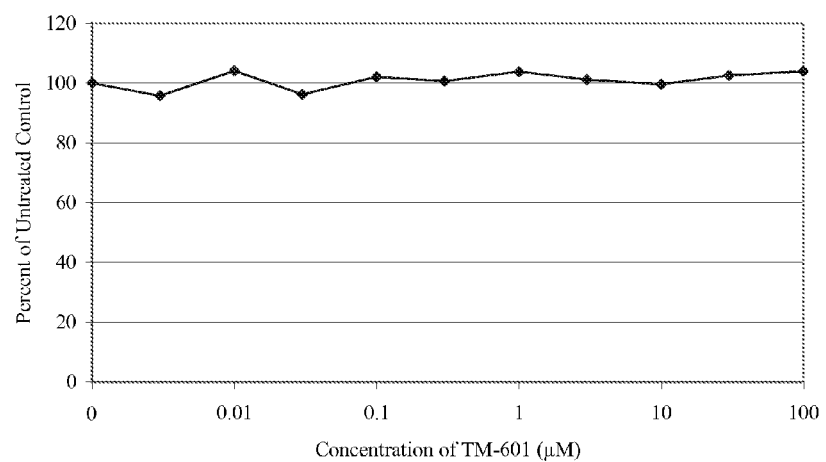
FIG. 14 shows that TM-601 does not affect the proliferation of U87 tumor cells in vitro. U87 cells were grown in culture media for 72 hrs in the presence or absence of TM-601. At concentrations up to 100 μM, TM-601 had no effect on U87 cell proliferation or cell death.

Photographs of the tumors were taken at the time of tumor explant and there appeared to be a decrease in the vascularization of the tumors (FIG. 13). The were two explanations for this observation: either TM-601 decreased tumor growth which therefore resulted in a reduction in the stimulation of angiogenesis, or TM-601 decreased angiogenesis which slowed tumor growth. To distinguish between these two possibilities, in vitro cultures of PC-3 and U87 were grown in the presence of various amounts of TM-601. After 72 hours of growth, the number of PC-3 cells grown in the presence of two different concentrations of TM-601 was not significantly different than cells grown in the absence of TM-601. There were 740,000 average cells in the control compared to 712,500 with 20 nM TM601 and 708,500 cells with 1 µM TM601. Similarly, over a broad range of TM-601 concentrations, the number of U87 cells did not significantly decrease (FIG. 14). Thus, TM-601 had no effect on the proliferation of PC-3 or U87 cells in culture, suggesting that TM-601 does not directly act on tumor cells. As described previously in Example 1, TM-601 inhibits angiogenesis in the CAM model, suggesting that the primary effect of TM-601 is as an anti-angiogenic compound.

A second tumor-CAM experiment was performed to confirm the initial findings and broaden the number of tumor cell lines tested. In addition to the three cells lines tested previously, HS683, D54MG, H1299 and a primary pancreatic carcinoma were also examined (Table 5). These results confirmed the effects seen on tumor growth of U87 and PC-3 tumors and also showed that decreases in SK-Mel28 tumor growth which were not statistically significant in the first experiment were significant in the second experiment. Tumor growth of primary pancreatic carcinoma isolate was also reduced by TM-601. The tumor cell lines that were not responsive to TM-601 in this experiment included HS683, D54 and H1299. One possible reason for this finding is that these tumors grew more slowly and therefore may not have reached a stage where vascular support was necessary for rapid tumor growth. If this were the case, then an anti-angiogenic compound which decreases tumor vasculature would not be expected to be as effective.

TABLE 5

Raw data for tumor growth

| CAM Condition: | | | | | | | | | | |
|---|---|---|---|---|---|---|---|---|---|---|
| SK-Mel28 – melanoma | 23.3 | 27.6 | 22.5 | 46.0 | 24.0 | 22.7 | 23.6 | 32.9 | 40.9 | 25.7 |
| SK-Mel28 + TM601 | 9.8 | 24.3 | 19.6 | 24.4 | 13.8 | 6.4 | 14.1 | 19.3 | 11.6 | 12.6 |
| PC3 – prostate | 19.0 | 15.7 | 30.7 | 16.0 | 18.1 | 18.2 | 20.5 | 30.9 | 17.1 | |
| PC3 + TM601 | 6.5 | 9.1 | 6.2 | 8.4 | 13.9 | 12.2 | 17.5 | 12.7 | | |
| U87 – glioblastoma | 34.5 | 45.9 | 27.3 | 40.3 | 29.0 | 56.1 | 37.8 | 42.3 | 56.2 | |
| U87 + TM601 | 17.1 | 26.4 | 26.9 | 24.8 | 18.9 | 26.3 | 20.6 | 17.5 | | |
| HS683 – glioma | 15.5 | 13.8 | 11.9 | 14.1 | 11.6 | 7.8 | 11.6 | 21.5 | | |
| HS683 + TM601 | 9 | 12 | 17 | 25.6 | 8.3 | 10 | 6.7 | 7.9 | 9.3 | 5.1 |
| D54 – glioblastoma | 10.8 | 15.8 | 17.5 | 10.9 | 18.4 | 14.3 | 12 | 16.4 | | |
| D54 + TM601 | 11.5 | 12.6 | 8.6 | 23.0 | 11.2 | 14.3 | 15.7 | 10.5 | 15.3 | 14.1 |
| H1299 – non-small cell lung | 30.9 | 17.0 | 21.2 | 18.2 | 9.3 | 24.9 | 20.4 | 11.8 | | |
| H1299 + TM601 | 9.0 | 13.8 | 15.0 | 14.9 | 21.7 | 16.8 | 17.3 | 19 | | |
| Pancreatic carcinoma | 12.8 | 29.5 | 11 | 30.2 | 16.6 | 19.3 | 27.1 | 20.2 | 12.2 | |
| Panc. + TM601 | 7.6 | 11.5 | 17.4 | 7.8 | 7.7 | 18.4 | 9.1 | 11.8 | 6.5 | 7.6 |

Figure 15:
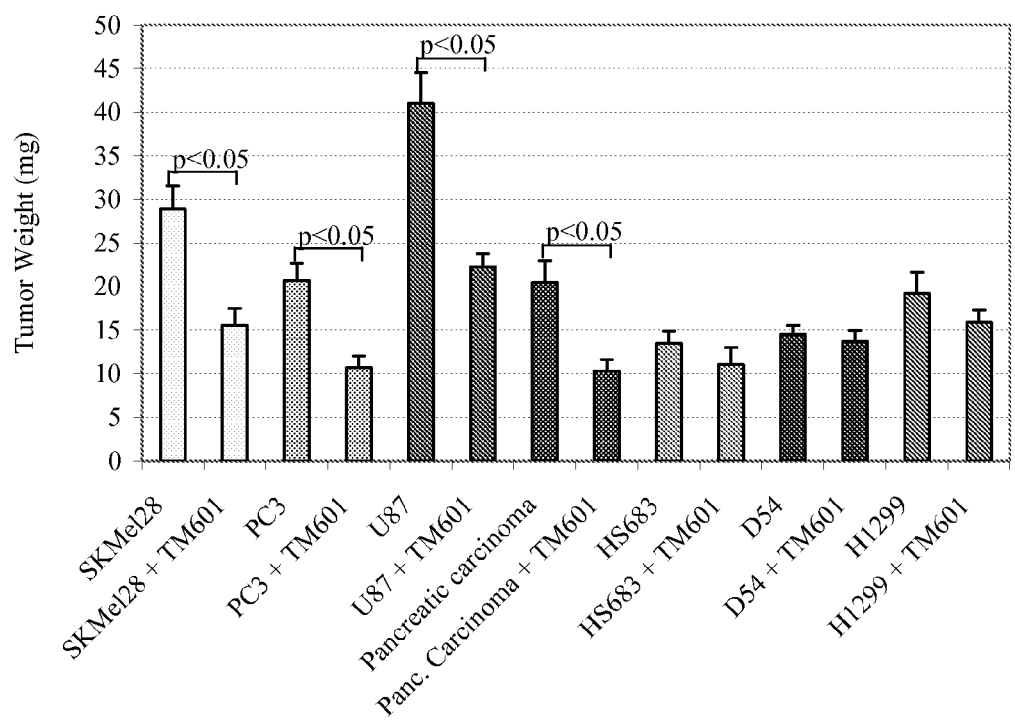
FIG. 15 shows the effect of 10 μg TM-601 on tumor growth in the tumor-CAM. TM-601 significantly slowed tumor growth for SKMel28, PC-3, U87 and pancreatic carcinoma tumors grown on the CAM.
Figure 16:
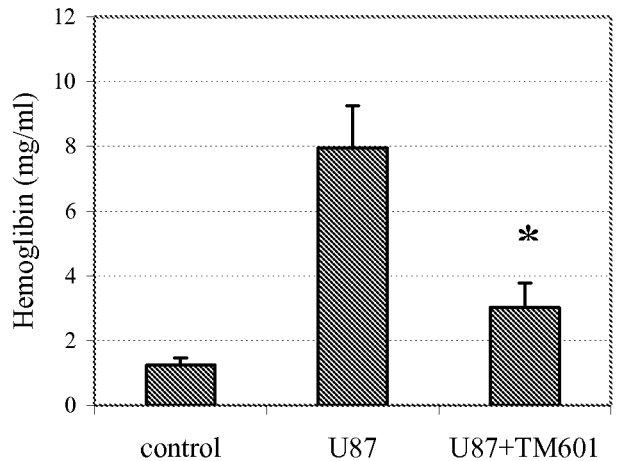
FIG. 16 shows that amounts of hemoglobin in tumors grown on the CAM are inhibited by TM-601. Human tumor cells (A): 87 glioma, (B): D54 glioma or (C): pancreatic carcinoma) were applied to the surface of the CAM in matrigel. The cells either contained saline or 400 ng TM-601. As a control, matrigel alone was applied. Seven days later, the area of implantation was removed and hemoglobin levels were measured. *Hemoglobin levels in tumors treated with TM601 are statistically less than non-treated cells ($p<0.05$).
Figure 16:
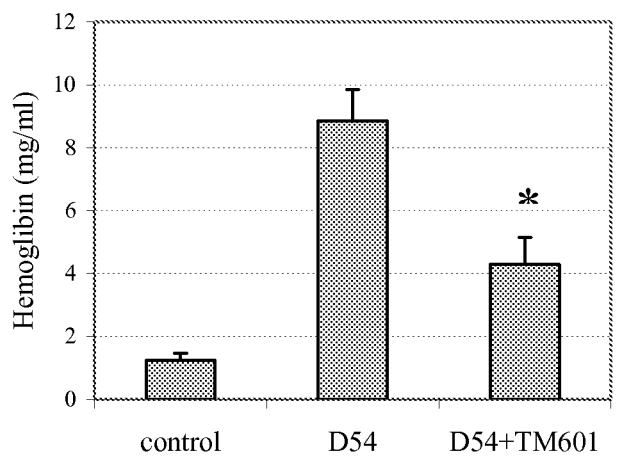
Figure 16:
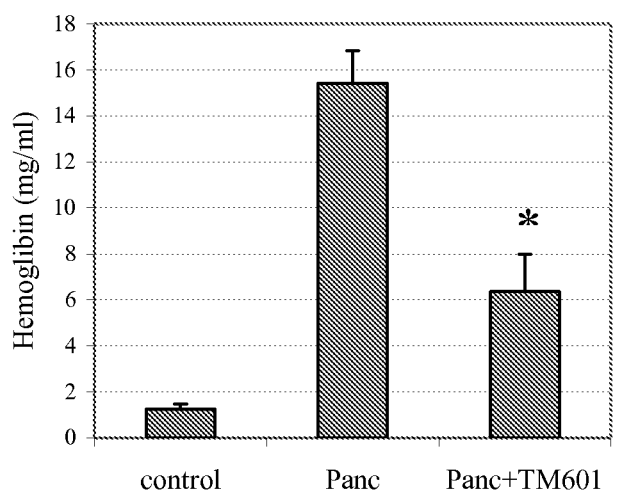

To further support the theory that TM-601 decreases neovascularization in the tumor-CAM model, total hemoglobin was measured in the tumors that were grown on the CAM. FIG. 16 shows that TM-601 treatment significantly reduced hemoglobin levels for all three tumors tested (U87, D54 and pancreatic carcinomas). Interestingly, D54 tumor growth was not affected by TM-601 treatment in one experiment (FIG. 15) but hemoglobin measurements in another experiment showed that D54 tumor blood levels were decreased.

Discussion/Conclusion

Data from the chorioallantoic membrane assay (CAM assay) indicate that TM-601 inhibits angiogenesis which was stimulated by VEGF, bFGF, lipopolysaccharide, EGF, IL-6, PDGF, TNFα, or HGF. To determine whether TM-601 can slow tumor growth via this anti-angiogenic effect, experiments were performed to assess the effect of TM-601 on human tumor growth on the surface of the CAM. Tumor cells that grow on the CAM form a solid mass that both stimulates and requires a blood supply to sustain growth. Data presented in this report support the hypothesis that TM-601 inhibits tumor growth via an anti-angiogenic effect. The growth of a number of human tumors implanted on the CAM were reduced by TM-601. This included PC-3, U87, SK-Mel-28 and Pancreatic carcinoma cells. Nevertheless, not all tumors responded, and some responded in some experiments and not others. Without wishing to be bound by any particular theory, we suggest that one explanation of these observations may be that dependence of vascular support by the tumor requires that the tumor grow to a point where oxygen and nutrients become limiting. This may not occur if fewer cells are implanted at the start of the experiment. It was noted that the tumors that did not show responses to TM-601 tended to be on average smaller than other larger tumors that did respond (see FIG. 15), so this may be the cause of the inconsistency. Evidence that TM-601 is acting on the vasculature and not directly on tumor cell proliferation is shown in FIGS. 14 and 16, which show that tumor cell growth is not sensitive to TM-601 in vitro and that TM-601 treatment of tumors grown on the CAM causes a reduction in hemoglobin within the tumor. Thus, using the CAM assay, TM-601 has been shown to inhibit neovascularization stimulated by specific pro-angiogenic factors (e.g. VEGF, bFGF, lipopolysaccharide, EGF, IL-6, PDGF, TNFα, and HGF) as well as angiogenesis stimulated by human tumor cells.

Example 5

Synergistic Anti-Angiogenic Effects of Chlorotoxin

Previous experiments using the Chick Chorioallantoic Membrane (CAM) assay have shown that synthetic chlorotoxin (TM-601) has a dose-dependent inhibitory affect on angiogenesis stimulated by VEGF, bFGF, lipopolysaccharide (LPS), EGF, IL-6, PDGF, TNFα, or HGF. In the current Example, this effect was independently verified experiments conducted by a second contract laboratory. In addition, the anti-angiogenic effect occurred at a similar concentration of TM-601 to the anti-VEGF antibody agents Avastin and Lucentis. When TM-601 was given together with either Avastin or Lucentis, the effect was either additive or synergistic. Finally, TM-601 was shown to inhibit angiogenesis when injected intravenously in the CAM assay.

Experiments using the Chick Chorioallantoic Membrane (CAM) assay were conducted to evaluate further the anti-angiogenic properties of TM-601. Effects on neovascularization in the CAM assay had been described in Example 1. Additional CAM experiments were performed in the present Example to examine the effect of TM-601 on non-stimulated neovascularization; to repeat the conditions described in Example 1 showing inhibition of VEGF-, bFGF- and LPS-stimulated angiogenesis; to investigate anti-angiogenic effects of intravenously injected TM-601; to compare the potency of TM-601 with known angiogenesis inhibitors (Avastin and Lucentis); and to test combinations of TM-601 with either Avastin or Lucentis. (Experiments on combinations with Avastin or Luentis were performed at least twice).

TM-601 was shown to inhibit angiogenesis in each of the experiments outline above in a dose-dependent manner. The observed effect occurred at a similar concentration to Avastin and Lucentis, both anti-VEGF antibody agents. Results also indicate that there is either an additive or synergistic effect between TM-601 and the two anti-VEGF antibodies.

Materials and Methods

The CAM assay was performed using two different methods, depending on the contract laboratory where it was performed. At one contract laboratory, fertilized chick eggs were incubated at 37° C. with 55% humidity. Ten days after fertilization, a small hole was punctured with a hypodermic needle in the area of the shell concealing the air sac. A second hole was punctured in the shell on the broadside of the egg directly over an avascular portion of the embryonic membrane. A false air sac was created beneath the second hold by the application of negative pressure to the first hole, which caused the membrane to separate from the shell. A window approximately 1.0 cm$^2$ in area was cut in the shell over the dropped CAM with the use of a small grinding wheel, allowing direct access to the underlying CAM. Filter disks were soaked in 3 mg/mL rtisone acetate and subsequently air dried under sterile conditions. Each experiment involved a control (PBS), a positive control (pro-angiogenic factor), and treatment groups with the pro-angiogenic factor in addition TM-601 at different doses. Sterile filter disks with VEGF at 2 µg/mL were placed on the growing CAMs. At 24 h, TM-601 (0.001-100 µg) or the control vehicle was added topically to the CAMs. CAMs were harvested on the 3rd day of stimulation. The CAM tissue directly beneath the filter disk was removed from the embryos and tissues were washed three times with PBS. Blood vessel branch points in the 5 m filter disk area were counted at 30× magnification as a quantitative indicator of vascular sprouting in response to the pro-angiogenic compounds. Each egg was analyzed by two different operators and the average reading was reported. The following equation was used to calculate the mean percent angiogenesis inhibition with VEGF-stimulation:

$$\text{Mean \% inhibition} = \frac{(\text{\# branch points for } VEGF) - (\text{\# branch points for } TM\text{-}601)}{(\text{\# branch points for } VEGF) - (\text{\# branch points for } PBS)}$$

At the second contract laboratory, the CAM assay was performed as follows. Fertilized chicken eggs were incubated at 37.5° C. in a humidified egg incubator with forced air circulation. On embryonic day 3, eggs were cracked open and the embryos were carefully transferred into a 100 mm$^3$ Petri plate to continue their development in a cell culture incubator at 37.5° C. Pre-made methylcellulose discs of a bout 2 mm in diameter were gently implanted on top of the embryo chorioallantoic membrane on embryonic day 5 and either the test agent alone, or angiogenic stimulants (VEGF, bFGF, LPS, control solution) were added on top of the methylcellulose disc. VEGF was added at 40 ng/disc, bFGF at 20 ng/disc and LPS at 100 ng/disc. The embryos were incubated for two more days in the cell culture incubator. On embryonic day 7, the CAM membranes were examined and quantitatively analyzed for new blood vessel formation after injection of dyed non-fat dry milk solution. The treatment effects on angiogenesis were evaluated by determining vascular density indexed (VDI) on CAMs only with viable chicken embryos. The VDI of each CAM represents the number of intersections made by blood vessels with three equidistant centric circles on the area covered by the methylcellulose discs by using Image Pro Plus software. The average VDI based on the quantitative analyses for each group (N>5) is listed in Tables 6 and 7 as a percent of the saline control. For the purpose of internal consistency and comparisons between the data generated at the two labs, the figures containing the inhibition curves were evaluated using the same equation used by PRI Albany that has been listed above. The exception is FIG. 1, since no angiogenesis stimulation was applied, the same equation could not be used.

There are two key differences between the two CAM methods. At the second contract laboratory, the eggs are cracked open whereas at the first laboratory, the CAM assay is run within the egg shell. Also, at the second laboratory, the assay runs for 2 days and the first laboratory runs the assay for 3 days from the time of drug addition to the time of angiogenesis analyses. Other more subtle differences in the methods may also exist.

Results

Figure 17:
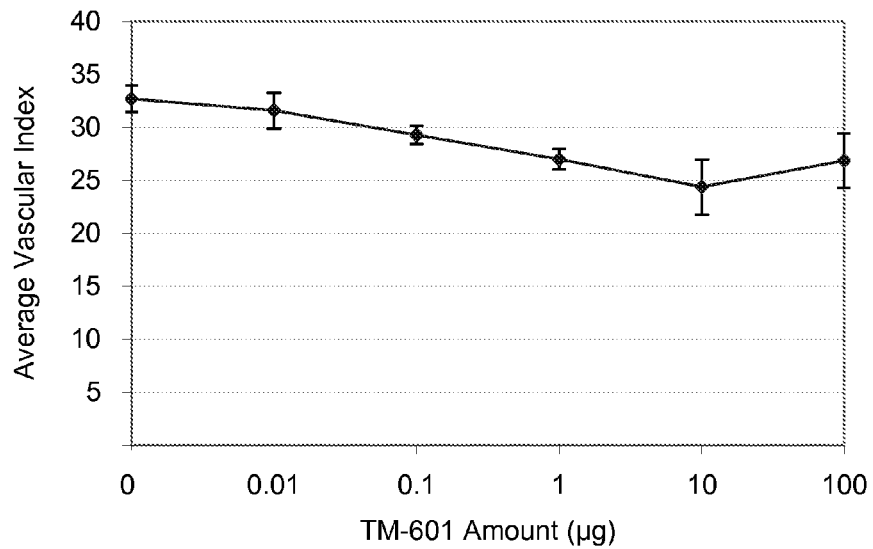
FIG. 17 shows the inhibitory effect of TM-601 on normal developing vasculature in the CAM assay. The highest 3 amounts of TM-601 (1, 10 and 100 μg) effected statistically significant decreases in vascular density.

At the first laboratory, TM-601 was found to block non-stimulated angiogenesis in a dose-dependent manner. Control non-stimulated eggs were compared with non-stimulated eggs treated with varying amounts of TM-610. In this way, the effect of TM-601 on the normal angiogenesis process in the egg was tested. The raw data are shown in Table 6 and a plot of the curve is shown in FIG. 17.

TABLE 6

Significant decreases in neovascularization mediated by TM-601

| Group | # Embryos | Treatment | Dose (µg) | VDI | SEM | P value |
|---|---|---|---|---|---|---|
| 1 | 10 | — | — | 33 | 1.2 | |
| 6 | 5 | TM-601 | 0.01 | 32 | 1.7 | NS |
| 5 | 7 | TM-601 | 0.1 | 29 | 0.9 | NS |
| 4 | 9 | TM-601 | 1 | 27 | 1.0 | 0.01 |
| 3 | 8 | TM-601 | 10 | 24 | 2.6 | 0.01 |
| 2 | 7 | TM-601 | 100 | 27 | 2.5 | 0.05 |

Figure 18:
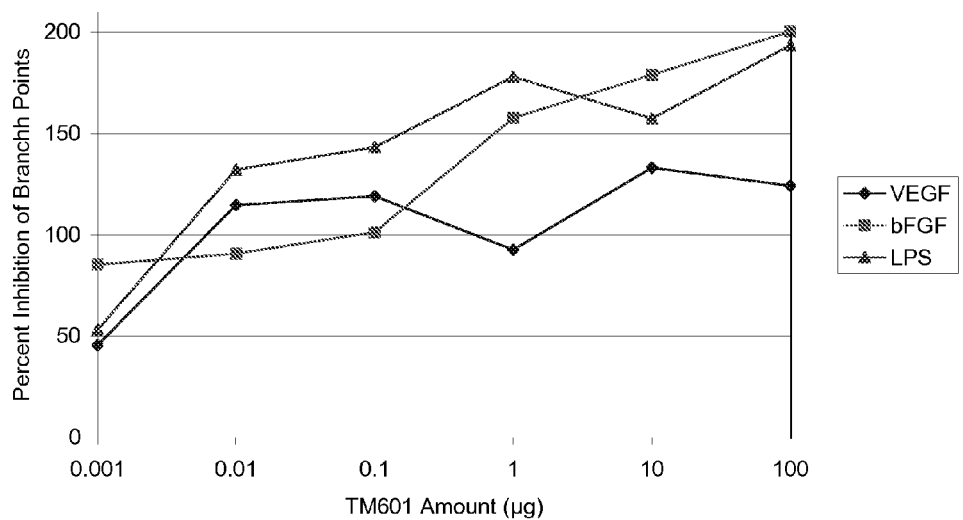
FIG. 18 shows that TM-601 inhibits VEGF-, bFGF- and LPS-stimulated angiogenesis in a dose-dependent manner. Greater than 100% inhibition indicates that the level of inhibition is greater than the non-stimulated saline control value, indicating that TM-601 inhibited not only the amount of neovascularization stimulated by the pro-anti-angiogenic factors, but also neovascularization resulting from angiogenesis intrinsic to the developing chick.
Figure 19:
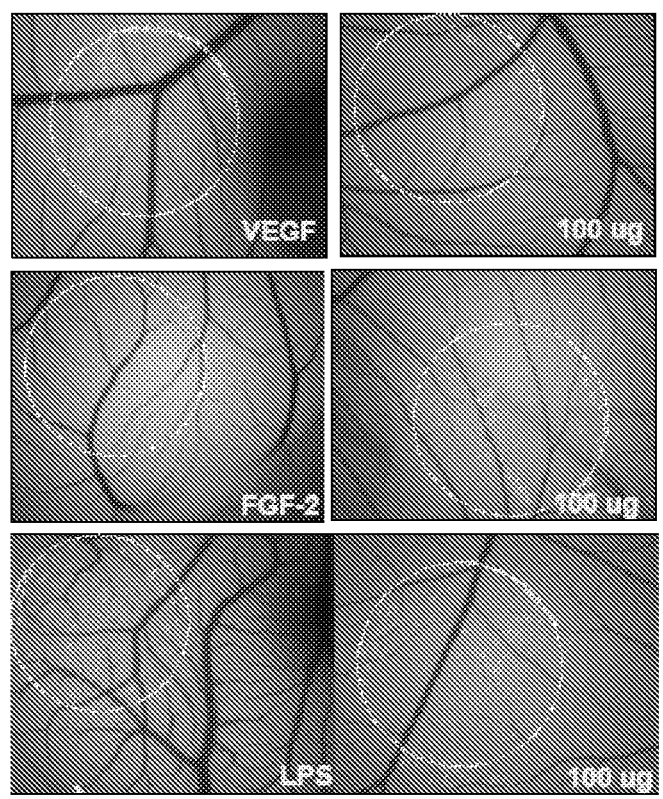
FIG. 19 shows photographs of the CAM of representative chick eggs that were treated with pro-angiogenic factors (left) or pro-angiogenic factors plus 100 μg TM-601. The vascular index density is determined by counting the number of vessels that intersect the circle that is overlayed on the photograph.

VDI = vascular density index
SEM = standard error of measurement
NS = not statistically significant The second laboratory also replicated results that were described in Example 1 showing that TM-601 inhibits VEGF-, bFGF- and LPS-stimulated angiogenesis. As before, this effect was seen in a dose-dependent manner (Table 7 and FIG. 18). All values except the group of embryos stimulated by VEGF-stimulated treated with 0.001 µg TM-601 were statistically significantly decreased compared to the stimulant only control. The photographs depicted in FIG. 19 are representative and show CAMs treated with TM-601 compared to CAMs that were treated with the angiogenesis stimulant only.

TABLE 7

TM-601-mediated inhibition of angiogenesis

| Group | Stimulant | Treatment | Dose (µg) | % inhibition (compared to control) | P value* |
|---|---|---|---|---|---|
| 1 | None | None | None | — | — |
| 2 | VEGF | None | None | 100 | — |
| 3 | VEGF | TM-601 | 0.001 | 88 | NS |
| 4 | VEGF | TM-601 | 0.01 | 70 | <0.05 |
| 5 | VEGF | TM-601 | 0.1 | 68 | <0.05 |
| 6 | VEGF | TM-601 | 1 | 75 | <0.05 |
| 7 | VEGF | TM-601 | 10 | 65 | <0.05 |
| 8 | VEGF | TM-601 | 100 | 67 | <0.05 |
| 1 | None | None | None | — | — |
| 2 | bFGF | None | None | 100 | — |
| 3 | bFGF | TM-601 | 0.001 | 83 | <0.05 |
| 4 | bFGF | TM-601 | 0.01 | 82 | <0.01 |
| 5 | bFGF | TM-601 | 0.1 | 80 | <0.01 |
| 6 | bFGF | TM-601 | 1 | 69 | <0.001 |
| 7 | bFGF | TM-601 | 10 | 64 | <0.01 |
| 8 | bFGF | TM-601 | 100 | 60 | <0.05 |
| 1 | None | None | None | — | — |

TABLE 7-continued

TM-601-mediated inhibition of angiogenesis

| Group | Stimulant | Treatment | Dose (μg) | % inhibition (compared to control) | P value* |
|---|---|---|---|---|---|
| 2 | LPS | None | None | 100 | — |
| 3 | LPS | TM-601 | 0.001 | 87 | <0.05 |
| 4 | LPS | TM-601 | 0.01 | 67 | <0.001 |
| 5 | LPS | TM-601 | 0.1 | 65 | <0.001 |
| 6 | LPS | TM-601 | 1 | 56 | <0.001 |
| 7 | LPS | TM-601 | 10 | 61 | <0.001 |
| 8 | LPS | TM-601 | 100 | 52 | <0.05 |

NS = not statistically significant.
*from stimulant control (group 2)

Figure 21:
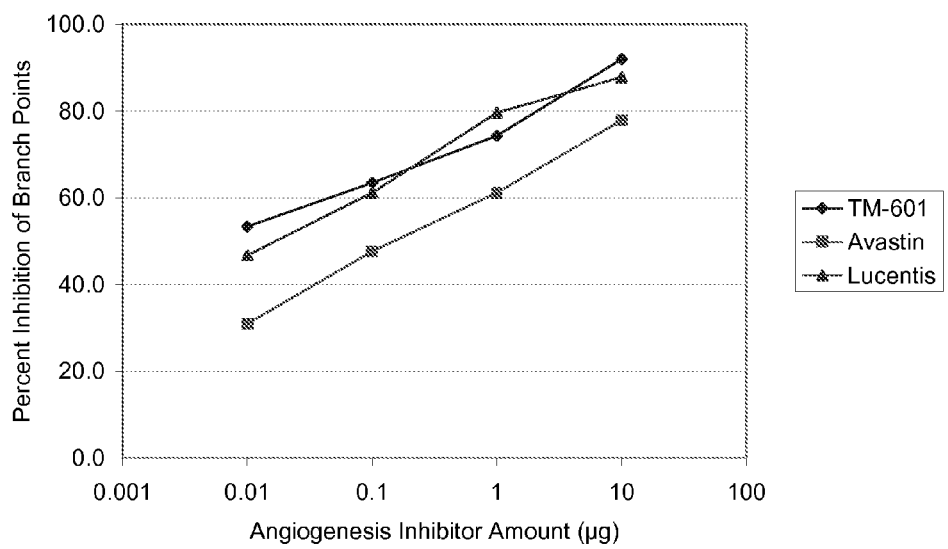
FIG. 21 shows inhibition of VEGF-stimulated angiogenesis by TM-601, Avastin and Lucentis. As represented on a mass basis, TM-601 and Lucentis are the most potent inhibitors of angiogenesis
Figure 22:
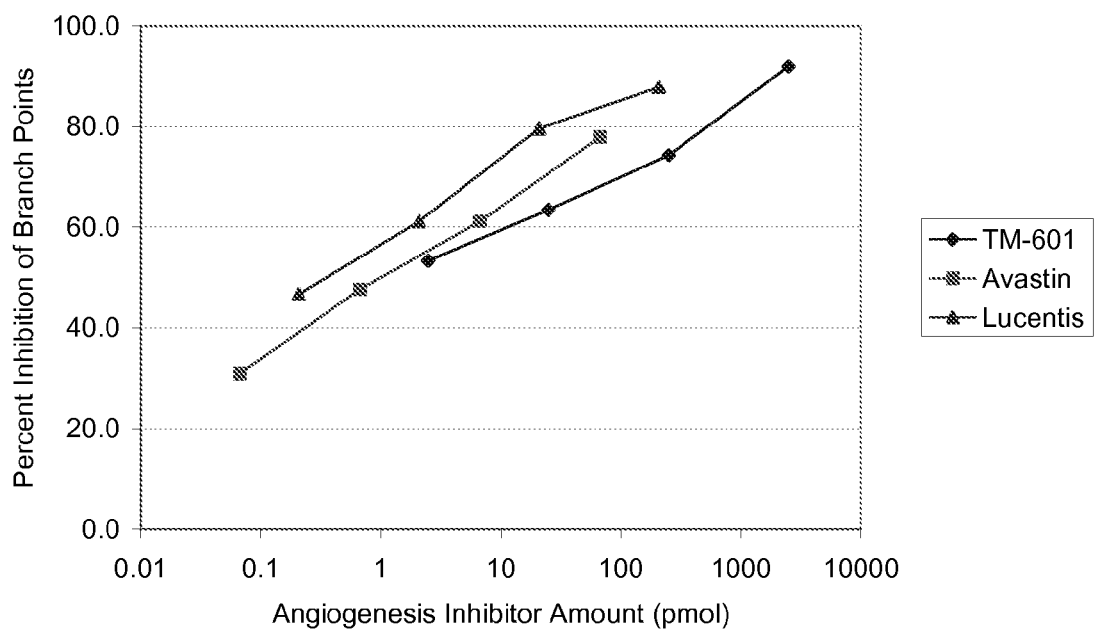
FIG. 22 shows inhibition of VEGF-stimulated angiogenesis by TM-601, Avastin and Lucentis. As represented on a molar basis, TM-601 is less potent than Avastin and Lucentis.

The findings to date show that TM-601 has inhibitory effects on blood vessel formation. However, in order to determine how the potency compares to other anti-angiogenic therapeutics, a CAM experiment was performed in which the inhibition of VEGF-stimulated angiogenesis was measured for TM-601 as well as two approved anti-angiogenic therapies, Avastin and Lucentis. Both Avastin and Lucentis are recombinant humanized anti-VEGF antibodies. They differ in that Lucentis is a smaller molecular weight antibody fragment that was designed to increase its permeability. Comparing the inhibition curves based on the weight of inhibitor added to the CAM, Lucentis and TM-601 were the most potent (greatest inhibition at the lowest mass of inhibitor, FIG. 21). When plotted in terms of molar amount of inhibitor, the curves are shifted due to the relatively larger size of the Avastin antibody and the smaller size of TM-601 (FIG. 22). In terms of molar basis, TM-601 is less potent than Avastin or Lucentis.

Figure 23:
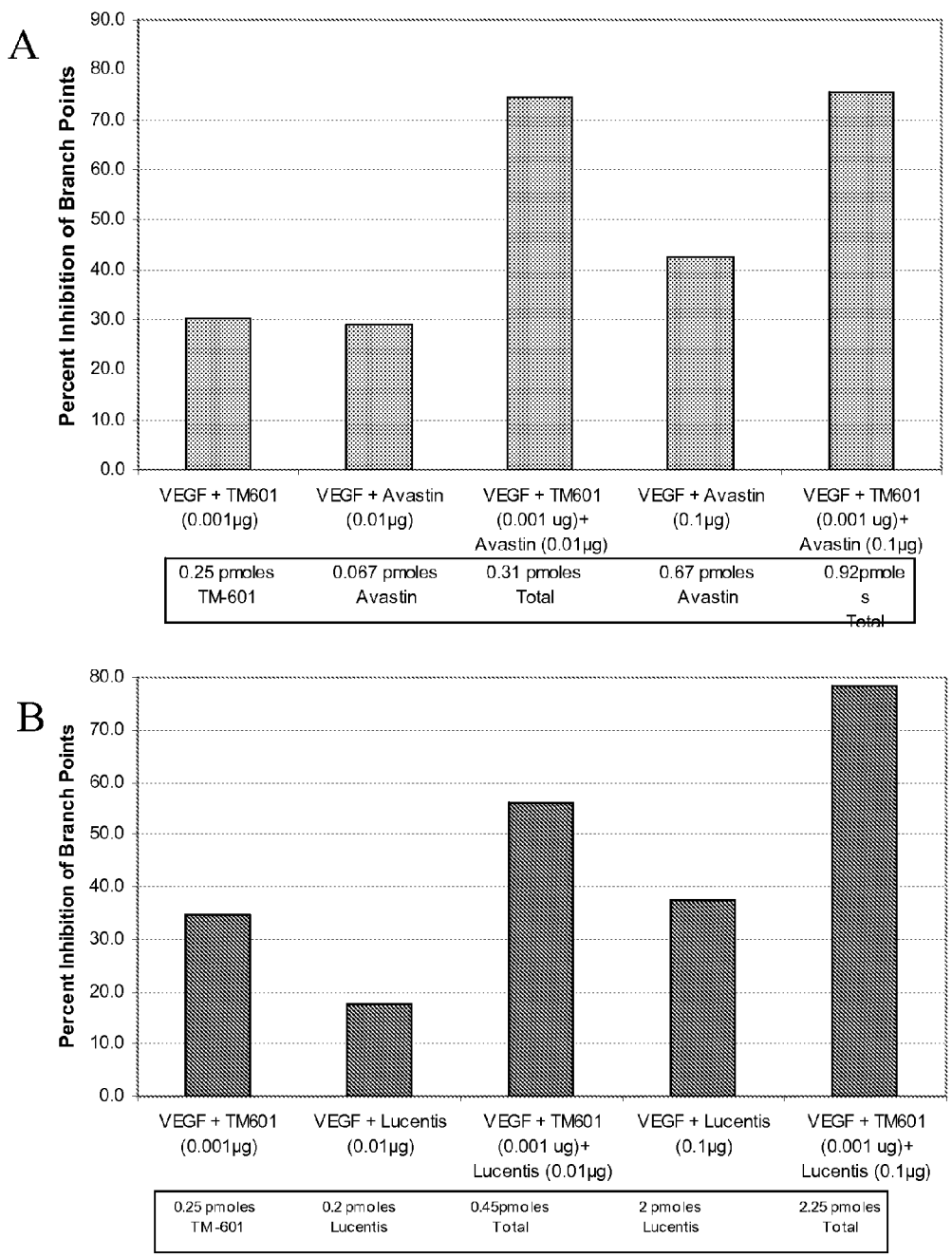
FIG. 23 shows combinatorial effects of TM-601 and Avastin (A) or TM-601 and Lucentis (B) on VEGF-stimulated angiogenesis.
Figure 24:
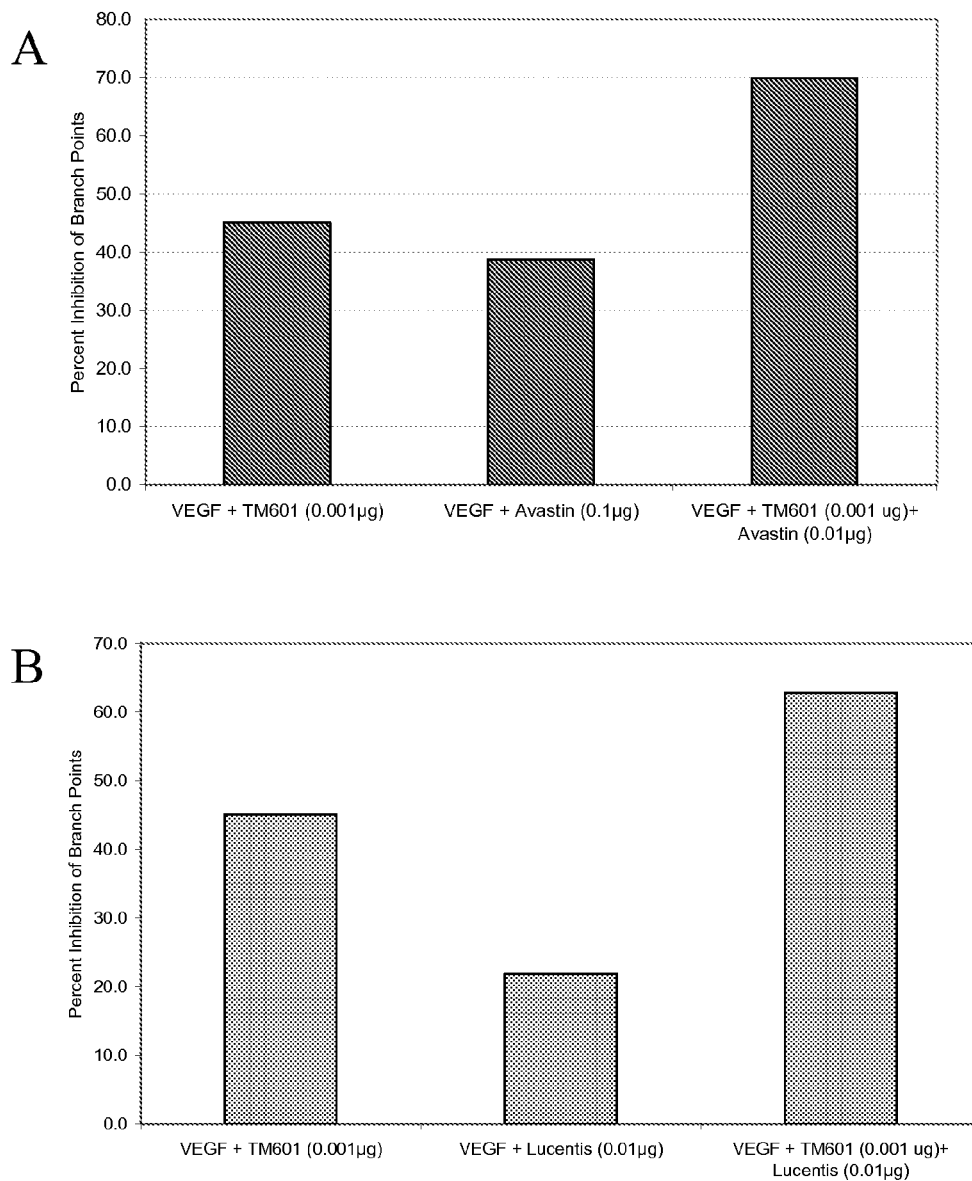
FIG. 24 shows effects of TM-601 and either Avastin (A) or Lucentis (B) on VEGF-stimulated angiogenesis.

Given that TM-601 inhibits angiogenesis that is stimulated by multiple receptor pathways (VEGF, bFGF, LPS, EGF, IL-6, PDGF, TNFα and HGF) and Avastin/Lucentis act only on the VEGF pathway, we next tested whether TM-601 could act together with either Avastin or Lucentis to increase the potency of the anti-angiogenic effect. If so, this effect could either be additive (the sum of each inhibitor alone), or synergistic (more than additive). This experiment was performed twice. As shown in FIGS. 23 and 24, application of TM-601 and either Avastin or Lucentis resulted in more anti-angiogenic activity than either drug alone. It is not yet clear whether this effect results from additive activities or whether synergistic effects occur.

Discussion/Conclusion

Figure 20:
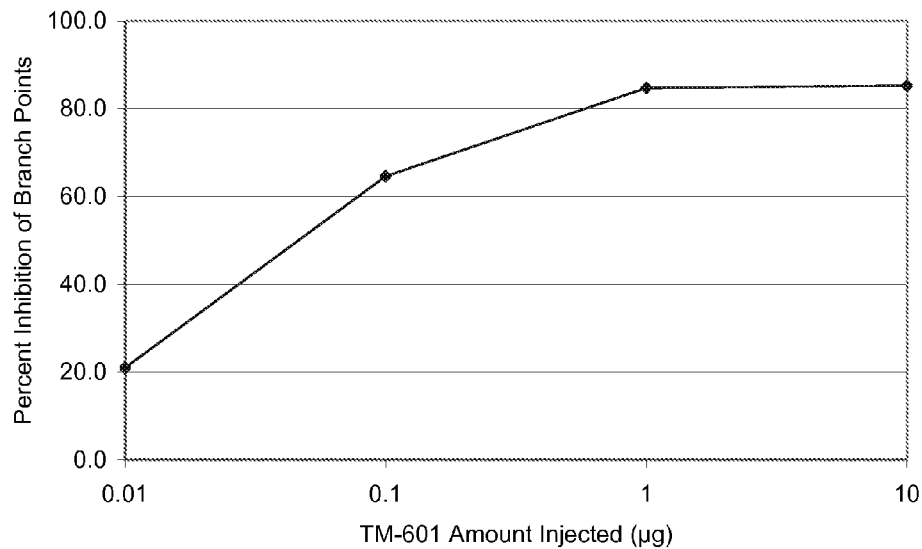
FIG. 20 shows an inhibitory effect of intravenous TM-601 on angiogenesis stimulated by VEGF. A single injection of TM601 at the dose indicated was made into a large vein visible in the chick egg. An inhibitory dose response was observed.
Figure 25:
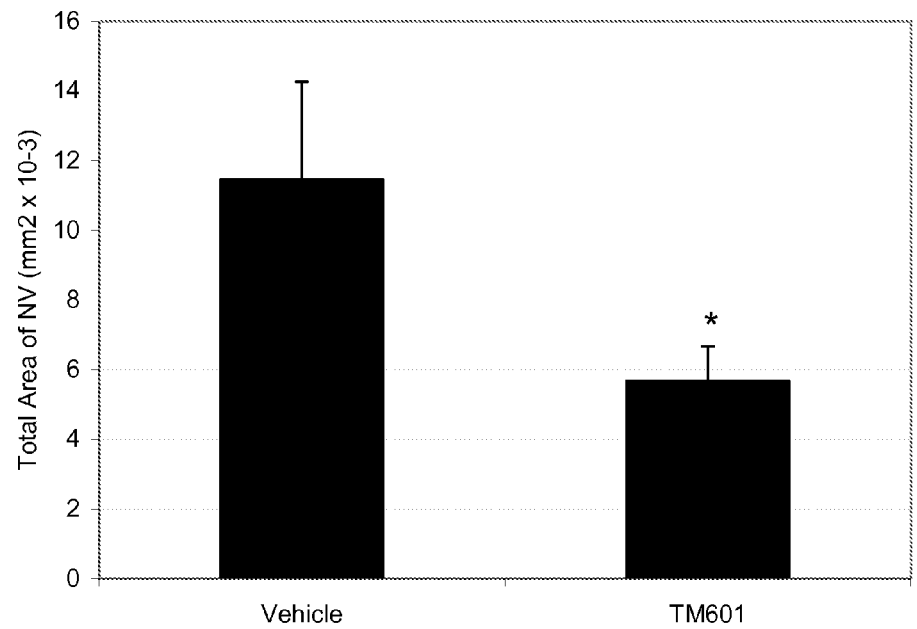
FIG. 25 depicts results from experiments testing the ability of TM-601 to inhibit blood vessel formation in a mouse model of choroidal neovascularization (CNV). Total area of neovascularization (NV) in $mm^2 \times 10^{-3}$ is shown for animals receiving either TM-601 or saline vehicle. A statistically significant decrease in choroidal neovascularization was observed in animals receiving intraocular injections of 50 μg TM-601 on the day of disruption of Bruch's membrane and on day 7 (*$p<0.05$). Choroidal lesions were analyzed on day 14.

The dose dependent inhibitory effect of TM-601 on neovascularization has been replicated at two independent laboratories. Data from one laboratory show that the level of inhibition is more pronounced when pro-angiogenic factors are used to stimulate angiogenesis (FIG. 25) as compared to inhibitory effects on normal developing chick vasculature (FIG. 24) Inhibition of VEGF-stimulated angiogenesis has been observed with locally applied TM-601 (FIG. 18) as well as following a single intravenous injection (FIG. 20).

To determine whether the level of angiogenesis inhibition resulting from TM-601 treatment was similar to other anti-angiogenic compounds, two anti-VEGF antibodies (Avastin and Lucentis) were added individually in the same experiment as TM-601. On a mass basis, TM-601 and Lucentis were the most effective, but Lucentis and Avastin were more effective than TM-601 when expressed on a molar basis. Future experiments directed to further comparing TM-601 and other anti-angiogenic drugs may involve in vivo models such as ocular models of macular degeneration. Such models may allow consideration of clearance rates and adverse effects, which may facilitate determining whether TM-601 is as effective as Avastin and Lucentis.

In another set of experiments, TM-601 was given together with either Avastin or Lucentis. It was not possible with the experiments in the present Example to determine conclusively whether TM-601 acts additively or synergistically with these two anti-VEGF antibodies. The sum of the inhibitory effect of each drug given separately roughly equals the inhibitory effect observed when the two drugs are given simultaneously, which suggests an additive effect.

Nevertheless, a synergistic effect may be suggested by analyzing the combinatorial effects in a different way. When the Avastin dose was increased by 10-fold (0.067 pmoles to 0.67 pmoles), the level of angiogenesis inhibition increased by only 47%, whereas when only 0.25 pmoles of TM-601 was added to 0.067 pmoles of Avastin resulted in a 158% increase (FIG. 23A). Such a response was also observed when combining Lucentis with TM-601 (FIG. 23B). Thus, on a molar basis, addition of TM-601 to either Avastin or Lucentis was significantly more effective at inhibiting angiogenesis than increasing the concentration of either antibody drug alone.

Example 6

Inhibition and Regression of Choroidal Neovascularization by Chlorotoxin

The formation of new blood vessels (angiogenesis) and maintenance of such blood vessels is thought to be an important element of metastasis. In the present Example, the ability of chlorotoxin to inhibit angiogenesis and/or cause regression of existing newly formed blood vessels was evaluated using a choroidal neovascularization assay. When chlorotoxin was administered beginning around the time of induction of blood vessel formation, chlorotoxin caused a significant decrease in new blood vessel formation. In an experimental paradigm in which chlorotoxin was administered several days after blood vessel formation was induced, chlorotoxin caused significant regression of choroidal neovascularization.

Materials and Methods

Choroidal neovascularization (CNV) was induced in mice by photocoagulation with a 530 nm laser. Three burns were delivered to each retina in the 9, 12, and 3 o'clock positions of the posterior pole of the retina. Rupture of Bruch's membrane was judged to be successful when a bubble was produced at the time of laser induction. Only burns for which bubbles were observed were included in this study.

In the first experiment, intravitreal injection of 1 μL, of a 50 mg/mL solution of TM-601 dissolved in saline was injected in one eye (n=17 animals, 49 quantifiable burns) and 1 μL of saline was injected in the fellow eye following laser photocoagulation (n=17 animals, 44 quantifiable burns). Seven days later, the injections were repeated. On day 14 of the study, mice were perfused with fluorescein-labeled dextran ($2\times10^6$ average molecular weight, Sigma) and choroidal flat mounts were prepared and examined by fluorescence microscopy.

In the second experiment, laser photocoagulation was performed on day 1. One group of 10 mice (30 quantifiable burns) were perfused with fluorescein-labeled dextran on day 7 for CNV baseline measurement prior to treatment initiation. The remainder of the mice received an intraocular injection of 1 μL of a 50 mg/mL solution of TM-601 in one eye (n=12 animals, 34 quantifiable burns) and saline in the fellow eye (n=13 animals, 32 quantifiable burns). On day 14, all remaining mice were perfused with fluorescein-labeled dextran and choroidal flat mounts were prepared and examined by fluorescence microscopy.

Sizes of choroidal neovascularization lesions were measured in choroidal flat mounts. After perfusion with fluorescein-labeled dextran, eyes were removed and fixed for 1 hour in 10% buffered formalin. The cornea and lenses were removed and the entire retina was dissected from the eye cup. Radial cuts of the choroids were made from the edge to the equator and the eyecup was flat mounted. Flat mounts were examined by fluorescence microscopy and images were digitized. Image-Pro Plus software (Media Cybernetics) was used to measure the total area of choroidal neovascularization associated with each burn.

Results

Figure 32:
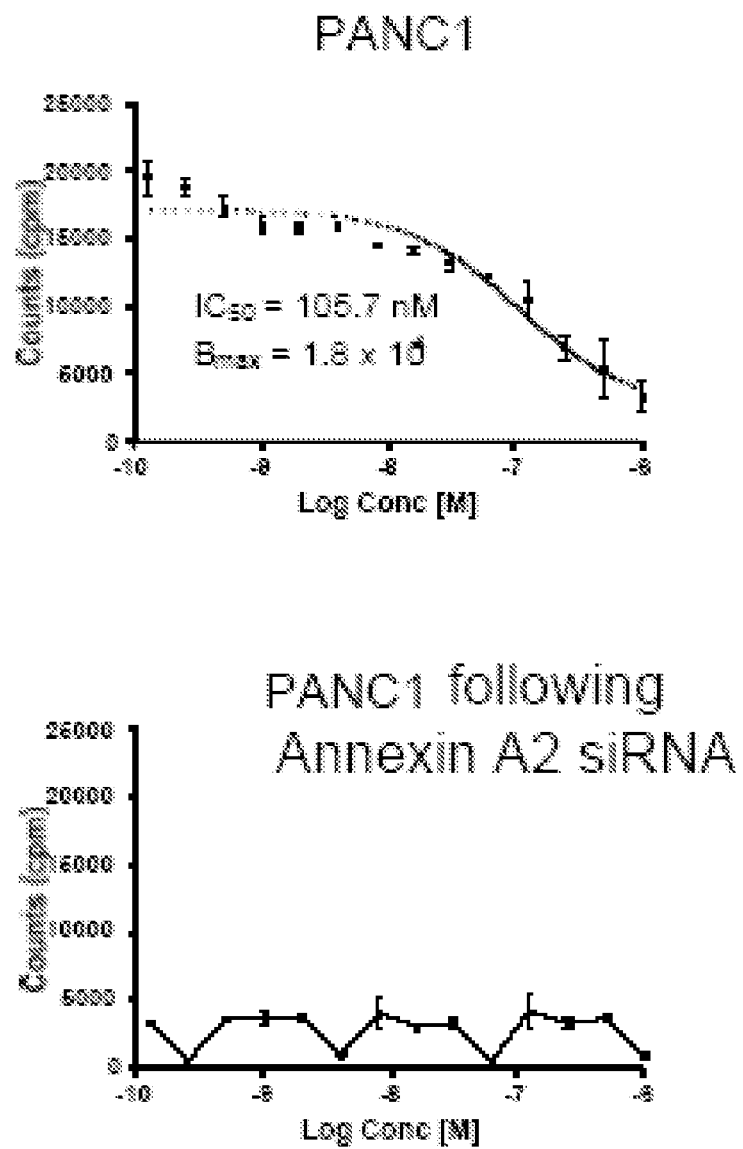
FIG. 32 shows that siRNA knockdown of Annexin A2 expression results in loss of TM-601 binding to the surface of Panc-1 tumor cells, a pancreatic tumor cell line.

Rupture of Bruch's membrane with laser photocoagulation in mice causes choroidal neovascularization (CNV), which mimics many aspects of CNV that occurs in patients with neovascular age-related macular degeneration. To determine whether TM-601 impacts the formation of new blood vessels in this model, intravitreal injections of 50 µg TM-601 were performed on the day of laser photocoagulation (day 1) and on day 7. Control eyes were injected with saline at the same time points. Fourteen days after rupture of Bruch's membrane, choroidal flat mounts from each eye were analyzed. TM-601 treatment was found to significantly decrease the formation of new blood vessels with intraocular TM-601 doses of 50 µg (FIGS. 32 and 34).

Figure 26:
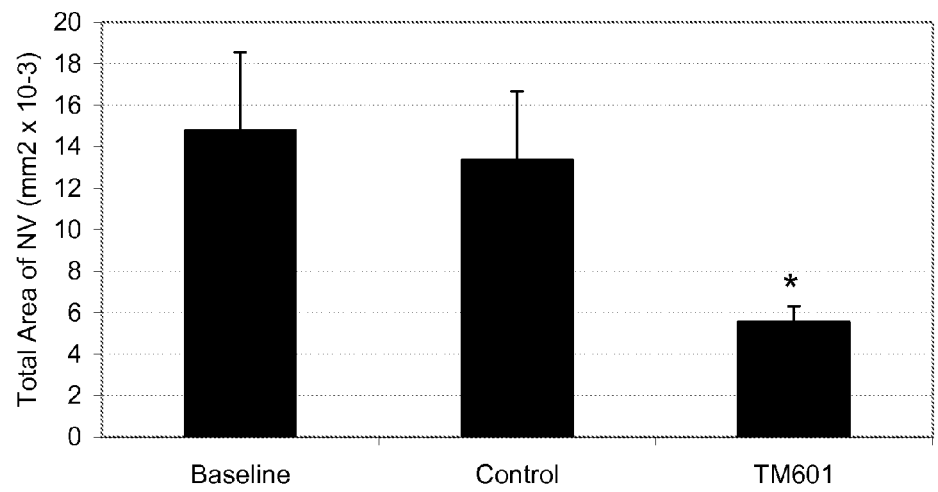
FIG. 26 depicts results from experiments testing the ability of TM-601 to cause regression of existing neovessels in a mouse model of CNV. Total area of neovascularization (NV) in $mm^2 \times 10^{-3}$ is shown for animals receiving either TM-601 or saline vehicle. "Baseline" refers to the measurement taken at day 7 after disruption of Bruch's membrane (i.e., before treatment with TM-601). A statistically significant regression of choroidal neovascularization was observed in animals receiving intraocular injections of 50 μg TM-601 on the day 7 (*$p<0.05$). For "control" and "TM-601" values, choroidal lesions were analyzed on day 14.
Figure 27:
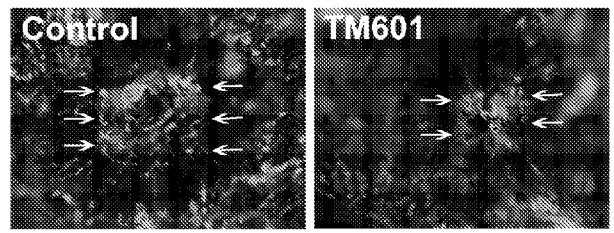
FIG. 27 depicts representative microscopic images showing that intravitreal injection with TM-601 led to decreased blood vessels at the site of laser-induced blood vessels in a mouse model of choroidal neovascularization. Neovascularization was inhibited when TM-601 was administered the same day as laser induction (top panel). Existing neovasculature regressed when TM-601 was administered 7 days after laser induction (bottom panel). On day 14, all mice were perfused with fluorescein-labeled dextran and choroidal flat mounts were prepared and examined by fluorescence microscopy.
Figure 27:
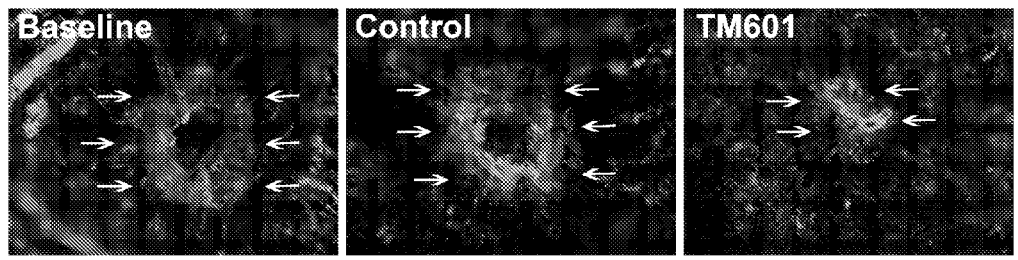

To assess the effect of TM-601 on pre-existing neovasculature in this model, treatment with intraocular injection with 50 µg TM-601 was delayed until 7 days after disruption of Bruch's membrane. At this time point, large sites of neovascularization were already present (see baseline in FIG. 26). A single saline injection on day 7 had no effect on new blood vessel formation measured on day 14 (control in FIG. 33), whereas a single injection of TM-601 significantly caused regression of CNV (FIGS. 26 and 27).

Discussion/Conclusion

The present Example demonstrates that locally administered TM-601 can significantly suppress CNV and cause regression of CNV. Regression of new blood vessels has been shown to occur via apoptosis within CNV lesions. (See, e.g., Lima R. et al. 2006. Recombinant non-collagenous domain of a2(IV) collagen causes involution of choroidal neovascularization by inducing apoptosis. *Journal of Cellular Physiology* 208: 161-166, the entire contents of which are herein incorporated by reference in their entirety.) The CNV mouse model mimics a disease state for the wet form of macular degeneration. The intravitreal route of administration used in this study may be clinically relevant, since it is the route used for administering Lucentis®, a clinically approved therapy for macular degeneration.

Example 7

Bioavailability and Anti-Angiogenic Effects of PEGylated Chlorotoxin

In the present Example, PEGylated chlorotoxin was studied to determine if the half-life of chlorotoxin in vivo could be increased. Anti-angiogenic effects of PEGylated chlorotoxin was also examined.

Materials and Methods
PEGylation

TM-601 was PEGylated at the N-terminus of the peptide via reductive animation using a polydispersed, linear, 40 kDa PEG-propionaldehyde (DowPharma).

Half-Life Measurements of TM-601

Non-tumor-bearing C57BL/6 mice were injected with TM-601 (at a dose of approximately 2 mg/kg) intravenously by a single tail vein injection. Blood samples were obtained at various timepoints, and levels of TM-601 were determined by ELISA using an anti-TM-601 antibody.

Mouse Matrigel Plug

Matrigel Matrix High Concentration (from BD Biosciences) was mixed with 100 ng/ml VEGF, 100 ng/ml bFGF, and 3 ng/ml heparin at 4° C. Eight-week old female C57BL/6 mice were randomly assigned to each groups with 6 mice in each group. Each mouse received two 500 µL Matrigel plugs injected bilaterally in subcutaneous tissue. To form a round shaped plug, a wide subcutaneous pocket was formed by swaying the needlepoint right and left after a routine subcutaneous insertion. The injection was performed rapidly with a 21-25 G needle to ensure the entire contents were delivered into the plug. Matrigel plugs were implanted on Day 0 of the study and treatment began on Day 1. Animals were dosed with intravenous injections with either vehicle (saline), TM-601, or PEGylated TM-601. Three dosing regimens were used: once a week for two weeks (once on D1 and once on D8; "Q7D×2"), twice a week for two weeks (on D1, D4, D8, and D11; "Q3D×2/2"), and five times a week for two weeks (on D1, D2, D3, D4, D5, D8, D9, D10, D11, and D12; "Q1D×5/2"). Plugs were collected after 14 days. Mice were euthanized and the skin over the plugs was pulled back. Plugs were dissected out, fixed, and embedded in paraffin for histological analysis. Three sections of 5 µm thickness from each evaluable plug were immunostained with a CD31 antibody and counterstained with hematoxylin & eosin. Blood vessel counts in a cross sectional area of each matrigel plug was analyzed under a microscope.

Results/Discussion

Figure 28:
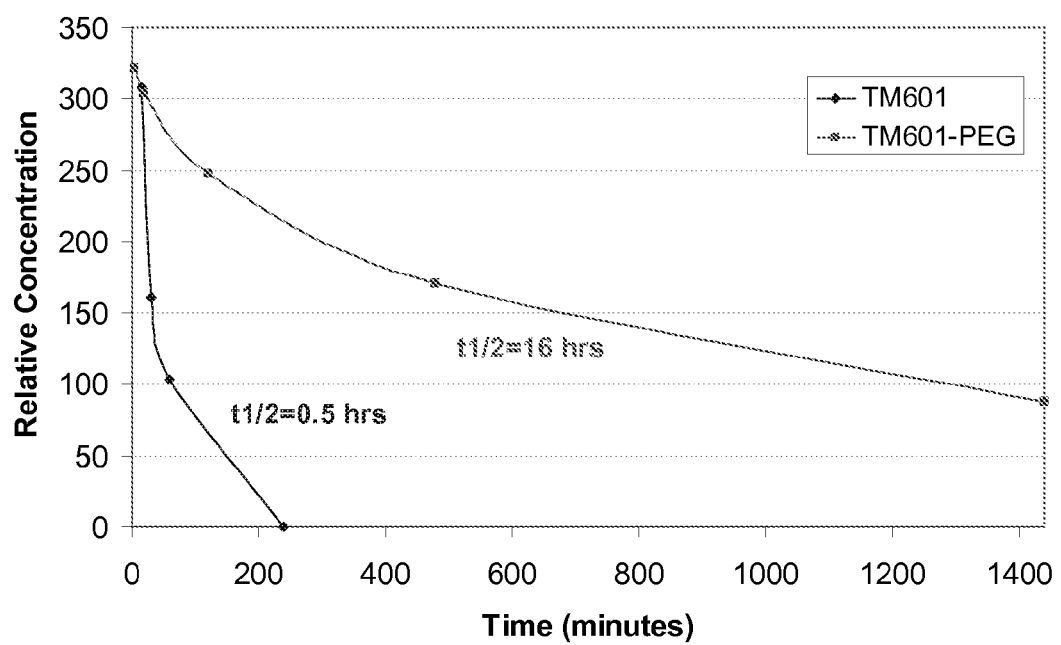
FIG. 28 shows the half-lives of PEGylated chlorotoxin (TM-601-PEG) as compared to unmodified TM-601 in intravenously injected non-cancerous mice. PEGylation increased the half-life of TM601 by approximately 32-fold.

As shown in FIG. 28, PEGylated TM-601 exhibited an increased half-life in vivo as compared to unmodified TM-601. PEGylation increased the half life of TM-601 approximate 32-fold, that is, approximately 25 minutes (TM-601) to approximately 16 hrs (TM-601-PEG).

Increased half life translated into the ability to dose the animals less frequently in a model of angiogenesis. In mouse Matrigel plug assays, animals were dosed according to a variety of schedules with either TM-601 or PEGylated TM-601 (TM-601-PEG). Microvessel densities were measured and reduction of such densities was interpreted to signify anti-angiogenic effects.

Figure 29:
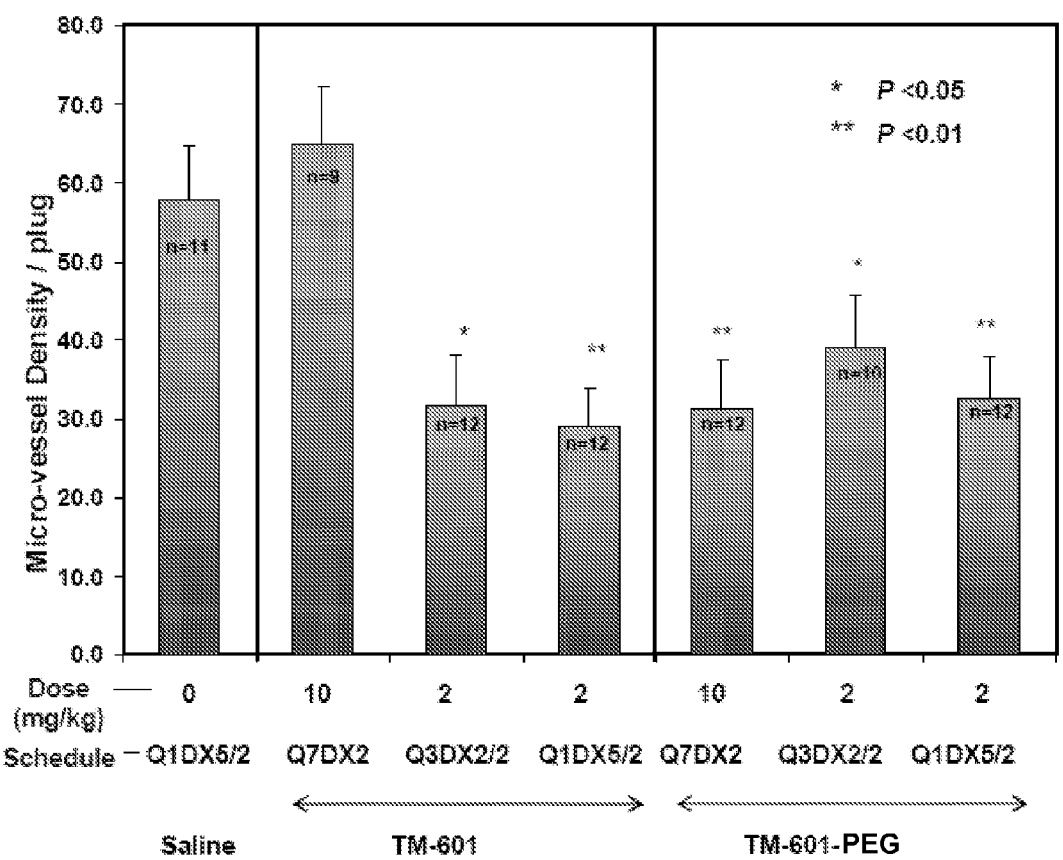
FIG. 29 shows that PEGylated TM-601 can achieve anti-angiogenic effects with less frequent dosing than unmodified TM-601 in a mouse CNV model. Microvessel density in a CNV model was plotted for various dosing regimens for unmodified TM-601 or for PEGylated TM-601.

Both TM-601 and TM-601-PEG had anti-angiogenic effects with the two most frequent dosing schedules tested (twice a week for two weeks, "Q3D×2/2"; and five times a week for two weeks, "Q1D×5/2") (FIG. 29). Whereas TM-601 did not exhibit any anti-angiogenic effects with the least frequent dosing schedule tested (once a week for two weeks, "Q7D×2") treatment with TM-601-PEG with such a dosing schedule resulted in a significant reduction of microvessel density (FIG. 29).

Without wishing to be bound by any particular theory, the ability to dose animals less frequently may be due to availability of TM-601-PEG for a longer period of time as compared to TM-601. Such increased availability could result in longer exposure at sites of new blood vessel formation, allowing more prolonged effects.

Example 8

Anti-Angiogenic Effects of Chlorotoxin Delivered by Subconjunctival Injections

Some ocular disorders, such as the wet form of macular degeneration, involve aberrant angiogenesis. In this Example, anti-angiogenic effects of TM-601 were tested in an animal eye model for angiogenesis (in particular, a mouse choroidal neovascularization model). TM-601 was delivered by subconjunctival injection, a route that is commonly used to administer to the eye, and its efficacy against angiogenesis was examined.

Materials and Methods

Mouse Choroidal Neovascularization Model

Choroidal neovascularization (CNV) in mice was induced by 530 nm laser photocoagulation. Three burns were delivered to each retina in the 9, 12 and 3 o'clock positions of the posterior pole of the retina. Successful rupture of Bruch's membrane was evident when production of a bubble occurred at the time of the laser induction. Only burns in which a bubble was observed were included in the study.

Subconjunctival Injections

Periocular (subconjunctival) injections of 5 µL of TM-601 dissolved in saline were made in one eye on day 1 and day 8. TM-601 was prepared at concentrations of about 2, 10, 50 and 200 mg/ml such that the total doses were about 10, 50, 250 and 1000 µg respectively. One group of animals was injected with the same volume of saline. On day 14 of the study, mice were perfused with fluorescein-labeled dextran ($2\times10^6$ average molecular weight, Sigma) and choroidal flat mounts were prepared and examined by fluorescence microscopy. The fellow eye (non-treated eye) served as a control and did not receive injections.

Measurement of Choroidal Neovascularization

Sizes of choroidal neovascularization lesions were measured in choroidal flat mounts. After perfusion with fluorescein-labeled dextran, eyes were removed and fixed for 1 hour in 10% buffered formalin. The cornea and lenses were removed and the entire retina was dissected from the eye cup. Radial cuts of the choroids were made from the edge to the equator and the eyecup was flat mounted. Flat mounts were examined by florescence microscopy and images were digitized. Image-Pro Plus software (Media Cybernetics) was used to measure the total area of choroidal neovascularization associated with each burn.

Results and Discussion

Figure 30:
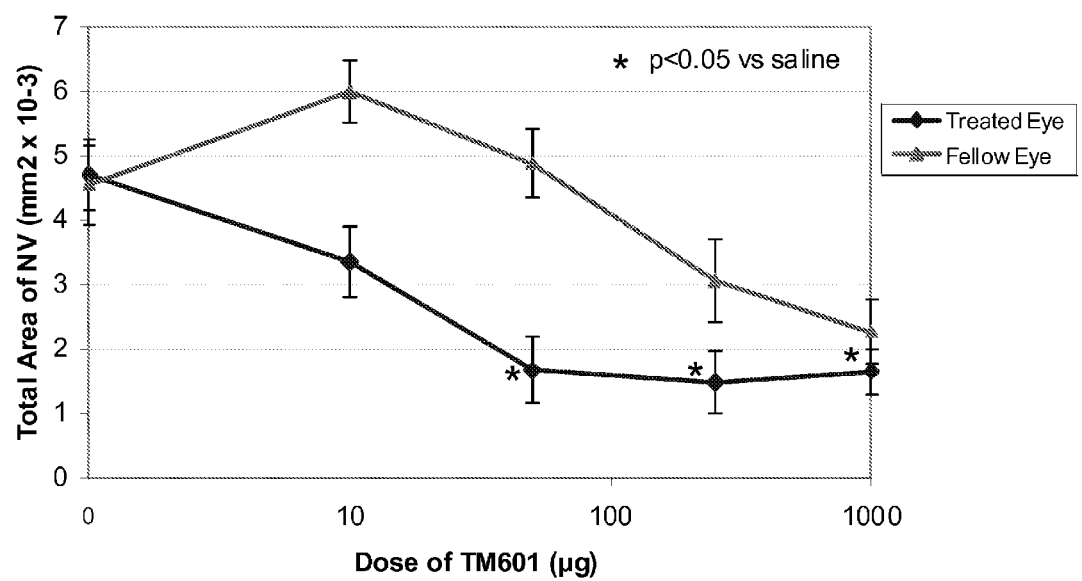
FIG. 30 shows a dose-response curve for TM-601 administered by subconjunctival injection in a mouse CNV model.

Choroidal neovascularization was induced in mouse eyes and mice were treated in one eye with TM-601 injected into subconjunctiva. The untreated eye served as a control. As shown in FIG. 30, treatment with TM-601 lead to dose-dependent decreases in the total area of neovascularization. Anti-angiogenic effects of subconjunctivally-delivered TM-601 appeared to maximize at around 60 µg of TM-601 (roughly equivalent to approximately 20-30 mg/kg). These decreases were significantly different when compared to saline-injected controls ($p<0.05$). Interestingly, total area of neovascularization in control uninjected eyes ("fellow eyes") also appeared to decrease in a dose-dependent manner, though the decreases were not as great as the decreases observed for injected eyes. Without wishing to be bound by any particular theory, such observed effects may be a result of TM-601 spreading from the site of injection in the other eye. Nevertheless, the observed effects in uninjected fellow eyes may be artifactual.

These results indicate that TM-601 exerts anti-angiogenic effects in a dose dependent manner when delivered by subconjunctival injection.

Example 9

Topical Application of TM-601-Containing Eye Drops

Example 8 demonstrated that TM-601 can be delivered to the eye and block new blood vessel formation in the eye. In Example 8, TM-601 was delivered by subconjunctival injection. Other routes of administration that have been tested for delivery of TM-601 include intraocular (see Example 6), intravitreal (see Example 6), and intravenous (see Example 2), all of which have successfully been used to deliver anti-angiogenically effective TM-601.

In the present Example, another route of administration to the eye was explored. TM-601 was delivered topically in the form of eye drops and tested for anti-angiogenic effects. Topical administration offers the advantage of being noninvasive. Eye drops may allow an alternative method of delivering TM-601 to eye for treatment of disorders such as angiogenesis-related disorders (e.g., wet macular degeneration).

Materials and Methods

The mouse model for choroidal neovascularization used in this Example and procedures for measuring CNV were as described in Example 8.

TM-601 was given via topical eye drops three times a day throughout the study. TM-601 was dissolved in a solution containing 70% dextran and 0.3% hypromellose (active ingredients) at a concentration of either about 1, 5 or 25 mg/mL. Thus, with each drop of about 10 µL, the dose was about 10, 50 or 250 µg. As in Example 8, on day 14, all mice were perfused with fluorescein-labeled dextran and choroidal flat mounts were prepared and examined by fluorescence microscopy.

Results and Discussion

Figure 31:
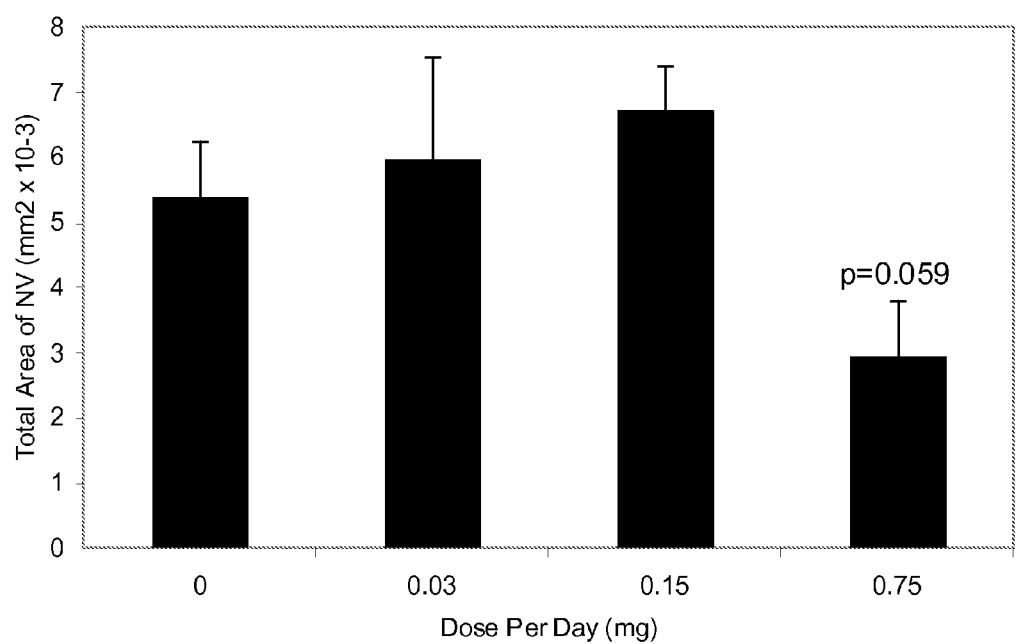
FIG. 31 shows results on neovascularization in a mouse CNV model when TM-601 is administered by topical Application of Eye Drops.

A total of approximately 0, 0.03 mg, 0.15 mg, or 0.75 mg TM-601 was delivered by eye drops to mice in which choroidal neovascularization had been induced. As shown in FIG. 31, topically delivered TM-601 was effective at the highest dose tested (750 µg; approximately 25-40 mg/kg). No toxicity was observed at any of the doses tested. These results demonstrate that TM-601 can block blood vessel formation when delivered via eye drops.

Example 10

Chlorotoxin Binding Partners

To understand better the mechanism(s) by which chlorotoxin exerts its anti-angiogenic effects, the inventors are conducting a series of experiments directed to identifying binding partners for chlorotoxin. Previous experiments indicated that chlorotoxin binds specifically to an antigen (or antigens) on surfaces of tumor cells. The inventors have designed experiments to elucidate the identity of such an antigen or antigens.

Without wishing to be bound by any particular theory, the inventors propose that relevant properties of a protein or antigen that specifically interacts with chlorotoxin may include one or more of: 1) co-precipitation with chlorotoxin in pull-down assays, 2) lack of binding to cell lines that do not bind chlorotoxin, 3) presence in plasma membrane, 4) absence of interaction with control reagents such as beads and/or non-chlorotoxin derived peptides, 5) interaction with cell lines that may be disrupted in a competitive manner by TM-601 peptide, 6) diminished chlorotoxin binding to cells when the protein/antigen is knocked out and/or down in such cells and/or 7) restored chlorotoxin binding to such knockout and/or knockdown cells when expression of the protein/antigen is added back.

Protein cross-linking experiments are being used to identify proteins that may bind to chlorotoxin. TM-601 will be allowed to bind to U87 glioma cells. Cells are treated with a membrane impermeable agent to crosslink proteins at the surfaces of cells that may bind to chlorotoxin. Total cell lysates (which will include protein-chlorotoxin complexes) are separated on a polyacrylamide gel by electrophoresis. Crosslinked complexes are probed on a Western blot using affinity purified anti-TM-601 antibodies. Potential binders of chlorotoxin will be identified using bands on the Western blot.

Pull-down experiments are also performed using TM-602, a synthetic biotinylated version of chlorotoxin. Similar to the protein cross-linking experiments, TM-602 are allowed to bind to U87 glioma cells. Cells are treated to crosslink surface proteins with chlorotoxin. Complexes are pulled down from total cell lysates using beads to which anti-TM-601 antibodies are linked. (Anti-TM-601 antibodies also recognize TM-602.) Pulled-down complexes are then separated on a polyacrylamide gel by electrophoresis. Proteins on the gel represent potential binders to chlorotoxin. Some protein bands are cut from the gel and sequenced by gas chromatography/mass spectrometry.

Initial pull down experiments identified several proteins as a potential binder of chlorotoxin. Annexin A2, a protein that associates with cell membranes, was among the potential binding partners of chlorotoxin. Annexin A2 was pulled down in complexes by anti-TM-601 antibodies and detected on Western blots using anti-Annexin A2 antibodies.

To examine the possibility that Annexin A2 binds chlorotoxin, knock-down experiments were performed in which siRNA directed against expression of Annexin A2 was used. Chlorotoxin binding to cells knocked down for Annexin A2 were then evaluated.

Binding of tracer amounts of radiolabeled TM-601 to surfaces of cell was performed at 4° C. In addition, increasing amounts of non-labeled TM-601 were added to show competition for surface receptors. Binding was either performed to untreated Panc-1 cells or Panc-1 cells that were transfected with a set of siRNA that decrease Annexin A2 in the cell. As shown in FIG. 32, siRNA knockdown of Annexin A2 was found to significantly decrease the surface binding of TM-601 to the cell surface.

Annexin A2 is expressed on surfaces of endothelial cells and is overexpressed in certain tumor types. Annexin A2 has been characterized as a docking station that regulates the conversion of pro- and/or anti-angiogenic proteins such as plasminogen and plasmin.

It appears that there is a specific interaction between Annexin A2 and chlorotoxin in vivo. Additional experiments are being conducted to clarify whether Annexin A2 binds to chlorotoxin in vivo. Without wishing to be bound by any particular theory, it is proposed that chlorotoxin may mediate some of its anti-angiogenic effects by binding to Annexin A2, thereby altering Annexin A2's regulation of factors involved in angiogenesis.

Annexin A2 has been implicated in a wide range of roles. Chlorotoxin's antio-angiogenic effects and potential interaction with Annexin A2 are interesting in light of Annexin A2's proposed role in regulating the plasmin/plasminogen activator system. Annexin A2 promotes generation of plasmin (a serine protease) on endothelial cells. This action may be mediated by Annexin A2 binding to tPA (tissue plasminogen activator) and to plasminogen. Plasmin overproduction has been linked to angiogenesis and metastasis. At the same time, plasmin-cleaved β-2-Glycoprotein 1 has been observed to inhibit angiogenesis. Though the exact mechanistic details involving chlorotoxin, Annexin A2, and downstream regulated proteins such as plasmin remain to be clarified, data presented herein provide an interesting link between chlorotoxin's observed effects on angiogenesis and its potential binding partner.

Given that chlorotoxin is effective therapy for a variety of diseases and conditions (as established here and in the art), the present findings establish that Annexin A2, as a potential interaction partner of chlorotoxin, is a desirable target for identifying new pharmaceutical agents. Agents that bind to and/or modulate Annexin A2, as chlorotoxin potentially does, may serve as useful therapeutic agents. Screening for such modulators may uncover new therapies, some of which may have different characteristics than chlorotoxin. Such new therapies may allow, for example, treatment and/or amelioration of a broader range of diseases, targeting to different cell types, dosing via different regimens and routes of administration, etc.

Other potential binders of chlorotoxin (identified, for example, by initial pull-down experiments) may also be investigated in additional experiments.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method of identifying agents that compete for binding to Annexin A2 with a chlorotoxin polypeptide comprising SEQ ID NO: 1, said method comprising:

(a) providing a sample comprising cells that express Annexin A2;

(b) contacting the sample with a test agent in the presence of said chlototoxin polypeptide;

(c) determining whether binding of the test agent inhibits binding of said chlototoxin polypeptide to the cells that express Annexin A2; and (d) identifying the test agent as an agent that competes for binding to Annexin A2 with chlorotoxin if binding of the test agent inhibits binding of said chlototoxin polypeptide to the cells that express Annexin A2.

2. The method of claim 1, further comprising determining whether the test agent modulates Annexin A2 function.

* * * * *

SEQUENCE LISTING

```
<160> NUMBER OF SEQ ID NOS: 95

<210> SEQ ID NO 1
<211> LENGTH: 36
<212> TYPE: PRT
<213> ORGANISM: Leiurus quinquestriatus
<220> FEATURE:
<221> NAME/KEY: misc_feature
<223> OTHER INFORMATION: Chlorotoxin

<400> SEQUENCE: 1

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35
```

```
<210> SEQ ID NO 2
<211> LENGTH: 42
<212> TYPE: PRT
<213> ORGANISM: Leiurus quinquestriatus

<400> SEQUENCE: 2

His His His His His His Met Cys Met Pro Cys Phe Thr Thr Asp His
1               5                   10                  15

Gln Met Ala Arg Lys Cys Asp Asp Cys Cys Gly Gly Lys Gly Arg Gly
            20                  25                  30

Lys Cys Tyr Gly Pro Gln Cys Leu Cys Arg
        35                  40

<210> SEQ ID NO 3
<211> LENGTH: 37
<212> TYPE: PRT
<213> ORGANISM: Leiurus quinquestriatus

<400> SEQUENCE: 3

Tyr Met Cys Met Pro Cys Phe Thr Thr Asp His Gln Met Ala Arg Lys
1               5                   10                  15

Cys Asp Asp Cys Cys Gly Gly Lys Gly Arg Gly Lys Cys Tyr Gly Pro
            20                  25                  30

Gln Cys Leu Cys Arg
        35

<210> SEQ ID NO 4
<211> LENGTH: 39
<212> TYPE: PRT
<213> ORGANISM: Leiurus quinquestriatus

<400> SEQUENCE: 4

Tyr Ser Tyr Met Cys Met Pro Cys Phe Thr Thr Asp His Gln Met Ala
1               5                   10                  15

Arg Lys Cys Asp Asp Cys Cys Gly Gly Lys Gly Arg Gly Lys Cys Tyr
            20                  25                  30

Gly Pro Gln Cys Leu Cys Arg
        35

<210> SEQ ID NO 5
<211> LENGTH: 36
<212> TYPE: PRT
<213> ORGANISM: Artificial sequence
<220> FEATURE:
<223> OTHER INFORMATION: Chlorotoxin variant

<400> SEQUENCE: 5

Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Phe Gly Pro Gln
            20                  25                  30

Cys Leu Cys Arg
        35

<210> SEQ ID NO 6
<211> LENGTH: 35
<212> TYPE: PRT
<213> ORGANISM: Artificial sequence
<220> FEATURE:
<223> OTHER INFORMATION: Chlorotoxin variant
```

```
<400> SEQUENCE: 6

Arg Cys Lys Pro Cys Phe Thr Thr Asp Pro Gln Met Ser Lys Lys Cys
1               5                   10                  15

Ala Asp Cys Cys Gly Gly Lys Gly Lys Gly Lys Cys Tyr Gly Pro Gln
            20                  25                  30

Cys Leu Cys
        35

<210> SEQ ID NO 7
<211> LENGTH: 38
<212> TYPE: PRT
<213> ORGANISM: Artificial sequence
<220> FEATURE:
<223> OTHER INFORMATION: Chlorotoxin variant

<400> SEQUENCE: 7

Arg Cys Ser Pro Cys Phe Thr Thr Asp Gln Gln Met Thr Lys Lys Cys
1               5                   10                  15

Tyr Asp Cys Cys Gly Gly Lys Gly Lys Gly Lys Cys Tyr Gly Pro Gln
            20                  25                  30

Cys Ile Cys Ala Pro Tyr
        35

<210> SEQ ID NO 8
<211> LENGTH: 7
<212> TYPE: PRT
<213> ORGANISM: Leiurus quinquestriatus
<220> FEATURE:
<221> NAME/KEY: misc_feature
<223> OTHER INFORMATION: Derivative of Chlorotoxin: amino acid residues
      23-29

<400> SEQUENCE: 8

Lys Gly Arg Gly Lys Ser Tyr
1               5

<210> SEQ ID NO 9
<211> LENGTH: 7
<212> TYPE: PRT
<213> ORGANISM: Leiurus quinquestriatus
<220> FEATURE:
<221> NAME/KEY: misc_feature
<223> OTHER INFORMATION: Derivative of Chlorotoxin: amino acid residues
      8-14

<400> SEQUENCE: 9

Thr Asp His Gln Met Ala Arg
1               5

<210> SEQ ID NO 10
<211> LENGTH: 9
<212> TYPE: PRT
<213> ORGANISM: Artificial sequence
<220> FEATURE:
<223> OTHER INFORMATION: Chlorotoxin alpha peptide

<400> SEQUENCE: 10

Thr Asp His Gln Met Ala Arg Lys Ser
1               5

<210> SEQ ID NO 11
<211> LENGTH: 9
<212> TYPE: PRT
<213> ORGANISM: Artificial sequence
<220> FEATURE:
<223> OTHER INFORMATION: Variant of chlorotoxin alpha peptide
```

-continued

<400> SEQUENCE: 11

Thr Ala His Ala Met Ala Arg Lys Ser
1               5

<210> SEQ ID NO 12
<211> LENGTH: 36
<212> TYPE: PRT
<213> ORGANISM: Artificial sequence
<220> FEATURE:
<223> OTHER INFORMATION: Variant peptide of chlorotoxin

<400> SEQUENCE: 12

Met Cys Met Pro Cys Phe Thr Thr Ala His Ala Met Ala Arg Lys Cys
1               5                   10                  15

Asp Asp Cys Cys Gly Gly Lys Gly Arg Cys Lys Cys Tyr Gly Pro Gln
            20                  25                  30

Cys Leu Cys Arg
        35

<210> SEQ ID NO 13
<211> LENGTH: 9
<212> TYPE: PRT
<213> ORGANISM: Artificial
<220> FEATURE:
<223> OTHER INFORMATION: motif for chlorotoxin derivatives
<220> FEATURE:
<221> NAME/KEY: Variant
<222> LOCATION: (3)..(3)
<223> OTHER INFORMATION: Xaa = Asp or Glu
<220> FEATURE:
<221> NAME/KEY: Variant
<222> LOCATION: (4)..(4)
<223> OTHER INFORMATION: Xaa = Ala, Arg, Asn, Asp, Cys, Gln, Glu, Gly,
      His, Ile, Leu, Lys, Met, Phe, Pro, Ser, Thr, Trp, Tyr or Val
<220> FEATURE:
<221> NAME/KEY: Variant
<222> LOCATION: (5)..(5)
<223> OTHER INFORMATION: Xaa = Asn or Gln
<220> FEATURE:
<221> NAME/KEY: Variant
<222> LOCATION: (7)..(7)
<223> OTHER INFORMATION: Xaa = Ser, Thr, or Ala
<220> FEATURE:
<221> NAME/KEY: Variant
<222> LOCATION: (8)..(8)
<223> OTHER INFORMATION: Xaa = His, Lys, or Arg

<400> SEQUENCE: 13

Thr Thr Xaa Xaa Xaa Met Xaa Xaa Lys
1               5

<210> SEQ ID NO 14
<211> LENGTH: 9
<212> TYPE: PRT
<213> ORGANISM: Leiurus quinquestriatus

<400> SEQUENCE: 14

Thr Thr Asp His Gln Met Ala Arg Lys
1               5

<210> SEQ ID NO 15
<211> LENGTH: 35
<212> TYPE: PRT
<213> ORGANISM: Mesobuthus tamulus

<400> SEQUENCE: 15

Arg Cys Lys Pro Cys Phe Thr Thr Asp Pro Gln Met Ser Lys Lys Cys
1               5                   10                  15

Ala Asp Cys Cys Gly Gly Lys Gly Lys Gly Lys Cys Tyr Gly Pro Gln
            20                  25                  30

Cys Leu Cys
        35

<210> SEQ ID NO 16
<211> LENGTH: 34
<212> TYPE: PRT
<213> ORGANISM: Artificial sequence
<220> FEATURE:
<223> OTHER INFORMATION: Small Toxin consensus sequence
<220> FEATURE:
<221> NAME/KEY: MISC_FEATURE
<222> LOCATION: (2)..(2)
<223> OTHER INFORMATION: Xaa can be Met or Lys
<220> FEATURE:
<221> NAME/KEY: MISC_FEATURE
<222> LOCATION: (9)..(9)
<223> OTHER INFORMATION: Xaa can be His or Pro
<220> FEATURE:
<221> NAME/KEY: MISC_FEATURE
<222> LOCATION: (16)..(16)
<223> OTHER INFORMATION: Xaa can be Asp or Ala

<400> SEQUENCE: 16

Cys Xaa Pro Cys Phe Thr Thr Asp Xaa Gln Met Ala Lys Lys Cys Xaa
1               5                   10                  15

Asp Cys Cys Gly Gly Lys Gly Lys Gly Lys Cys Tyr Gly Pro Gln Cys
            20                  25                  30

Leu Cys

<210> SEQ ID NO 17
<211> LENGTH: 38
<212> TYPE: PRT
<213> ORGANISM: Leiurus quinquestriatus

<400> SEQUENCE: 17

Arg Cys Ser Pro Cys Phe Thr Thr Asp Gln Gln Met Thr Lys Lys Cys
1               5                   10                  15

Tyr Asp Cys Cys Gly Gly Lys Gly Lys Gly Lys Cys Tyr Gly Pro Gln
            20                  25                  30

Cys Ile Cys Ala Pro Tyr
        35

<210> SEQ ID NO 18
<211> LENGTH: 34
<212> TYPE: PRT
<213> ORGANISM: Artificial sequence
<220> FEATURE:
<223> OTHER INFORMATION: Probable Toxin LQH 8/6 consensus sequence
<220> FEATURE:
<221> NAME/KEY: MISC_FEATURE
<222> LOCATION: (2)..(2)
<223> OTHER INFORMATION: Xaa can be Met or Ser
<220> FEATURE:
<221> NAME/KEY: MISC_FEATURE
<222> LOCATION: (9)..(9)
<223> OTHER INFORMATION: Xaa can be His or Gln
<220> FEATURE:
<221> NAME/KEY: MISC_FEATURE
<222> LOCATION: (12)..(12)
<223> OTHER INFORMATION: Xaa can be Ala or Thr

```
<220> FEATURE:
<221> NAME/KEY: MISC_FEATURE
<222> LOCATION: (16)..(16)
<223> OTHER INFORMATION: Xaa can

```
<210> SEQ ID NO 21
<211> LENGTH: 59
<212> TYPE: PRT
<213> ORGANISM: Mesobuthus martensii

<400> SEQUENCE: 21

Met Lys Phe Leu Tyr Gly Ile Val Phe Ile Ala Leu Phe Leu Thr Val
1               5                   10                  15

Met Phe Ala Thr Gln Thr Asp Gly Cys Gly Pro Cys Phe Thr Thr Asp
            20                  25                  30

Ala Asn Met Ala Arg Lys Cys Arg Glu Cys Cys Gly Gly Ile Gly Lys
        35                  40                  45

Cys Phe Gly Pro Gln Cys Leu Cys Asn Arg Ile
    50                  55

<210> SEQ ID NO 22
<211> LENGTH: 32
<212> TYPE: PRT
<213> ORGANISM: Artificial sequence
<220> FEATURE:
<223> OTHER INFORMATION: Chinese Scorpion consensus sequence
<220> FEATURE:
<221> NAME/KEY: MISC_FEATURE
<222> LOCATION: (2)..(2)
<223> OTHER INFORMATION: Xaa can be Met or Gly
<220> FEATURE:
<221> NAME/KEY: MISC_FEATURE
<222> LOCATION: (9)..(9)
<223> OTHER INFORMATION: Xaa can be His or Ala
<220> FEATURE:
<221> NAME/KEY: MISC_FEATURE
<222> LOCATION: (16)..(16)
<223> OTHER INFORMATION: Xaa can be Asp or Arg
<220> FEATURE:
<221> NAME/KEY: MISC_FEATURE
<222> LOCATION: (22)..(22)
<223> OTHER INFORMATION: Xaa can be Lys or Ile
<220> FEATURE:
<221> NAME/KEY: MISC_FEATURE
<222> LOCATION: (25)..(25)
<223> OTHER INFORMATION: Xaa can be Gly or Cys
<220> FEATURE:
<221> NAME/KEY: MISC_FEATURE
<222> LOCATION: (26)..(26)
<223> OTHER INFORMATION: Xaa can be Lys or Phe
<220> FEATURE:
<221> NAME/KEY: MISC_FEATURE
<222> LOCATION: (27)..(27)
<223> OTHER INFORMATION: Xaa can be Cys or Gly
<220> FEATURE:
<221> NAME/KEY: MISC_FEATURE
<222> LOCATION: (28)..(28)
<223> OTHER INFORMATION: Xaa can be Tyr or Pro
<220> FEATURE:
<221> NAME/KEY: MISC_FEATURE
<222> LOCATION: (29)..(29)
<223> OTHER INFORMATION: Xaa can be Gly or Gln
<220> FEATURE:
<221> NAME/KEY: MISC_FEATURE
<222> LOCATION: (30)..(30)
<223> OTHER INFORMATION: Xaa can be Pro or Cys
<220> FEATURE:
<221> NAME/KEY: MISC_FEATURE
<222> LOCATION: (31)..(31)
<223> OTHER INFORMATION: Xaa can be Gln or Leu

<400> SEQUENCE: 22

Cys Xaa Pro Cys Phe Thr Thr Asp Xaa Asn Met Ala Arg Lys Cys Xaa
1               5                   10                  15

Asp Cys Cys Gly Gly Xaa Gly Lys Xaa Xaa Xaa Xaa Xaa Xaa Xaa Cys
            20                  25                  30
```

```
<210> SEQ ID NO 23
<211> LENGTH: 37
<212> TYPE: PRT
<213> ORGANISM: Mesobuthus eupeus
<220> FEATURE:
<221> NAME/KEY: MISC_FEATURE
<222> LOCATION: (1)..(37)
<223> OTHER INFORMATION: Xaa can be any amino acid

<400> SEQUENCE: 23

Met Cys Met Pro Cys Phe Thr Thr Asp Pro Asn Met Ala Asn Lys Cys
1               5                   10                  15

Arg Asp Cys Cys Gly Gly Xaa Gly Lys Xaa Lys Cys Phe Gly Pro Gln
            20                  25                  30

Cys Leu Cys Asn Arg
        35

<210> SEQ ID NO 24
<211> LENGTH: 35
<212> TYPE: PRT
<213> ORGANISM: Artificial sequence
<220> FEATURE:
<223> OTHER INFORMATION: Insect toxin I5 consensus sequence
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (14)..(14)
<223> OTHER INFORMATION: Xaa can be Arg or Asn
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (23)..(26)
<223> OTHER INFORMATION: Xaa can be any amino acid

<400> SEQUENCE: 24

Met Cys Met Pro Cys Phe Thr Thr Asp Xaa Asn Met Ala Xaa Lys Cys
1               5                   10                  15

Xaa Asp Cys Cys Gly Gly Xaa Gly Lys Xaa Lys Cys Phe Gly Pro Gln
            20                  25                  30

Cys Leu Cys
        35

<210> SEQ ID NO 25
<211> LENGTH: 35
<212> TYPE: PRT
<213> ORGANISM: Mesobuthus eupeus

<400> SEQUENCE: 25

Met Cys Met Pro Cys Phe Thr Thr Asp Pro Asn Met Ala Asn Lys Cys
1               5                   10                  15

Arg Asp Cys Cys Gly Gly Gly Lys Lys Cys Phe Gly Pro Gln Cys Leu
            20                  25                  30

Cys Asn Arg
        35

<210> SEQ ID NO 26
<211> LENGTH: 33
<212> TYPE: PRT
<213> ORGANISM: Artificial sequence
<220> FEATURE:
<223> OTHER INFORMATION: Insect toxin I5 consensus sequence
```

```
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (14)..(14)
<223> OTHER INFORMATION: Xaa can be Arg or Asn
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (23)..(24)
<223> OTHER INFORMATION: Xaa can be Lys or Gly
<220> FEATURE:
<221> NAME/KEY: MISC_FEATURE
<222> LOCATION: (26)..(26)
<223> OTHER INFORMATION: Xaa can be Gly or Cys
<220> FEATURE:
<221> NAME/KEY: MISC_FEATURE
<222> LOCATION: (27)..(27)
<223> OTHER INFORMATION: Xaa can be Lys or Phe
<220> FEATURE:
<221> NAME/KEY: MISC_FEATURE
<222> LOCATION: (28)..(28)
<223> OTHER INFORMATION: Xaa can be Cys or Gly
<220> FEATURE:
<221> NAME/KEY: MISC_FEATURE
<222> LOCATION: (29)..(29)
<223> OTHER INFORMATION: Xaa can be Tyr or Pro
<220> FEATURE:
<221> NAME/KEY: MISC_FEATURE
<222> LOCATION: (30)..(30)
<223> OTHER INFORMATION: Xaa can be Gly or Gln
<220> FEATURE:
<221> NAME/KEY: MISC_FEATURE
<222> LOCATION: (31)..(31)
<223> OTHER INFORMATION: Xaa can be Pro or Cys
<220> FEATURE:
<221> NAME/KEY: MISC_FEATURE
<222> LOCATION: (32)..(32)
<223> OTHER INFORMATION: Xaa can be Gln or Leu

<400> SEQUENCE: 26

Met Cys Met Pro Cys Phe Thr Thr Asp Xaa Asn Met Ala Xaa Lys Cys
1               5                   10                  15

Xaa Asp Cys Cys Gly Gly Xaa Xaa Lys Xaa Xaa Xaa Xaa Xaa Xaa Xaa
                20                  25                  30

Cys

<210> SEQ ID NO 27
<211> LENGTH: 38
<212> TYPE: PRT
<213> ORGANISM: Mesobuthus eupeus
<220> FEATURE:
<221> NAME/KEY: MISC_FEATURE
<222> LOCATION: (1)..(38)
<223> OTHER INFORMATION: Xaa can be any amino acid

<400> SEQUENCE: 27

Met Cys Met Pro Cys Phe Thr Thr Arg Pro Asp Met Ala Gln Gln Cys
1               5                   10                  15

Arg Ala Cys Cys Lys Gly Xaa Xaa Arg Gly Lys Cys Phe Gly Pro Gln
                20                  25                  30

Cys Leu Cys Gly Tyr Asp
            35
```

```
<210> SEQ ID NO 28
<211> LENGTH: 35
<212> TYPE: PRT
<213> ORGANISM: Artificial sequence
<220> FEATURE:
<223> OTHER INFORMATION: Insectotoxin I1 consensus sequence
<220> FEATURE:
<221> NAME/KEY: MISC_FEATURE
<222> LOCATION: (9)..(9)
<223> OTHER INFORMATION: Xaa can be Asp or Arg
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (11)..(11)
<223> OTHER INFORMATION: Xaa can be Gln or Asp
<220> FEATURE:
<221> NAME/KEY: MISC_FEATURE
<222> LOCATION: (14)..(14)
<223> OTHER INFORMATION: Xaa can be Arg or Gln
<220> FEATURE:
<221> NAME/KEY: MISC_FEATURE
<222> LOCATION: (15)..(15)
<223> OTHER INFORMATION: Xaa can be Lys or Gln
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (18)..(18)
<223> OTHER INFORMATION: Xaa can be Asp or Ala
<220> FEATURE:
<221> NAME/KEY: MISC_FEATURE
<222> LOCATION: (21)..(21)
<223> OTHER INFORMATION: Xaa can be Gly or Lys
<220> FEATURE:
<221> NAME/KEY: MISC_FEATURE
<222> LOCATION: (23)..(24)
<223> OTHER INFORMATION: Xaa can be any amino acid

<400> SEQUENCE: 28

Met Cys Met Pro Cys Phe Thr Thr Xaa Xaa Xaa Met Ala Xaa Xaa Cys
1               5                   10                  15

Xaa Xaa Cys Cys Xaa Gly Xaa Xaa Arg Gly Lys Cys Phe Gly Pro Gln
            20                  25                  30

Cys Leu Cys
        35

<210> SEQ ID NO 29
<211> LENGTH: 36
<212> TYPE: PRT
<213> ORGANISM: Mesobuthus eupeus

<400> SEQUENCE: 29

Met Cys Met Pro Cys Phe Thr Thr Arg Pro Asp Met Ala Gln Gln Cys
1               5                   10                  15

Arg Ala Cys Cys Lys Gly Arg Gly Lys Cys Phe Gly Pro Gln Cys Leu
            20                  25                  30

Cys Gly Tyr Asp
        35

<210> SEQ ID NO 30
<211> LENGTH: 33
<212> TYPE: PRT
<213> ORGANISM: Artificial sequence
<220> FEATURE:
<223> OTHER INFORMATION: Insectotoxin I1 consensus sequence
```

```
<220> FEATURE:
<221> NAME/KEY: MISC_FEATURE
<222> LOCATION: (9)..(9)
<223> OTHER INFORMATION: Xaa can be Asp or Arg
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (11)..(11)
<223> OTHER INFORMATION: Xaa can be Gln or Asp
<220> FEATURE:
<221> NAME/KEY: MISC_FEATURE
<222> LOCATION: (14)..(14)
<223> OTHER INFORMATION: Xaa can be Arg or Gln
<220> FEATURE:
<221> NAME/KEY: MISC_FEATURE
<222> LOCATION: (15)..(15)
<223> OTHER INFORMATION: Xaa can be Lys or Gln
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (18)..(18)
<223> OTHER INFORMATION: Xaa can be Asp or Arg
<220> FEATURE:
<221> NAME/KEY: MISC_FEATURE
<222> LOCATION: (21)..(21)
<223> OTHER INFORMATION: Xaa can be Gly or Lys
<220> FEATURE:
<221> NAME/KEY: MISC_FEATURE
<222> LOCATION: (26)..(26)
<223> OTHER INFORMATION: Xaa can be Gly or Cys
<220> FEATURE:
<221> NAME/KEY: MISC_FEATURE
<222> LOCATION: (27)..(27)
<223> OTHER INFORMATION: Xaa can be Lys or Phe
<220> FEATURE:
<221> NAME/KEY: MISC_FEATURE
<222> LOCATION: (28)..(28)
<223> OTHER INFORMATION: Xaa can be Cys or Gly
<220> FEATURE:
<221> NAME/KEY: MISC_FEATURE
<222> LOCATION: (29)..(29)
<223> OTHER INFORMATION: Xaa can be Tyr or Pro
<220> FEATURE:
<221> NAME/KEY: MISC_FEATURE
<222> LOCATION: (30)..(30)
<223> OTHER INFORMATION: Xaa can be Gly or Gln
<220> FEATURE:
<221> NAME/KEY: MISC_FEATURE
<222> LOCATION: (31)..(31)
<223> OTHER INFORMATION: Xaa can be Pro or Cys
<220> FEATURE:
<221> NAME/KEY: MISC_FEATURE
<222> LOCATION: (32)..(32)
<223> OTHER INFORMATION: Xaa can be Gln or Leu

<400> SEQUENCE: 30

Met Cys Met Pro Cys Phe Thr Thr Xaa Xaa Xaa Met Ala Xaa Xaa Cys
1               5                   10                  15

Xaa Xaa Cys Cys Xaa Gly Lys Gly Lys Xaa Xaa Xaa Xaa Xaa Xaa
            20                  25                  30

Cys

<210> SEQ ID NO 31
<211> LENGTH: 37
<212> TYPE: PRT
<213> ORGANISM: Mesobuthus eupeus
<220> FEATURE:
<221> NAME/KEY: MISC_FEATURE
<222> LOCATION: (1)..(37)
<223> OTHER INFORMATION: Xaa can be any amino acid
```

```
<400> SEQUENCE: 31

Met Cys Met Pro Cys Phe Thr Thr Asp Pro Asn Met Ala Lys Lys Cys
1               5                   10                  15

Arg Asp Cys Cys Gly Gly Asn Gly Xaa Xaa Lys Cys Phe Gly Pro Gln
            20                  25                  30

Cys Leu Cys Asn Arg
        35

<210> SEQ ID NO 32
<211> LENGTH: 35
<212> TYPE: PRT
<213> ORGANISM: Artificial sequence
<220> FEATURE:
<223> OTHER INFORMATION: Insectotoxin 15A consensus sequence
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (17)..(17)
<223> OTHER INFORMATION: Xaa can be Asp or Arg
<220> FEATURE:
<221> NAME/KEY: MISC_FEATURE
<222> LOCATION: (23)..(23)
<223> OTHER INFORMATION: Xaa can be Lys or Asn
<220> FEATURE:
<221> NAME/KEY: MISC_FEATURE
<222> LOCATION: (25)..(26)
<223> OTHER INFORMATION: Xaa can be any amino acid

<400> SEQUENCE: 32

Met Cys Met Pro Cys Phe Thr Thr Asp Xaa Asn Met Ala Lys Lys Cys
1               5                   10                  15

Xaa Asp Cys Cys Gly Gly Xaa Gly Xaa Xaa Lys Cys Phe Gly Pro Gln
            20                  25                  30

Cys Leu Cys
        35

<210> SEQ ID NO 33
<211> LENGTH: 35
<212> TYPE: PRT
<213> ORGANISM: Mesobuthus eupeus

<400> SEQUENCE: 33

Met Cys Met Pro Cys Phe Thr Thr Asp Pro Asn Met Ala Lys Lys Cys
1               5                   10                  15

Arg Asp Cys Cys Gly Gly Asn Gly Lys Cys Phe Gly Pro Gln Cys Leu
            20                  25                  30

Cys Asn Arg
        35

<210> SEQ ID NO 34
<211> LENGTH: 33
<212> TYPE: PRT
<213> ORGANISM: Artificial sequence
<220> FEATURE:
<223> OTHER INFORMATION: Insectotoxin 15A consensus sequence
<220> FEATURE:
<221> NAME/KEY: MISC_FEATURE
<222> LOCATION: (10)..(10)
<223> OTHER INFORMATION: Xaa can be His or Pro
<220> FEATURE:
<221> NAME/KEY: MISC_FEATURE
<222> LOCATION: (17)..(17)
<223> OTHER INFORMATION: Xaa can be Asp or Arg

```
<220> FEATURE:
<221> NAME/KEY: MISC_FEATURE
<222> LOCATION: (23)..(23)
<223> OTHER INFORMATION: Xaa can be Lys or Asn
<220> FEATURE:
<221> NAME/KEY: MISC_FEATURE
<222> LOCATION: (26)..(26)
<223> OTHER INFORMATION: Xaa can be Gly or Cys
<220> FEATURE:
<221> NAME/KEY: MISC_FEATURE
<222> LOCATION: (27)..(27)
<223> OTHER INFORMATION: Xaa can be Lys or Phe
<220> FEATURE:
<221> NAME/KEY: MISC_FEATURE
<222> LOCATION: (28)..(28)
<223> OTHER INFORMATION: Xaa can be Cys or Gly
<220> FEATURE:
<221> NAME/KEY: MISC_FEATURE
<222> LOCATION: (29)..(29)
<223> OTHER INFORMATION: Xaa can be Tyr or Pro
<220> FEATURE:
<221> NAME/KEY: MISC_FEATURE
<222> LOCATION: (30)..(30)
<223> OTHER INFORMATION: Xaa can be Gly or Gln
<220> FEATURE:
<221> NAME/KEY: MISC_FEATURE
<222> LOCATION: (31)..(31)
<223> OTHER INFORMATION: Xaa can be Pro or Cys
<220> FEATURE:
<221> NAME/KEY: MISC_FEATURE
<222> LOCATION: (32)..(32)
<223> OTHER INFORMATION: Xaa can be Gln or Leu

<400> SEQUENCE: 34

Met Cys Met Pro Cys Phe Thr Thr Asp Xaa Asn Met Ala Lys Lys Cys
1               5                   10                  15

Xaa Asp Cys Cys Gly Gly Xaa Gly Lys Xaa Xaa Xaa Xaa Xaa Xaa Xaa
            20                  25                  30

Cys

<210> SEQ ID NO 35
<211> LENGTH: 37
<212> TYPE: PRT
<213> ORGANISM: Androctonus mauretanicus
<220> FEATURE:
<221> NAME/KEY: MISC_FEATURE
<222> LOCATION: (1)..(37)
<223> OTHER INFORMATION: Xaa can be any amino acid

<400> SEQUENCE: 35

Cys Gly Pro Cys Phe Thr Thr Asp Pro Tyr Thr Glu Ser Lys Cys Ala
1               5                   10                  15

Thr Cys Cys Gly Gly Xaa Xaa Arg Gly Lys Cys Val Gly Pro Gln Cys
            20                  25                  30

Leu Cys Asn Arg Ile
        35

<210> SEQ ID NO 36
<211> LENGTH: 34
<212> TYPE: PRT
<213> ORGANISM: Artificial sequence
<220> FEATURE:
<223> OTHER INFORMATION: Neurotoxin P2 consensus sequence
<220> FEATURE:
<221> NAME/KEY: MISC_FEATURE
<222> LOCATION: (2)..(2)
<223> OTHER INFORMATION: Xaa can be Met or Gly
<220> FEATURE:
<221> NAME/KEY: MISC_FEATURE
<222> LOCATION: (9)..(9)
<223> OTHER INFORMATION: Xaa can be His or Pro
```

```
<220> FEATURE:
<221> NAME/KEY: MISC_FEATURE
<222> LOCATION: (10)..(10)
<223> OTHER INFORMATION: Xaa can be Gln or Tyr
<220> FEATURE:
<221> NAME/KEY: MISC_FEATURE
<222> LOCATION: (11)..(11)
<223> OTHER INFORMATION: Xaa can be Met or Thr
<220> FEATURE:
<221> NAME/KEY: MISC_FEATURE
<222> LOCATION: (12)..(12)
<223> OTHER INFORMATION: Xaa can be Ala or Glu
<220> FEATURE:
<221> NAME/KEY: MISC_FEATURE
<222> LOCATION: (13)..(13)
<223> OTHER INFORMATION: Xaa can be Arg or Ser
<220> FEATURE:
<221> NAME/KEY: MISC_FEATURE
<222> LOCATION: (16)..(16)
<223> OTHER INFORMATION: Xaa can be Asp or Ala
<220> FEATURE:
<221> NAME/KEY: MISC_FEATURE
<222> LOCATION: (17)..(17)
<223> OTHER INFORMATION: Xaa can be Asp or Thr
<220> FEATURE:
<221> NAME/KEY: MISC_FEATURE
<222> LOCATION: (22)..(23)
<223> OTHER INFORMATION: Xaa can be any amino acid
<220> FEATURE:
<221> NAME/KEY: MISC_FEATURE
<222> LOCATION: (28)..(28)
<223> OTHER INFORMATION: Xaa can be Tyr or Val

<400> SEQUENCE: 36

Cys Xaa Pro Cys Phe Thr Thr Asp Xaa Xaa Xaa Xaa Xaa Lys Cys Xaa
1               5                   10                  15

Xaa Cys Cys Gly Gly Xaa Xaa Arg Gly Lys Cys Xaa Gly Pro Gln Cys
            20                  25                  30

Leu Cys

<210> SEQ ID NO 37
<211> LENGTH: 35
<212> TYPE: PRT
<213> ORGANISM: Androctonus mauretanicus

<400> SEQUENCE: 37

Cys Gly Pro Cys Phe Thr Thr Asp Pro Tyr Thr Glu Ser Lys Cys Ala
1               5                   10                  15

Thr Cys Cys Gly Gly Arg Gly Lys Cys Val Gly Pro Gln Cys Leu Cys
            20                  25                  30

Asn Arg Ile
        35

<210> SEQ ID NO 38
<211> LENGTH: 32
<212> TYPE: PRT
<213> ORGANISM: Artificial sequence
<220> FEATURE:
<223> OTHER INFORMATION: Neurotoxin P2 consensus sequence
<220> FEATURE:
<221> NAME/KEY: MISC_FEATURE
<222> LOCATION: (2)..(2)
<223> OTHER INFORMATION: Xaa can be Met or Gly
<220> FEATURE:
<221> NAME/KEY: MISC_FEATURE
<222> LOCATION: (9)..(9)
<223> OTHER INFORMATION: Xaa can be His or Pro
<220> FEATURE:
<221> NAME/KEY: MISC_FEATURE
<222> LOCATION: (10)..(10)
<223> OTHER INFORMATION: Xaa can be Gln or Tyr
```

```
<220> FEATURE:
<221> NAME/KEY: MISC_FEATURE
<222> LOCATION: (11)..(11)
<223> OTHER INFORMATION: Xaa ca be Met or Thr
<220> FEATURE:
<221> NAME/KEY: MISC_FEATURE
<222> LOCATION: (12)..(12)
<223> OTHER INFORMATION: Xaa can be Ala or Glu
<220> FEATURE:
<221> NAME/KEY: MISC_FEATURE
<222> LOCATION: (13)..(13)
<223> OTHER INFORMATION: Xaa can be Arg or Ser
<220> FEATURE:
<221> NAME/KEY: MISC_FEATURE
<222> LOCATION: (16)..(16)
<223> OTHER INFORMATION: Xaa can be Asp or Ala
<220> FEATURE:
<221> NAME/KEY: MISC_FEATURE
<222> LOCATION: (17)..(17)
<223> OTHER INFORMATION: Xaa can be Asp or Thr
<220> FEATURE:
<221> NAME/KEY: MISC_FEATURE
<222> LOCATION: (25)..(25)
<223> OTHER INFORMATION: Xaa can be Gly or Cys
<220> FEATURE:
<221> NAME/KEY: MISC_FEATURE
<222> LOCATION: (26)..(26)
<223> OTHER INFORMATION: Xaa can be Lys or Val
<220> FEATURE:
<221> NAME/KEY: MISC_FEATURE
<222> LOCATION: (27)..(27)
<223> OTHER INFORMATION: Xaa can be Cys or Gly
<220> FEATURE:
<221> NAME/KEY: MISC_FEATURE
<222> LOCATION: (28)..(28)
<223> OTHER INFORMATION: Xaa can be Tyr or Pro
<220> FEATURE:
<221> NAME/KEY: MISC_FEATURE
<222> LOCATION: (29)..(29)
<223> OTHER INFORMATION: Xaa can be Gly or Gln
<220> FEATURE:
<221> NAME/KEY: MISC_FEATURE
<222> LOCATION: (30)..(30)
<223> OTHER INFORMATION: Xaa can be Pro or Cys
<220> FEATURE:
<221> NAME/KEY: MISC_FEATURE
<222> LOCATION: (31)..(31)
<223> OTHER INFORMATION: Xaa can be Gln or Leu

<400> SEQUENCE: 38

Cys Xaa Pro Cys Phe Thr Thr Asp Xaa Xaa Xaa Xaa Lys Cys Xaa
1               5                   10                  15

Xaa Cys Cys Gly Gly Lys Gly Lys Xaa Xaa Xaa Xaa Xaa Xaa Cys
            20                  25                  30

<210> SEQ ID NO 39
<211> LENGTH: 37
<212> TYPE: PRT
<213> ORGANISM: Artificial sequence
<220> FEATURE:
<223> OTHER INFORMATION: Toxin consensus sequence
<220> FEATURE:
<221> NAME/KEY: MISC_FEATURE
<222> LOCATION: (1)..(37)
<223> OTHER INFORMATION: Xaa can be any amino acid

<400> SEQUENCE: 39

Met Cys Met Pro Cys Phe Thr Thr Asp Pro Asn Met Ala Lys Lys Cys
1               5                   10                  15

Arg Asp Cys Cys Gly Gly Lys Gly Xaa Xaa Lys Cys Phe Gly Pro Gln
            20                  25                  30

Cys Leu Cys Asn Arg
        35
```

```
<210> SEQ ID NO 40
<211> LENGTH: 35
<212> TYPE: PRT
<213> ORGANISM: Artificial sequence
<220> FEATURE:
<223> OTHER INFORMATION: Toxin consensus sequence
<220> FEATURE:
<221> NAME/KEY: MISC_FEATURE
<222> LOCATION: (3)..(3)
<223> OTHER INFORMATION: Xaa can be Met, Lys or Ser
<220> FEATURE:
<221> NAME/KEY: MISC_FEATURE
<222> LOCATION: (10)..(10)
<223> OTHER INFORMATION: Xaa can be His, Pro, or Gln
<220> FEATURE:
<221> NAME/KEY: MISC_FEATURE
<222> LOCATION: (17)..(17)
<223> OTHER INFORMATION: Xaa can be Asp, Ala, or Tyr

<400> SEQUENCE: 40

Arg Cys Xaa Pro Cys Phe Thr Thr Asp Xaa Gln Met Ser Lys Lys Cys
1               5                   10                  15

Xaa Asp Cys Cys Gly Gly Lys Gly Lys Gly Lys Cys Tyr Gly Pro Gln
            20                  25                  30

Cys Leu Cys
        35

<210> SEQ ID NO 41
<211> LENGTH: 35
<212> TYPE: PRT
<213> ORGANISM: Artificial sequence
<220> FEATURE:
<223> OTHER INFORMATION: Toxin consensus sequence

<400> SEQUENCE: 41

Met Cys Met Pro Cys Phe Thr Thr Asp Pro Asn Met Ala Arg Lys Cys
1               5                   10                  15

Arg Asp Cys Cys Gly Gly Arg Gly Lys Cys Phe Gly Pro Gln Cys Leu
            20                  25                  30

Cys Asn Arg
        35

<210> SEQ ID NO 42
<211> LENGTH: 10
<212> TYPE: PRT
<213> ORGANISM: Artificial sequence
<220> FEATURE:
<223> OTHER INFORMATION: Pep8-Ctlx

<400> SEQUENCE: 42

Cys Gly Gly Lys Gly Arg Gly Lys Cys Tyr
1               5                   10

<210> SEQ ID NO 43
<211> LENGTH: 10
<212> TYPE: PRT
<213> ORGANISM: Artificial sequence
<220> FEATURE:
<223> OTHER INFORMATION: Pep8-SCX1_BUTSI

<400> SEQUENCE: 43

Cys Gly Gly Lys Gly Lys Gly Lys Cys Tyr
1               5                   10

<210> SEQ ID NO 44
<211> LENGTH: 10
<212> TYPE: PRT
<213> ORGANISM: Artificial sequence
```

```
<220> FEATURE:
<223> OTHER INFORMATION: Pep8-AF079059_2

<400> SEQUENCE: 44

Cys Gly Gly Ile Gly Lys Cys Phe Gly Pro
1               5                   10

<210> SEQ ID NO 45
<211> LENGTH: 12
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (4)..(4)
<223> OTHER INFORMATION: Xaa can be Lys or Ile

<400> SEQUENCE: 45

Cys Gly Gly Xaa Gly Arg Gly Lys Cys Phe Gly Pro
1               5                   10

<210> SEQ ID NO 46
<211> LENGTH: 6
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (4)..(4)
<223> OTHER INFORMATION: Xaa can be Lys or Ile

<400> SEQUENCE: 46

Cys Gly Gly Xaa Gly Lys
1               5

<210> SEQ ID NO 47
<211> LENGTH: 10
<212> TYPE: PRT
<213> ORGANISM: Artificial sequence
<220> FEATURE:
<223> OTHER INFORMATION: Pep8-NJ0361 sequence

<400> SEQUENCE: 47

Cys Gly Gly Gly Lys Lys Cys Phe Gly Pro
1               5                   10

<210> SEQ ID NO 48
<211> LENGTH: 12
<212> TYPE: PRT
<213> ORGANISM: Artificial sequence
<220> FEATURE:
<223> OTHER INFORMATION: Chlorotoxin Peptide 8 consensus sequence

<400> SEQUENCE: 48

Cys Gly Gly Lys Gly Lys Gly Lys Cys Phe Gly Pro
1               5                   10

<210> SEQ ID NO 49
<211> LENGTH: 6
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (4)..(5)
<223> OTHER INFORMATION: Xaa can be Lys or Gly
```

```
<400> SEQUENCE: 49

Cys Gly Gly Xaa Xaa Lys
1               5

<210> SEQ ID NO 50
<211> LENGTH: 10
<212> TYPE: PRT
<213> ORGANISM: Artificial sequence
<220> FEATURE:
<223> OTHER INFORMATION: Pep8-SCX1_BUTEU sequence

<400> SEQUENCE: 50

Cys Lys Gly Arg Gly Lys Cys Phe Gly Pro
1               5                  10

<210> SEQ ID NO 51
<211> LENGTH: 12
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (3)..(3)
<223> OTHER INFORMATION: Xaa can be Gly or Cys

<400> SEQUENCE: 51

Cys Gly Xaa Lys Gly Arg Gly Lys Cys Phe Gly Pro
1               5                  10

<210> SEQ ID NO 52
<211> LENGTH: 6
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (2)..(2)
<223> OTHER INFORMATION: Xaa can be Gly or Lys

<400> SEQUENCE: 52

Cys Xaa Gly Lys Gly Lys
1               5

<210> SEQ ID NO 53
<211> LENGTH: 10
<212> TYPE: PRT
<213> ORGANISM: Artificial sequence
<220> FEATURE:
<223> OTHER INFORMATION: Pep8-SCX5_BUTEU sequence

<400> SEQUENCE: 53

Cys Gly Gly Asn Gly Lys Cys Phe Gly Pro
1               5                  10

<210> SEQ ID NO 54
<211> LENGTH: 12
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (4)..(4)
<223> OTHER INFORMATION: Xaa can be Lys or Asn
```

```
<400> SEQUENCE: 54

Cys Gly Gly Xaa Gly Arg Gly Lys Cys Phe Gly Pro
1               5                   10

<210> SEQ ID NO 55
<211> LENGTH: 6
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (4)..(4)
<223> OTHER INFORMATION: Xaa can be Lys or Asn

<400> SEQUENCE: 55

Cys Gly Gly Xaa Gly Lys
1               5

<210> SEQ ID NO 56
<211> LENGTH: 10
<212> TYPE: PRT
<213> ORGANISM: Artificial sequence
<220> FEATURE:
<223> OTHER INFORMATION: Pep8-SCXP_ANDMA sequence

<400> SEQUENCE: 56

Cys Gly Gly Arg Gly Lys Cys Val Gly Pro
1               5                   10

<210> SEQ ID NO 57
<211> LENGTH: 12
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (10)..(10)
<223> OTHER INFORMATION: Xaa can be Tyr or Val

<400> SEQUENCE: 57

Cys Gly Gly Lys Gly Arg Gly Lys Cys Xaa Gly Pro
1               5                   10

<210> SEQ ID NO 58
<211> LENGTH: 6
<212> TYPE: PRT
<213> ORGANISM: Artificial sequence
<220> FEATURE:
<223> OTHER INFORMATION: Chlorotoxin Peptide 8 consensus sequence

<400> SEQUENCE: 58

Cys Gly Gly Lys Gly Lys
1               5

<210> SEQ ID NO 59
<211> LENGTH: 12
<212> TYPE: PRT
<213> ORGANISM: Artificial sequence
<220> FEATURE:
<223> OTHER INFORMATION: Chlorotoxin Peptide 8 consensus sequence
<220> FEATURE:
<221> NAME/KEY: MISC_FEATURE
<222> LOCATION: (4)..(5)
<223> OTHER INFORMATION: Xaa can be Lys or Gly
```

```
<400> SEQUENCE: 59

Cys Gly Gly Xaa Xaa Arg Gly Lys Cys Phe Gly Pro
1               5                   10

<210> SEQ ID NO 60
<211> LENGTH: 10
<212> TYPE: PRT
<213> ORGANISM: Artificial sequence
<220> FEATURE:
<223> OTHER INFORMATION: Chlorotoxin Peptide 8 consensus sequence

<400> SEQUENCE: 60

Cys Gly Gly Lys Gly Lys Cys Phe Gly Pro
1               5                   10

<210> SEQ ID NO 61
<211> LENGTH: 10
<212> TYPE: PRT
<213> ORGANISM: Artificial sequence
<220> FEATURE:
<223> OTHER INFORMATION: Chlorotoxin Peptide 21 sequence

<400> SEQUENCE: 61

Thr Thr Asp His Gln Met Ala Arg Lys Cys
1               5                   10

<210> SEQ ID NO 62
<211> LENGTH: 10
<212> TYPE: PRT
<213> ORGANISM: Artificial sequence
<220> FEATURE:
<223> OTHER INFORMATION: Pep21-SCX1-BUTSI sequence

<400> SEQUENCE: 62

Thr Thr Asp Pro Gln Met Ser Lys Lys Cys
1               5                   10

<210> SEQ ID NO 63
<211> LENGTH: 10
<212> TYPE: PRT
<213> ORGANISM: Artificial sequence
<220> FEATURE:
<223> OTHER INFORMATION: Chlorotoxin Peptide 21 consensus sequence
<220> FEATURE:
<221> NAME/KEY: MISC_FEATURE
<222> LOCATION: (4)..(4)
<223> OTHER INFORMATION: Xaa can be His or Pro

<400> SEQUENCE: 63

Thr Thr Asp Xaa Gln Met Ala Lys Lys Cys
1               5                   10

<210> SEQ ID NO 64
<211> LENGTH: 10
<212> TYPE: PRT
<213> ORGANISM: Artificial sequence
<220> FEATURE:
<223> OTHER INFORMATION: Pep21-SCX8_LEIQH sequence

<400> SEQUENCE: 64

Thr Thr Asp Gln Gln Met Thr Lys Lys Cys
1               5                   10

<210> SEQ ID NO 65
<211> LENGTH: 10
<212> TYPE: PRT
<213> ORGANISM: Artificial sequence
```

```
<220> FEATURE:
<223> OTHER INFORMATION: Chlorotoxin Peptide 21 consensus sequence
<220> FEATURE:
<221> NAME/KEY: MISC_FEATURE
<222> LOCATION: (4)..(4)
<223> OTHER INFORMATION: Xaa can be His or Gln
<220> FEATURE:
<221> NAME/KEY: MISC_FEATURE
<222> LOCATION: (7)..(7)
<223> OTHER INFORMATION: Xaa can be Ala or Thr

<400> SEQUENCE: 65

Thr Thr Asp Xaa Gln Met Xaa Lys Lys Cys
1               5                   10

<210> SEQ ID NO 66
<211> LENGTH: 10
<212> TYPE: PRT
<213> ORGANISM: Artificial sequence
<220> FEATURE:
<223> OTHER INFORMATION: Pep21-AF079059_2 sequence

<400> SEQUENCE: 66

Thr Thr Asp Ala Asn Met Ala Arg Lys Cys
1               5                   10

<210> SEQ ID NO 67
<211> LENGTH: 10
<212> TYPE: PRT
<213> ORGANISM: Artificial sequence
<220> FEATURE:
<223> OTHER INFORMATION: Chlorotoxin Peptide 21 consensus sequence
<220> FEATURE:
<221> NAME/KEY: MISC_FEATURE
<222> LOCATION: (4)..(4)
<223> OTHER INFORMATION: Xaa can be His or Ala

<400> SEQUENCE: 67

Thr Thr Asp Xaa Asn Met Ala Arg Lys Cys
1               5                   10

<210> SEQ ID NO 68
<211> LENGTH: 10
<212> TYPE: PRT
<213> ORGANISM: Artificial sequence
<220> FEATURE:
<223> OTHER INFORMATION: Pep21-JN0361 sequence

<400> SEQUENCE: 68

Thr Thr Asp Pro Asn Met Ala Asn Lys Cys
1               5                   10

<210> SEQ ID NO 69
<211> LENGTH: 10
<212> TYPE: PRT
<213> ORGANISM: Artificial sequence
<220> FEATURE:
<223> OTHER INFORMATION: Chlorotoxin Peptide 21 consensus sequence
<220> FEATURE:
<221> NAME/KEY: MISC_FEATURE
<222> LOCATION: (4)..(4)
<223> OTHER INFORMATION: Xaa can be either His or Pro
<220> FEATURE:
<221> NAME/KEY: MISC_FEATURE
<222> LOCATION: (8)..(8)
<223> OTHER INFORMATION: Xaa can be Arg or Asn

<400> SEQUENCE: 69

Thr Thr Asp Xaa Asn Met Ala Xaa Lys Cys
1               5                   10
```

```
<210> SEQ ID NO 70
<211> LENGTH: 10
<212> TYPE: PRT
<213> ORGANISM: Artificial sequence
<220> FEATURE:
<223> OTHER INFORMATION: Pep21-SCX1_BUTEU sequence

<400> SEQUENCE: 70

Thr Thr Arg Pro Asp Met Ala Gln Gln Cys
1               5                   10

<210> SEQ ID NO 71
<211> LENGTH: 10
<212> TYPE: PRT
<213> ORGANISM: Artificial sequence
<220> FEATURE:
<223> OTHER INFORMATION: Chlorotoxin Peptide 21 consensus sequence
<220> FEATURE:
<221> NAME/KEY: MISC_FEATURE
<222> LOCATION: (3)..(3)
<223> OTHER INFORMATION: Xaa can be Asp or Arg
<220> FEATURE:
<221> NAME/KEY: MISC_FEATURE
<222> LOCATION: (4)..(4)
<223> OTHER INFORMATION: Xaa can be His or Pro
<220> FEATURE:
<221> NAME/KEY: MISC_FEATURE
<222> LOCATION: (5)..(5)
<223> OTHER INFORMATION: Xaa can be Gln or Asp
<220> FEATURE:
<221> NAME/KEY: MISC_FEATURE
<222> LOCATION: (8)..(8)
<223> OTHER INFORMATION: Xaa can be Arg or Gln
<220> FEATURE:
<221> NAME/KEY: MISC_FEATURE
<222> LOCATION: (9)..(9)
<223> OTHER INFORMATION: Xaa can be Lys or Gln

<400> SEQUENCE: 71

Thr Thr Xaa Xaa Xaa Met Ala Xaa Xaa Cys
1               5                   10

<210> SEQ ID NO 72
<211> LENGTH: 10
<212> TYPE: PRT
<213> ORGANISM: Artificial sequence
<220> FEATURE:
<223> OTHER INFORMATION: Pep21-SCX5_BUTEU sequence

<400> SEQUENCE: 72

Thr Thr Asp Pro Asn Met Ala Lys Lys Cys
1               5                   10

<210> SEQ ID NO 73
<211> LENGTH: 10
<212> TYPE: PRT
<213> ORGANISM: Artificial sequence
<220> FEATURE:
<223> OTHER INFORMATION: Chlorotoxin Peptide 21 consensus sequence
<220> FEATURE:
<221> NAME/KEY: MISC_FEATURE
<222> LOCATION: (4)..(4)
<223> OTHER INFORMATION: Xaa can be His or Pro

<400> SEQUENCE: 73

Thr Thr Asp Xaa Asn Met Ala Lys Lys Cys
1               5                   10

<210> SEQ ID NO 74
<211> LENGTH: 10
<212> TYPE: PRT
<213> ORGANISM: Artificial sequence
```

```
<220> FEATURE:
<223> OTHER INFORMATION: Pep21-SCXP_ANDMA sequence

<400> SEQUENCE: 74

Thr Thr Asp Pro Tyr Thr Glu Ser Lys Cys
1               5                   10

<210> SEQ ID NO 75
<211> LENGTH: 10
<212> TYPE: PRT
<213> ORGANISM: Artificial sequence
<220> FEATURE:
<223> OTHER INFORMATION: Chlorotoxin Peptide 21 consensus sequence
<220> FEATURE:
<221> NAME/KEY: MISC_FEATURE
<222> LOCATION: (4)..(4)
<223> OTHER INFORMATION: Xaa can be His or Pro
<220> FEATURE:
<221> NAME/KEY: MISC_FEATURE
<222> LOCATION: (5)..(5)
<223> OTHER INFORMATION: Xaa can be Gln or Tyr
<220> FEATURE:
<221> NAME/KEY: MISC_FEATURE
<222> LOCATION: (6)..(6)
<223> OTHER INFORMATION: Xaa can be Met or Thr
<220> FEATURE:
<221> NAME/KEY: MISC_FEATURE
<222> LOCATION: (7)..(7)
<223> OTHER INFORMATION: Xaa can be Ala or Glu
<220> FEATURE:
<221> NAME/KEY: MISC_FEATURE
<222> LOCATION: (8)..(8)
<223> OTHER INFORMATION: Xaa can be Arg or Ser

<400> SEQUENCE: 75

Thr Thr Asp Xaa Xaa Xaa Xaa Xaa Lys Cys
1               5                   10

<210> SEQ ID NO 76
<211> LENGTH: 10
<212> TYPE: PRT
<213> ORGANISM: Artificial sequence
<220> FEATURE:
<223> OTHER INFORMATION: Chlorotoxin Peptide 21 consensus sequence

<400> SEQUENCE: 76

Thr Thr Asp Pro Asn Met Ala Lys Lys Cys
1               5                   10

<210> SEQ ID NO 77
<211> LENGTH: 7
<212> TYPE: PRT
<213> ORGANISM: Artificial sequence
<220> FEATURE:
<223> OTHER INFORMATION: Chlorotoxin derivative STP-1

<400> SEQUENCE: 77

Thr Asp Pro Gln Met Ser Arg
1               5

<210> SEQ ID NO 78
<211> LENGTH: 10
<212> TYPE: PRT
<213> ORGANISM: Artificial sequence
<220> FEATURE:
<223> OTHER INFORMATION: Peptide 8 sequences

<400> SEQUENCE: 78

Gly Gly Lys Gly Arg Gly Lys Ser Tyr Gly
1               5                   10
```

```
<210> SEQ ID NO 79
<211> LENGTH: 9
<212> TYPE: PRT
<213> ORGANISM: Artificial sequence
<220> FEATURE:
<223> OTHER INFORMATION: Peptide 8a sequence

<400> SEQUENCE: 79

Gly Lys Gly Arg Gly Lys Ser Tyr Gly
1               5

<210> SEQ ID NO 80
<211> LENGTH: 8
<212> TYPE: PRT
<213> ORGANISM: Artificial sequence
<220> FEATURE:
<223> OTHER INFORMATION: Peptide 8b sequence

<400> SEQUENCE: 80

Lys Gly Arg Gly Lys Ser Tyr Gly
1               5

<210> SEQ ID NO 81
<211> LENGTH: 7
<212> TYPE: PRT
<213> ORGANISM: Artificial sequence
<220> FEATURE:
<223> OTHER INFORMATION: Peptide 8c sequence

<400> SEQUENCE: 81

Gly Arg Gly Lys Ser Tyr Gly
1               5

<210> SEQ ID NO 82
<211> LENGTH: 10
<212> TYPE: PRT
<213> ORGANISM: Artificial sequence
<220> FEATURE:
<223> OTHER INFORMATION: Peptide 21 sequence

<400> SEQUENCE: 82

Thr Thr Asp His Gln Met Ala Arg Lys Ser
1               5                   10

<210> SEQ ID NO 83
<211> LENGTH: 8
<212> TYPE: PRT
<213> ORGANISM: Artificial sequence
<220> FEATURE:
<223> OTHER INFORMATION: Peptide 21b sequence

<400> SEQUENCE: 83

Asp His Gln Met Ala Arg Lys Ser
1               5

<210> SEQ ID NO 84
<211> LENGTH: 7
<212> TYPE: PRT
<213> ORGANISM: Artificial sequence
<220> FEATURE:
<223> OTHER INFORMATION: Peptide 21c sequence

<400> SEQUENCE: 84

His Gln Met Ala Arg Lys Ser
1               5
```

```
<210> SEQ ID NO 85
<211> LENGTH: 6
<212> TYPE: PRT
<213> ORGANISM: Artificial sequence
<220> FEATURE:
<223> OTHER INFORMATION: Peptide 21d sequence

<400> SEQUENCE: 85

Gln Met Ala Arg Lys Ser
1               5

<210> SEQ ID NO 86
<211> LENGTH: 9
<212> TYPE: PRT
<213> ORGANISM: Artificial sequence
<220> FEATURE:
<223> OTHER INFORMATION: Peptide 21a-A1 sequence

<400> SEQUENCE: 86

Ala Asp His Gln Met Ala Arg Lys Ser
1               5

<210> SEQ ID NO 87
<211> LENGTH: 9
<212> TYPE: PRT
<213> ORGANISM: Artificial sequence
<220> FEATURE:
<223> OTHER INFORMATION: Peptide 21a-A2 sequence

<400> SEQUENCE: 87

Thr Ala His Gln Met Ala Arg Lys Ser
1               5

<210> SEQ ID NO 88
<211> LENGTH: 9
<212> TYPE: PRT
<213> ORGANISM: Artificial sequence
<220> FEATURE:
<223> OTHER INFORMATION: Peptide 21a-A3 sequence

<400> SEQUENCE: 88

Thr Asp Ala Gln Met Ala Arg Lys Ser
1               5

<210> SEQ ID NO 89
<211> LENGTH: 9
<212> TYPE: PRT
<213> ORGANISM: Artificial sequence
<220> FEATURE:
<223> OTHER INFORMATION: Peptide 21a-A4 sequence

<400> SEQUENCE: 89

Thr Asp His Ala Met Ala Arg Lys Ser
1               5

<210> SEQ ID NO 90
<211> LENGTH: 9
<212> TYPE: PRT
<213> ORGANISM: Artificial sequence
<220> FEATURE:
<223> OTHER INFORMATION: Peptide 21a-A5 sequence

<400> SEQUENCE: 90

Thr Asp His Gln Ala Ala Arg Lys Ser
1               5
```

```
<210> SEQ ID NO 91
<211> LENGTH: 9
<212> TYPE: PRT
<213> ORGANISM: Artificial sequence
<220> FEATURE:
<223> OTHER INFORMATION: Peptide 21a-A7 sequence

<400> SEQUENCE: 91

Thr Asp His Gln Met Ala Ala Lys Ser
1               5

<210> SEQ ID NO 92
<211> LENGTH: 9
<212> TYPE: PRT
<213> ORGANISM: Artificial sequence
<220> FEATURE:
<223> OTHER INFORMATION: Peptide 21a-A8 sequence

<400> SEQUENCE: 92

Thr Asp His Gln Met Ala Arg Ala Ser
1               5

<210> SEQ ID NO 93
<211> LENGTH: 9
<212> TYPE: PRT
<213> ORGANISM: Artificial sequence
<220> FEATURE:
<223> OTHER INFORMATION: Peptide 21a-A9 sequence

<400> SEQUENCE: 93

Thr Asp His Gln Met Ala Arg Lys Ala
1               5

<210> SEQ ID NO 94
<211> LENGTH: 9
<212> TYPE: PRT
<213> ORGANISM: Mesobuthus tamulus sindicus
<220> FEATURE:
<221> NAME/KEY: MISC_FEATURE
<222> LOCATION: (1)..(9)
<223> OTHER INFORMATION: GenBank Accesssion No. P15229, small toxin

<400> SEQUENCE: 94

Thr Thr Asp Gln Gln Met Ser Lys Lys
1               5

<210> SEQ ID NO 95
<211> LENGTH: 9
<212> TYPE: PRT
<213> ORGANISM: Leiurus quinquestriatus hebraeu
<220> FEATURE:
<221> NAME/KEY: Misc_feature
<222> LOCATION: (1)..(9)
<223> OTHER INFORMATION: GenBank Accession No. P55966, probable toxin

<400> SEQUENCE: 95

Thr Thr Asp Pro Gln Met Ser Lys Lys
1               5
```